(12) United States Patent
Hoshi

(10) Patent No.: US 8,716,453 B2
(45) Date of Patent: May 6, 2014

(54) CYSTATIN C, β2 MICROGLOBULIN, α1 MICROGLOBULIN AND GENES FOR SAME, ANTIBODY, AND KIT AND METHOD FOR DIAGNOSIS OF FELINE NEPHROPATHY

(75) Inventor: Fumio Hoshi, Sagamihara (JP)

(73) Assignees: School Juridical Person Kitasato Institute, Tokyo (JP); Nipro Corporation, Osaka-Shi (JP)

( * ) Notice: Subject to any disclaimer, the term of this patent is extended or adjusted under 35 U.S.C. 154(b) by 0 days.

(21) Appl. No.: 13/516,987

(22) PCT Filed: Dec. 16, 2010

(86) PCT No.: PCT/JP2010/072710
§ 371 (c)(1),
(2), (4) Date: Jun. 18, 2012

(87) PCT Pub. No.: WO2011/074651
PCT Pub. Date: Jun. 23, 2011

(65) Prior Publication Data
US 2013/0004971 A1    Jan. 3, 2013

(30) Foreign Application Priority Data

Dec. 17, 2009   (JP) ................. 2009-286711
Dec. 17, 2009   (JP) ................. 2009-286712
Feb. 18, 2010   (JP) ................. 2010-033676

(51) Int. Cl.
*C12P 21/08*    (2006.01)
(52) U.S. Cl.
USPC ............. 530/388.2; 530/388.1; 435/7.1
(58) Field of Classification Search
None
See application file for complete search history.

(56) References Cited

U.S. PATENT DOCUMENTS

2003/0027216 A1    2/2003   Kiernan et al.

FOREIGN PATENT DOCUMENTS

| WO | WO 2008/061149 A2 | 5/2008 |
| WO | WO 2008/116867 A1 | 10/2008 |
| WO | WO 2008/142057 A1 | 11/2008 |

OTHER PUBLICATIONS

Okamoto, Bunina Bodies in Amyotrophic Lateral Sclerosis. Neuropathol. 13: 193-99, 1993.*
Kuriyama et al., Monoclonal anti-dipeptide antibodies cross-react with detyrosinated and glutamylated forms of tubulin, Cell Motility and the Cytoskeleton 30:171-182 (1995).*
Nakata et al., Molecular cloning, expression in *Escherichia coli*, and development of monoclonal antibodies to feline cystatin C, Veterinary Immunology and Immunopathology, 138 (2010) 231-234.*
alpha-1-microglobulin/bikunin [*Bos taurus*]. online. Sep. 5, 1996 uploaded. NCBI Entrez Nucleotide, Accession No. AAB07599 (GI:1016298) [Retrieved on Jan. 25, 2011]. Retrieved from the Internet: <URL:http://www.ncbi.nlm.nih.gov/protein/AAB07599.1>, entire text.

(Continued)

*Primary Examiner* — Gail R Gabel
*Assistant Examiner* — Andrea S Grossman
(74) *Attorney, Agent, or Firm* — Birch, Stewart, Kolasch & Birch, LLP

(57) ABSTRACT

Proteins respectively having the amino acid sequences represented by SEQ ID NOs: 1, 17 and 32; structural genes respectively encoding the proteins, preferably respectively having the nucleotide sequences represented by SEQ ID NOs: 2, 18 and 33; an antibody capable of specifically binding to feline-derived cystatin C, feline-derived β2 microglobulin or feline-derived α1 microglobulin; a kit for diagnosing feline nephropathy, containing the antibody of the present invention; and a method for diagnosing feline nephropathy using the antibody of the present invention.

6 Claims, 30 Drawing Sheets

(56) References Cited

OTHER PUBLICATIONS alpha-1-microglobulin/bikunin precursor [*Sus scrofa*]. online. Oct. 3, 2009 uploaded. NCBI Entrez Nucleotide, Accession No. NP_001157478 (GI:255683402) [Retrieved on Jan. 25, 2011]. Retrieved from the Internet: <URL:http://www.ncbi.nlm.nih.gov/protein/255683402?sat=ncbi&satkey=33167164>, entire text.

alpha-1-microglobulin; bikunin [*Homo sapiens*]. online. Oct. 23, 2008 uploaded. NCBI Entrez Nucleotide, Accession No. CAA38585 (GI:825614) [Retrieved on Jan. 25, 2011]. Retrieved from the internet: <URL:http://www.ncbi.nlm.nih.gov/protein/CAA38585.1>, entire text.

beta-2-microglobulin precursor [*Homo sapiens*], online. Dec. 6, 2009 uploaded. NCBI Entrez Nucleotide, Accession No. NP_004039 (GI:4757826) [Retrieved on Jan. 25, 2011]. Retrieved from the internet: <URL:http://www.ncbi.nlm.nih.gov/protein/4757826?sat=ncbi&satkey=35828289>, entire text.

beta-2-microglobulin precursor [*Macaca mulatta*]. online. Sep. 3, 2009 uploaded. NCBI Entrez Nucleotide, Accession No. NP_001040602 (GI:114051850) [Retrieved on Jan. 25, 2011]. Retrieved from the Internet: <URL:http://www.ncbi.nlm.nih.gov/protein/114051850?sat=ncbi&satkey=32436143>, entire text.

beta-2-microglobulin protein [*Sus scrofa*]. online. Dec. 19, 2001 uploaded. NCBI Entrez Nucleotide, Accession No. AAL48289 (GI:17933431) [Retrieved on Jan. 25, 2011]. Retrieved from the internet: <URL:http://www.ncbi.nlm.nih.gov/protein/17933431?report=genbank&log$=protalign&blast_rank=1&RID=KWTPT92Z014>, entire text.

Boyd et al., "Survival in Cats with Naturally Occuring Chronic Kidney Disease (2000-2002)", J Vet Intern Med, 2008, vol. 22, pp. 1111-1117.

crystatin C [*Homo sapiens*]. online. Nov. 14, 2006 uploaded. NCBI Entrez Nucleotide, Accession No. CAA43856 (GI:4490944) [Retrieved on Jan. 25, 2011]. Retrieved from the Internet: <URL:http://www.ncbi.nlm.nih.gov/protein/CAA43856.2>, entire text.

crystatin C [*Sus scrofa*]. online. Aug. 27, 2006 uploaded. NCBI Entrez Nucleotide, Accession No. NP_001038067 (GI:113205858) [Retrieved on Jan. 25, 2011]. Retrieved from the Internet: <URL:http://www.ncbi.nlm.nih.gov/protein/113205858?sat=old06&satkey=6492928>, entire text.

crystatin-C precursor [*Macaca mulatta*]. online. Sep. 3, 2009 uploaded. NCBI Entrez Nucleotide, Accession No. NP_001028096 (GI:74136407) [Retrieved on Jan. 25, 2011]. Retrieved from the internet: <URL:http://www.ncbi.nlm.nih.gov/protein/74136407?sat=ncbi&satkey=32519226>, entire text.

En'yu Imai, "Shuyo Shoko Kensa kara Shindan eno Approach Shintai Choko Kensa kara Jin Nyoro-kei Shikkan o Mitsuke Dasu β2-Microglobulin, alpha 1-Microglobulin, NAG, Cystatin C [Seijin]", The Journal of the Japan Medical Association, 2007, vol. 136, No. special extra issue (2), pp. S88-S89, entire text.

International Search Report for PCT/JP2010/072710 dated Feb. 8, 2011.

Unknown, "β2-Microglobulin, α1-Microglobulin, NAG, and Cystatin C [Adult]", Japan Medical Association Journal, vol. 136, Special No. (2), Oct. 15, 2007, pp. S88-S89.

Japanese Office Action and English translation thereof, mailed Oct. 8, 2013, for Patent Application No. 2009-286711.

Japanese Office Action and English translation thereof, mailed Oct. 8, 2013, for Patent Application No. 2009-286712.

Japanese Office Action and English translation thereof, mailed Oct. 8, 2013, for Patent Application No. 2010-033676.

Bagshaw et al., "Urinary biomarkers in septic acute kidney injury," Intensive Care Med, vol. 33, 2007, pp. 1285-1296, XP19536303.

Dati et al., "Standardization activities for harmonization of test results," Clinica Chimica Acta, vol. 297, 2000, PP. 239-249, XP55067242.

Extended European Search Report for European Application No. 10837676.5, dated Jul. 31, 2013.

Hotta at al., "Usefulness of serum cystatin-C as a marker of the renal function: a comparative evaluation with β2-microglobulin, α1-microglobulin and creatinine," Jpn J Nephrol, vol. 41, No. 8, 1999, pp. 797-803, XP008124015.

Mussap et al., "Predictive value of amniotic fluid cystatin C levels for the early identification of fetuses with obstructive uropathies," BJOG: an International Journal of Obstetrics and Gynaecology, vol. 109, Jul. 2002, pp. 778-783, XP002408780.

Pontius et al., "Initial sequence and comparative analysis of the cat genome," Genome Research, vol. 17, 2007, pp. 1675-1689, XP2699106.

Tian et al., "Cystatin C measurement and its practical use in patients with various renal diseases," Clinical Nephrology, vol. 48, No. 2, 1997, pp. 104-108, XP009063131.

Tonomura et al., "Evaluation of the usefulness of urinary biomarkers for nephrotoxicity in rats," Toxicology, vol. 273, 2010, pp. 53-59, XP27065778.

* cited by examiner

```
CAT     1- MAGSLRTPLIILAAV--AITLALAMSPGT-GRRNNKS-ALVGAPLDADVNEEGVQQAINFALSEYNKASNDAYHSRAMRV
HUMAN   1- MAGPLRAPLLLLA----ILAVALAVSPAA-GSSPGKPPRLVGGPMDASVEEEGVRRALDFAVGEYNKASNDMYHSRALQV
MONKEY  1- MAGPIRAPLLLLA----ILAVALAVSPAA-GASPGKPPRLVGGPMDASVEEEGVRRALDFAVSEYNKASNDMYHSRALQV
COW     1- MVGSPRAPLLLLASLIVALALALAVSPAA-AQGPRKG-RLLGGLMEADVNEEGVQEALSFAVSEFNKRSNDAYQSRVVRV
PIG     1- MAGSPRSPLLILAAL--ALALALAVSPAA-GQ-GHKG-RLVGGLIDADVNEEGVQQAISFALSEYNKASNDAYHGRVLRV
RAT     1- MA--------------SPLRSLMLLLAVLAVAWAGTSRPPPRLLGAPQEADASEEGVQRALDFAVSEYNKGSNDAYHSRAIQV

CAT    77- VRARKQVVAGMNYFLDVEIGRTRCTKSQPNLDTCPFHDQPHLMRKTLCSFQIYTVPWMGKTSIVKSSCQDA
HUMAN  76- VRARKQIVAGVNYFLDVELGRTTCTKTQPNLDNCPFHDQPHLKRKAFCSFQIYAVPWQGTMTLSKSTCQDA
MONKEY 76- VRARKQIVAGVNYFLDVELGRTTCTKTQPNLDNCPFHEQPHLKRKAFCSFQIYTVPWQGTMTLSKSTCQDA
COW    79- VRARKQVVSGMNYFLDVELGRTTCTKSQANLDSCPFHNQPHLKREKLCSFQVYVPWMNTINLVKFSCQD-
PIG    76- LRVRKQVVAGMNYFLEVEIGRTTCTKSQANLDNCPFPNQPDLQKTLCSFQVYTVPWKGTTSIVKSSCRDE
RAT    70- VRARKQIVAGINYYIDVEMGRTTCTKSQTNLITNCPFHDQPHLMRKALCSFQIYSVPWKGTHTLTKSSCKNA
```

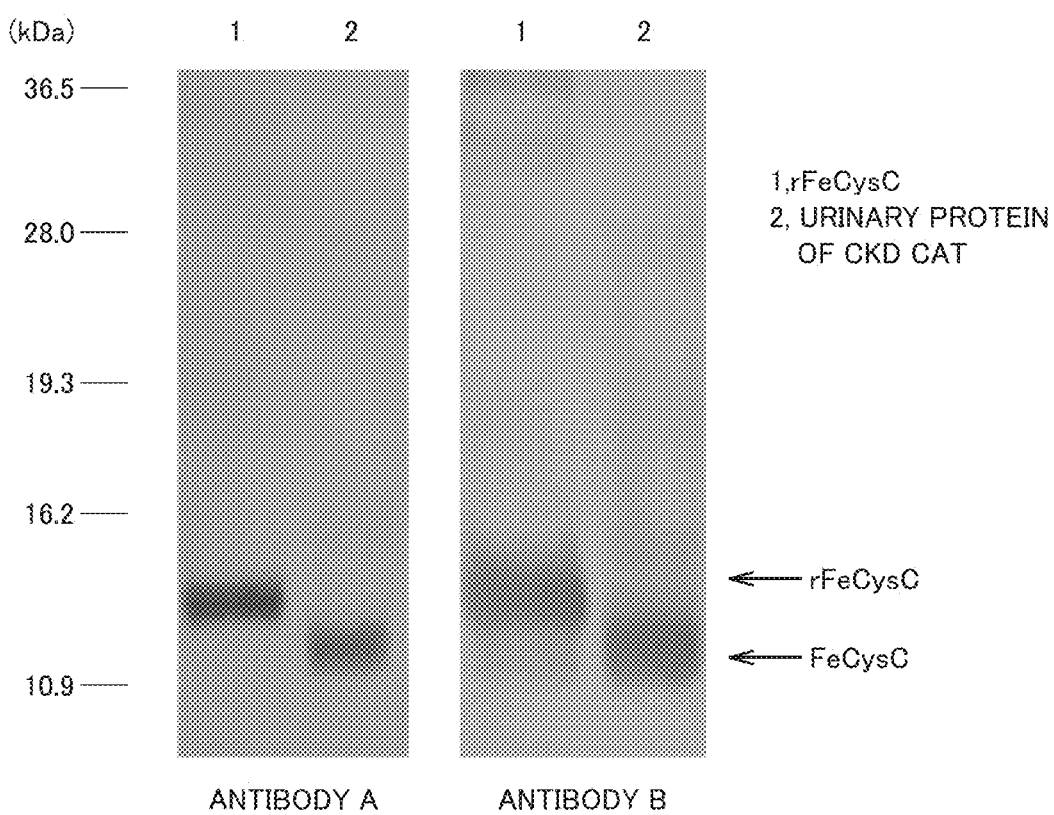

| | | |
|---|---|---|
| CAT | 1:MARFVVLVLLGLLYLSHLDAVQHSPKVQVYSRHPAENGKPNFLNCVYSGFHPPQIDITLM | 60 |
| HUMAN | 1:MSRSVALAVLALLSLSGLEAIQRTPKIQVYSRHPAENGKSNFLNCYVSGFHPSDIEVDLL | 60 |
| HORSE | 1:MARWALVLLGLLSLITGLEAVPRVPKVQVYSRHPAENGKPNFLNCYVSGFHPPEIEIDLL | 60 |
| COW | 1:MARFVALVLLGLLSLSGLDAIQRPPKIQVYSRHPEDGKPNFLNCVYGFHPPQIEIDLL | 60 |
| PIG | 1:MAPLVALVLLGLLSLSGLDAVARPPKVQVYSRHPAENGKPNVLNCVYSGFHPPQIEIDLL | 60 |
| MOUSE | 1:MARSVTLVFLMLVSHTGLMAIQKTPQIQVYSRHPPENGKPNLLNCVYTQFHPPHIEIQML | 60 |
| MONKEY | 1:MFRSVALAVLAILFLSGLEAIQRAPKIQVYSRHPPENGKSNFLNCYVSGFHPSDIEVDLL | 60 |
| RAT | 1:MARSVTVIFHLMLVSLAVVLAIQKTPQIQVYSRHPPENGKPNFLNCYVSQFHPPQIEIDLL | 60 |
| | | |
| CAT | 61:KNGKKMEA-EQTDLSFNRDWTFYLLVHTEFTPNVEDEYSCQVNHTTLSEPKVVMWERDT | 118 |
| HUMAN | 61:KNGERIEHVEHSDLSFSKDWSFYLLYYTEFTPTEKDEYACRVNHVTLSQPKIVKWDRDM | 119 |
| HORSE | 61:KNGEKN-KVDRSDLSFSKDWSFYLLVHTDFTPNGFTPNSKIQYSCRVKIVNTLEQRKIDPLIVKWDRDL | 118 |
| COW | 61:KNGEKI-KSEQSDLSFSKDWSFYLLSIAEFTPNSKIQYSCRVKIVNTLEQRKIVKWDRDL | 118 |
| PIG | 61:KNGEKINA-EQSDLSFSKDWSFYLLVHTEFTPNAVIDQYSCRVKIVTLDKPKIIVKWDRDH | 118 |
| MOUSE | 61:KNGKKIPKVEHSDMSFSKDWSFYILAHTEFTPJETIDHACRVKHASMAEPKIIVKWDRDM | 119 |
| MONKEY | 61:KNGERMGKVEHSDLSFSKDWSFYLLYHNEKDEYACRVNHVTLSGPRTVKWDRDM | 119 |
| RAT | 61:KNGKKIPNIEMSDLSFSKDWSFYJLAHTEFTPJETDVACRVKIVMTLKEPKIVKWDRDM | 119 |

1, RFeβ$_2$-m
2, URINARY PROTEIN OF CKD CAT

← Feβ$_2$-m
← RFeβ$_2$-m

ANTIBODY A    ANTIBODY B

FIG.22

```
β2-mcDNA    1:  --------GTCCAGCATTCTCCAAAGGTTCAGGTTTACTCCCGTCACCCAGCAGAGAA  50
pcDNAfβ2m   1:  CTGGGATCCGTCCAGCATTCTCCAAAGGTTCAGGTTTACTCCCGTCACCCAGCAGAGAA  60

β2-mcDNA   51:  TGGAAAGCCAAATTTTCTGAACTGCTACGTTTCGGGGTTCCACCCACCACAAATTGATAT  110
pcDNAfβ2m  61:  TGGAAAGCCAAATTTTCTGAACTGCTACGTTTCGGGGTTCCACCCACCACAAATTGATAT  120

β2-mcDNA  111:  CACCTTGATGAAGAATGGAAAGAAGATGGAAGCGGAACAGACAGATCTGTCCTTCAACAG  170
pcDNAfβ2m 121:  CACCTTGATGAAGAATGGAAAGAAGATGGAAGCGGAACAGACAGATCTGTCCTTCAACAG  180

β2-mcDNA  171:  GGACTTTCTATCTTCTGGTCCACACCGAATTTACTCCCACTGTCGAAGATGAGTA  230
pcDNAfβ2m 181:  GGACTTTTCTATCTTCTGGTCCACACCGAATTTACTCCCACTGTCGAAGATGAGTA  240

β2-mcDNA  231:  TAGCTGCCAAGTGAATCATACTCTCAGTGAGCCCAAGGTCGTTAAGTGGGATCGAGA  290
pcDNAfβ2m 241:  TAGCTGCCAAGTGAATCATACTCTCAGTGAGCCCAAGGTCGTTAAGTGGGATCGAGA  300

β2-mcDNA  291:  CATGTAA---------  297
pcDNAfβ2m 301:  CATGTAAGTCGACTCGA  317
```

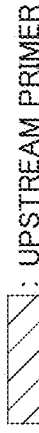 : RESTRICTION ENZYME SEQUENCE OF Bam HI  : UPSTREAM PRIMER 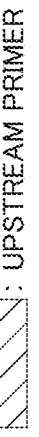

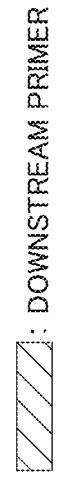 : RESTRICTION ENZYME SEQUENCE OF Sal I  : DOWNSTREAM PRIMER 

| | | |
|---|---|---|
| CAT | 1- | MAGSLRTPLILIAAV--ALTLALAMSPGT-GRRNNKS-ALVGAPLDADVNEEGVQQALNFALSEYNKASNDAYHSRAMRV |
| HUMAN | 1- | MAGPLRAPLLLLA----ILAVALAVSPAA-GSSPGKPPRLVGG-PMDASVEEEGVRRALDFAVGEYNKASNDMYHSRALQV |
| MONKEY | 1- | MAGPLRAPLILLA----ILAVALAVSPAA-GASPGKPPRLVGG-PMDASVEEEGVRRALDFAVSEYNKASNDMYHSRALQV |
| COW | 1- | MVGSPRAPLLLLASLIVALALALAVSPAA-AQGPRKG-RLLGGLMEADVNEEGVQEALSFAVSEFNKRSNDAYQSRVVRV |
| PIG | 1- | MAGSPRSPLLLIAAL--ALALALAVSPAA-GQ-GHKG-RLVGGLIDADVNEEGVQQALSFALSEYNKASNDAYHGRVLRV |
| RAT | 1- | MA--------SPLRSLMLLLAVLAVAWAGTSRPPPRLLGAPQEADASEEGVQRALDFAVSEYNKGSNDAYHSRAIQV |
| | | |
| CAT | 77- | VRARKQVVAGMNYFLDVEIGRTRCTKSQPNLDTCPFHDQPHLMRKTLCSFQIYTVPWMGKTSLVKSSCQDA |
| HUMAN | 76- | VRARKQIVAGVNYFLDVELGRTTCTKTQPNLDNCPFHDQPHLKRKAFCSFQIYAVPWQGTMTLSKSTCQDA |
| MONKEY | 76- | VRARKQIVAGVNYFLDVELGRTTCTKTQPNLDNCPFHEQPHLKRKAFCSFQIYTVPWQGTMTLSKSTCQDA |
| COW | 79- | VRARKQVVSGMNYFLDVELGRTTCTKSQANLDSCPFHNQPHLKREKLCSFQVYTVVPWMNTINLVKFSCQD- |
| PIG | 76- | LRVRKQVVAGMNYFLEVEIGRTTCTKSQANLDNCPFPNQPDLQKTLCSFQVYTVPWKGTTSLVKSSCRDE |
| RAT | 70- | VRARKQLIVAGINYYLDVEMGRTTCTKSQTNLTNCPFHDQPHLMRKALCSFQIYSVPWKGTHTLTKSSCKNA |

1, rFe $\alpha_1$-m
2, URINARY PROTEIN OF CKD CAT

ANTIBODY A        ANTIBODY B

1: SUPERNATANT (SOLUBLE FRACTION)
2: SEDIMENT (INSOLUBLE FRACTION)
3: AFFINITY CHROMATOGRAPHY ELUATE
4: PROTEASE REACTION LIQUID

CYSTATIN C, β2 MICROGLOBULIN, α1 MICROGLOBULIN AND GENES FOR SAME, ANTIBODY, AND KIT AND METHOD FOR DIAGNOSIS OF FELINE NEPHROPATHY

TECHNICAL FIELD

The present invention relates to feline-derived cystatin C, β2 microglobulin, and α1 microglobulin and genes encoding the same. The present invention also relates to an antibody against feline-derived cystatin C, β2 microglobulin, or α1 microglobulin, a kit and a method for diagnosis of feline nephropathy using the same.

BACKGROUND ART

Recently, the number of families having a pet is steadily increasing in association with the low birthrate. However, such pets are often not kept in a manner suited for the nature of the pets. In particular, as a result of unbalanced diet, a pet can have a symptom like an adult disease such as diabetes mellitus, and there is also a case that the pet is taken to a veterinarian.

Under such a situation, business of diagnosis for pets has been increasing in recent years. If nephropathy of a pet could be found early, a veterinarian could provide direction to the guardian for improving the manner of having the pet, especially the manner of feeding. Generally, cystatin C (CysC), β2 microglobulin ($\beta_2$-m), and α1 microglobulin ($\alpha_1$-m) are recited as markers for nephropathy.

Cystatin C, for example, derived from human, is a basic low molecular protein having a molecular weight of 13000 Da. Human-derived cystatin C is produced in cells throughout the human body, and is secreted outside cells at a constant production amount without considerably influenced by environmental change inside and outside the cells, and is recently reported to be useful as an index for early diagnosis of diabetic nephropathy.

β2 microglobulin, for example, derived from human, is produced in cells throughout the human body, and is secreted outside cells at a constant production amount without considerably influenced by environmental change inside and outside the cells, and is recently reported to be useful as an index for early diagnosis of diabetic nephropathy.

α1 microglobulin, for example, derived from human, is produced in cells throughout the human body, and is secreted outside cells at a constant production amount without considerably influenced by environmental change inside and outside the cells, and is recently reported to be useful as an index for early diagnosis of diabetic nephropathy.

However, it is the current state of art that as for feline-derived cystatin C, β2 microglobulin, and α1 microglobulin, not only an antibody specific to the protein does not exist, but also an amino acid sequence of the protein has not been elucidated yet.

CITATION LIST

Non Patent Literature

NPL 1: Non-Patent Document 1: Journal of Veterinary Internal Medicine. 22 (5): 1111-1117, 2008

SUMMARY OF INVENTION

Technical Problem

The present invention was devised to solve the aforementioned problem, and it is an object of the present invention to provide an antibody specific to feline-derived cystatin C, β2 microglobulin or α1 microglobulin, and to provide a method and a kit capable of diagnosing feline nephropathy rapidly and conveniently using the same.

Solution to Problem

As a result of diligent effort, the present inventor first identified a structural gene encoding cystatin C, β2 microglobulin or α1 microglobulin in feline genes, and expressed feline-derived cystatin C, β2 microglobulin or α1 microglobulin from the structural gene, and analyzed an amino acid sequence thereof. Further, an antibody specific to feline-derived cystatin C, β2 microglobulin or α1 microglobulin was prepared, and accomplished the present invention. Specifically, the present invention is as follows.

The present invention provides a protein having the amino acid sequence represented by SEQ ID NO: 1, SEQ ID NO: 17 or SEQ ID NO: 32.

The present invention also provides a structural gene encoding the protein of the present invention described above. The structural gene of the present invention preferably has a nucleotide sequence represented by SEQ ID NO: 2, SEQ ID NO: 18 or SEQ ID NO: 33.

The present invention also provides an antibody specifically binding to feline-derived cystatin C, β2 microglobulin or α1 microglobulin. The antibody of the present invention is preferably produced by a cell line Mouse-Mouse hybridoma CysC mAb1 (Accession No.: FERM P-21877), a cell line Mouse-Mouse hybridoma CysC mAb2 (Accession No.: FERM P-21878), a cell line Mouse-Mouse hybridoma $\beta_2$-m mAb1 (Accession No.: FERM P-21879), a cell line Mouse-Mouse hybridoma $\beta_2$-m mAb2 (Accession No.: FERM P-21880), a cell line Mouse-Mouse hybridoma $\alpha_1$-m mAb1 (Accession No.: FERM P-21910), or a cell line Mouse-Mouse hybridoma $\alpha_1$-m mAb2 (Accession No.: FERM P-21911) against the protein of the present invention described above as an antigen.

The present invention also provides a kit for diagnosis of feline nephropathy containing the antibody of the present invention described above.

The present invention also provides a method for diagnosis of feline nephropathy using the antibody of the present invention described above.

Advantageous Effects of Invention

According to the present invention, it becomes possible to diagnose feline nephropathy dramatically rapidly and conveniently compared with conventional cases.

BRIEF DESCRIPTION OF DRAWINGS

FIG. 1 is a chart showing an amino acid sequence of feline-derived CysC, in comparison with known amino acid sequences of CysC of human, monkey, cow, pig and rat.

FIG. 2 is a chart showing a nucleotide sequence of cDNA of feline-derived CysC gene, in comparison with known nucleotide sequences of CysC gene of human, monkey, cow, pig and rat.

FIG. 3 is a photograph showing an experimental result of specificity of antibodies A and B to feline native CysC in Experimental Example 3.

FIG. 11 is a chart showing an amino acid sequence of feline-derived $\beta_2$-m, in comparison with known amino acid sequences of $\beta_2$-m of human, horse, cow, pig, mouse, monkey and rat.

FIG. 12 is a chart showing a nucleotide sequence of cDNA of feline-derived $\beta_2$-m gene, in comparison with known nucleotide sequences of $\beta_2$-m gene of human, horse, cow, pig, mouse, monkey and rat.

FIG. 22 is an illustration schematically showing a sequence analysis result of pcDNA-F $\beta_2$-m in Experimental Example 5.

FIG. 29 is a chart showing an amino acid sequence of feline-derived $\alpha_1$-m, in comparison with known amino acid sequences of $\alpha_1$-m of human, horse, cow, pig, mouse, monkey and rat.

FIG. 30 is a chart showing a nucleotide sequence of cDNA of feline-derived $\alpha_1$-m gene, in comparison with known nucleotide sequences of $\alpha_1$-m gene of human, horse, cow, pig, mouse, monkey and rat.

DESCRIPTION OF EMBODIMENTS

Figure 4:
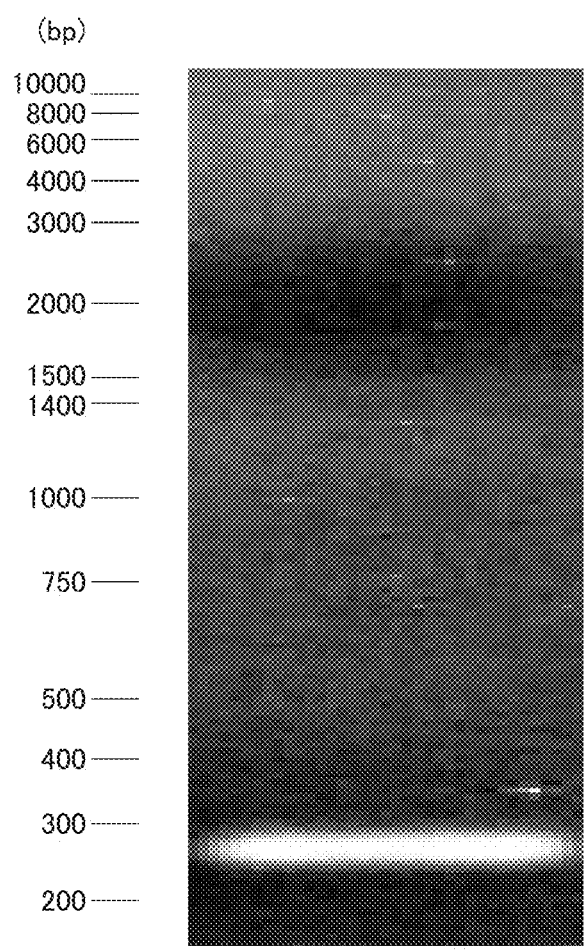
FIG. 4 is an electrophoretic photograph showing a result of PCR of first-strand cDNA in Experimental Example 1.

[1] Cystatin C and Gene Thereof, Anti-Cystatin C Antibody

According to the present invention, a protein having the amino acid sequence represented by SEQ ID NO: 1 is provided. The present inventor first identified a structural gene encoding cystatin C (in this description, referred to as "CysC gene") in feline genes, and first analyzed an amino acid sequence of feline-derived cystatin (in this description, referred to as "CysC") by the CysC gene. The protein of the present invention having the amino acid sequence represented by SEQ ID NO: 1 is feline-derived cystatin C for which the amino acid sequence is first identified herein by the present inventor.

Figure 1:
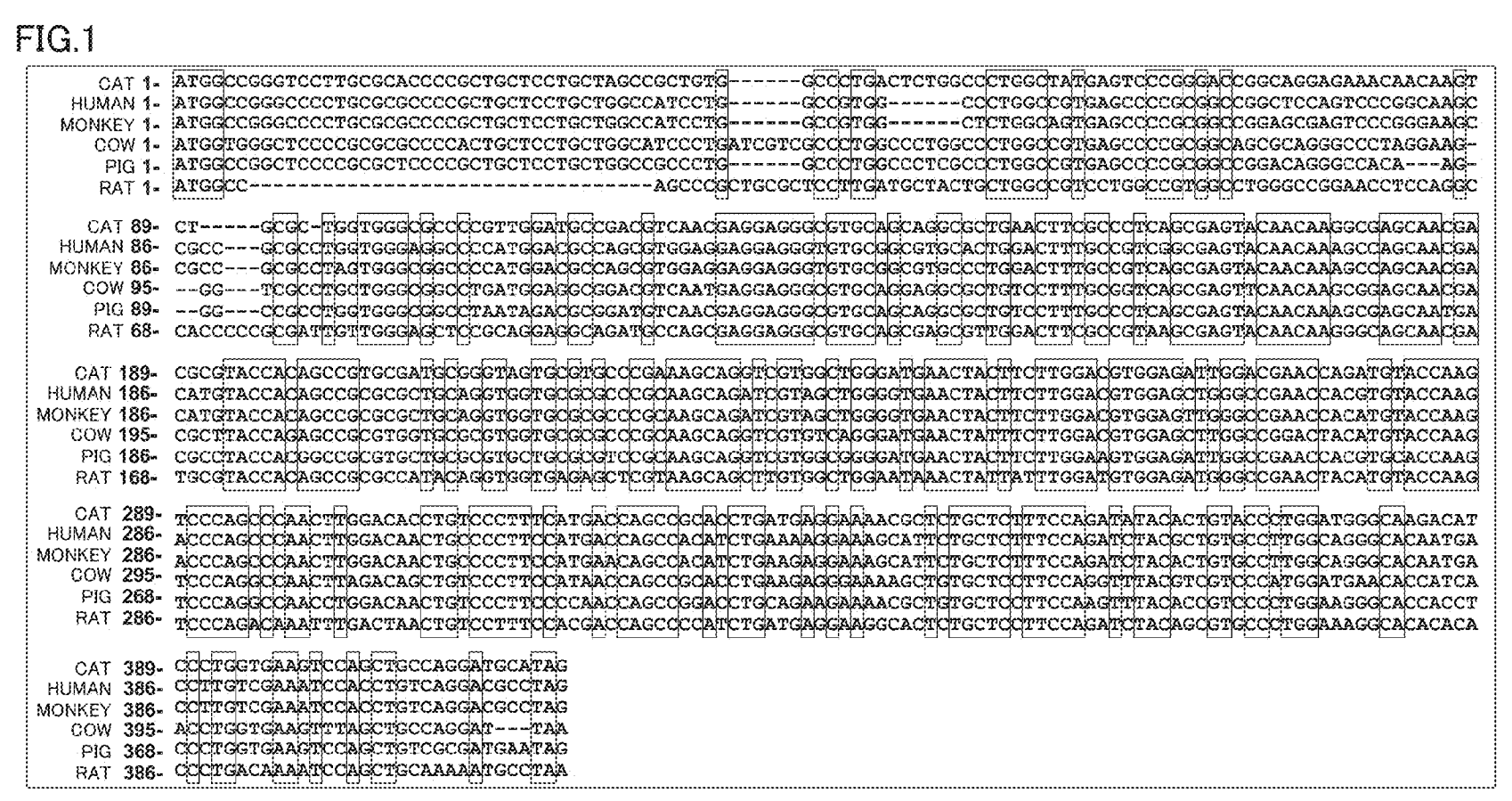

Here, FIG. 1 is a chart showing the amino acid sequence of the protein (feline CysC) of the present invention represented by SEQ ID NO: 1, in comparison with known amino acid sequences of CysC of human, monkey, cow, pig and rat. In FIG. 1, the part surrounded by a square is the amino acid sequence that is common among various animal species. The number of amino acids in the protein of the present invention represented by SEQ ID NO: 1 is 147 in the entire length, which is approximate to the number of amino acids of 146 in human, monkey and pig, the number of amino acids of 148 in cow, and the number of amino acids of 140 in rat, and the position and the number of structure amino acid cysteine conserved among other animal species are similar. While the detail will be described later in Experimental Example 2, from the fact that the amino acid sequence of the protein of the present invention has an average homology of 69.15% with amino acid sequences of CysC of other animal species, and homologies of amino acid sequences of CysC among other animal species (human, cow, pig and rat) distribute within the range of 62.22 to 97.26%, the protein of the present invention is estimated as feline-derived CysC.

The feline-derived CysC of the present invention is preferably obtained by artificial synthesis. This time, the inventor of the present invention first found a nucleotide sequence of a structural gene (CysC gene) of feline-derived CysC (nucleotide sequence represented by SEQ ID NO: 2). The present invention also provides a structural gene encoding feline-derived cystatin, and this structural gene preferably has a nucleotide sequence represented by SEQ ID NO: 2. That is, the structural gene of the present invention may include another nucleotide sequence as an intron as far as it includes the nucleotide sequence represented by SEQ ID NO: 2 as, an exon.

Here, FIG. 2 is a chart showing a structural gene (feline CysC gene) of the present invention represented by SEQ ID NO: 2, in comparison with known nucleotide sequences of CysC gene of human, monkey, cow, pig and rat. In FIG. 2, the part surrounded by a square indicates the nucleotide sequence that is common among various animal species. As for nucleic acid length of CysC gene, in comparison with 441 bases in human, monkey and pig, 447 bases in cow, and 423 bases in rat, the length of feline CysC gene of the present invention represented by SEQ ID NO: 2 was 444 bases. From the fact that homology between the nucleotide sequence of feline CysC gene of the present invention represented by SEQ ID NO: 2, and nucleotide sequences of CysC gene of other animal species is 77.69% on average, and homologies of nucleotide sequence of CysC gene among other animal species (human, monkey, cow, pig and rat) distribute within the range of 67.21 to 96.71%, the structural gene of the present invention is estimated as feline-derived CysC gene.

The present invention also provides a novel antibody that specifically binds to feline-derived CysC. While the detail will be described later in Experimental Example 3, the inventor of the present invention expressed feline-derived CysC from the feline-derived CysC gene of the present invention as described above, and prepared a cell capable of producing an antibody against the same as an antigen. Such a cell line is novel, and the present applicant et al. deposited the cell line with International Patent Organism Depositary, National Institute of Advanced Industrial Science and Technology on Dec. 1, 2009 (Accession Nos.: FERM P-21877 and FERM P-21878).

The antibody of the present invention is preferably produced by a cell line Mouse-Mouse hybridoma CysC mAb1 (Accession No.: FERM P-21877) or a cell line Mouse-Mouse hybridoma CysC mAb2 (Accession No.: FERM P-21878) against the protein of the present invention as described above as an antigen. Here, FIG. 3 is a photograph showing an experimental result revealing that the antibody of the present invention specifically binds to feline native CysC. While the detail will be described later in Experimental Example 3, antibody A shown in FIG. 3 is a monoclonal antibody of isotype of κ chain of IgG1 produced by a cell line Mouse-Mouse hybridoma CysC mAb1 (Accession No.: FERM P-21877), and antibody B is an antibody of isotype of κ chain of IgG2a produced by a cell line Mouse-Mouse hybridoma CysC mAb2 (Accession No.: FERM P-21878). As shown in FIG. 3, it is recognized that the antibody of the present invention is capable of specifically binding to feline native CysC.

[2] β2 Microglobulin and Gene Thereof, Anti-β2 Microglobulin Antibody

According to the present invention, a protein having the amino acid sequence represented by SEQ ID NO: 17 is provided. The present inventor first identified a structural gene encoding β2 microglobulin (in this description, referred to as "$β_2$-m gene") in feline genes, and first analyzed an amino acid sequence of feline-derived β2 microglobulin (in this description, referred to as "$β_2$-m") by the $β_2$-m gene. The protein of the present invention having the amino acid sequence represented by SEQ ID NO: 17 is feline-derived β2 microglobulin for which the amino acid sequence is first identified by the present inventor.

Figure 11:
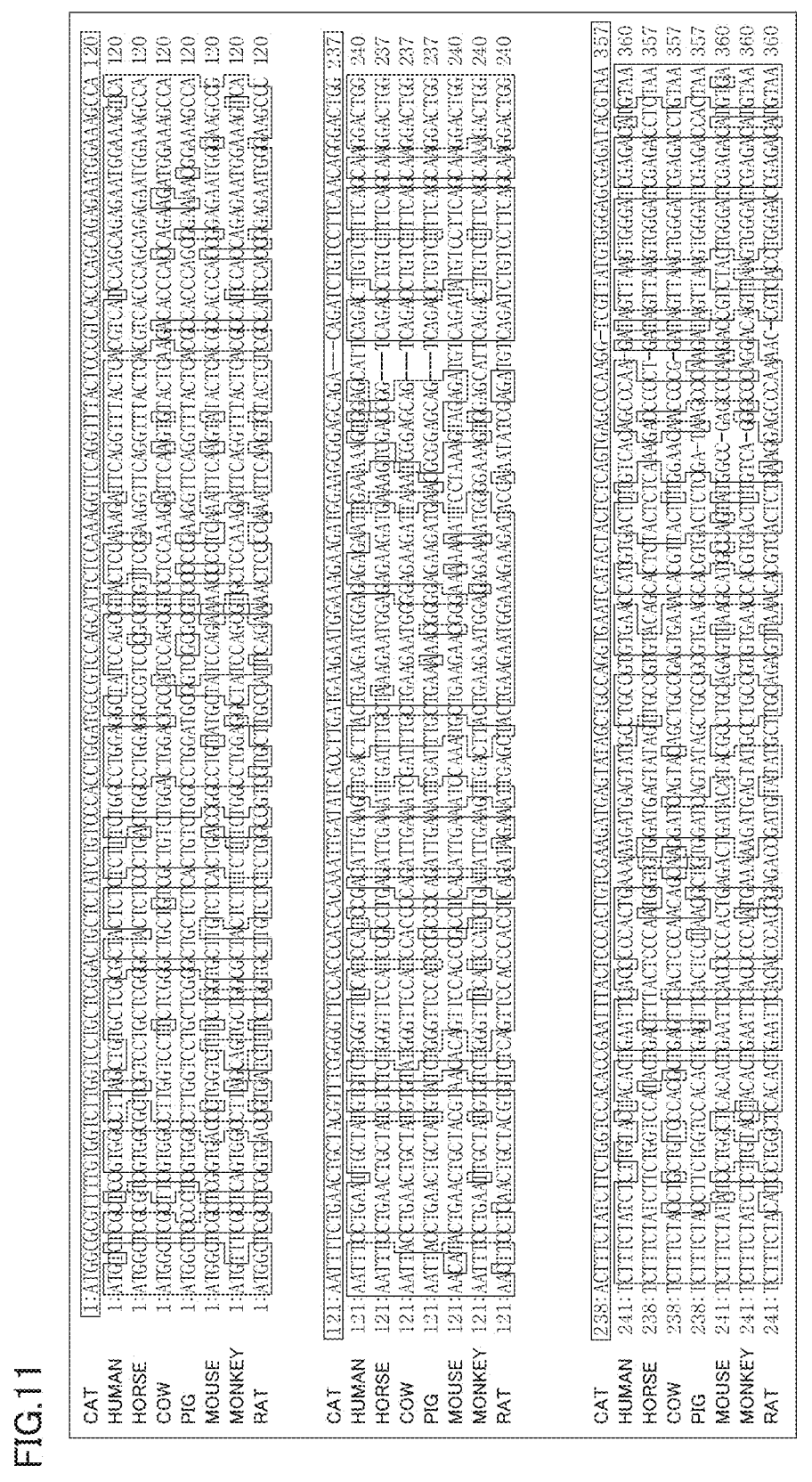

Here, FIG. 11 is a chart showing the amino acid sequence of the protein of the present invention represented by SEQ ID NO: 17 (feline $β_2$-m), in comparison with known amino acid sequences of $β_2$-m in human, horse, cow, pig, mouse, monkey and rat. In FIG. 11, the part surrounded by a square indicates an amino acid sequence that is common among various animal species. The number of amino acids in the protein of the present invention represented by SEQ ID NO: 17 is 118 in the entire length, which is very approximate to the number of amino acids of 119 in human, monkey, mouse and rat, and 118 in horse, cow and pig. While the detail will be described later in Experimental Example 5, from the fact that the amino acid sequence of the protein of the present invention has an average homology of 72.8% with amino acid sequences of $β_2$-m of other animal species, and average homology of amino acid sequence of $β_2$-m among other animal species (human, horse, cow, pig, mouse, monkey and rat) is 66.8%, the protein of the present invention is estimated as feline-derived $β_2$-m.

The feline-derived $β_2$-m of the present invention is preferably obtained by artificial synthesis. This time, the present inventor first found a nucleotide sequence of a structural gene ($β_2$-m gene) of feline-derived $β_2$-m (nucleotide sequence represented by SEQ ID NO: 18). The present invention also provides a structural gene encoding feline-derived β2 microglobulin, and this structural gene preferably has a nucleotide sequence represented by SEQ ID NO: 18. That is, the structural gene of the present invention may include another nucleotide sequence as an intron as far as it includes the nucleotide sequence represented by SEQ ID NO: 18 as an exon.

Here, FIG. 12 is a chart showing the structural gene of the present invention (feline $β_2$-m gene) represented by SEQ ID NO: 18, in comparison with known nucleotide sequences of $β_2$-m gene of human, horse, cow, pig, mouse, monkey and rat. In FIG. 12, the part surrounded by a square indicates the nucleotide sequence that is common among various animal species. While nucleic acid length of $β_2$-m gene was 360 bases in human, monkey, mouse and rat, and 357 bases in horse, cow and pig, the length was 357 bases in the feline $β_2$-m gene of the present invention represented by SEQ ID NO: 18. From the fact that homology between the nucleotide sequence of feline $β_2$-m gene of the present invention represented by SEQ ID NO: 18 and nucleotide sequences of $β_2$-m gene of other animal species is 72.9% on average, and average homology of nucleotide sequence of $β_2$-m gene among other animal species (human, horse, cow, pig, mouse, monkey and rat) is 72.8%, the structural gene of the present invention is estimated as feline-derived $β_2$-m gene.

The present invention also provides a novel antibody that specifically binds to feline-derived $β_2$-m. While the detail will be described later in Experimental Example 6, the inventor of the present invention expressed feline-derived $β_2$-m from the feline-derived $β_2$-m gene of the present invention as described above, and prepared a cell capable of producing an antibody against the same as an antigen. Such a cell line is novel, and the present applicant et al. deposited the cell line with International Patent Organism Depositary, National Institute of Advanced Industrial Science and Technology on Dec. 1, 2009 (Accession Nos.: FERM P-21879 and FERM P-21880).

Figure 13:
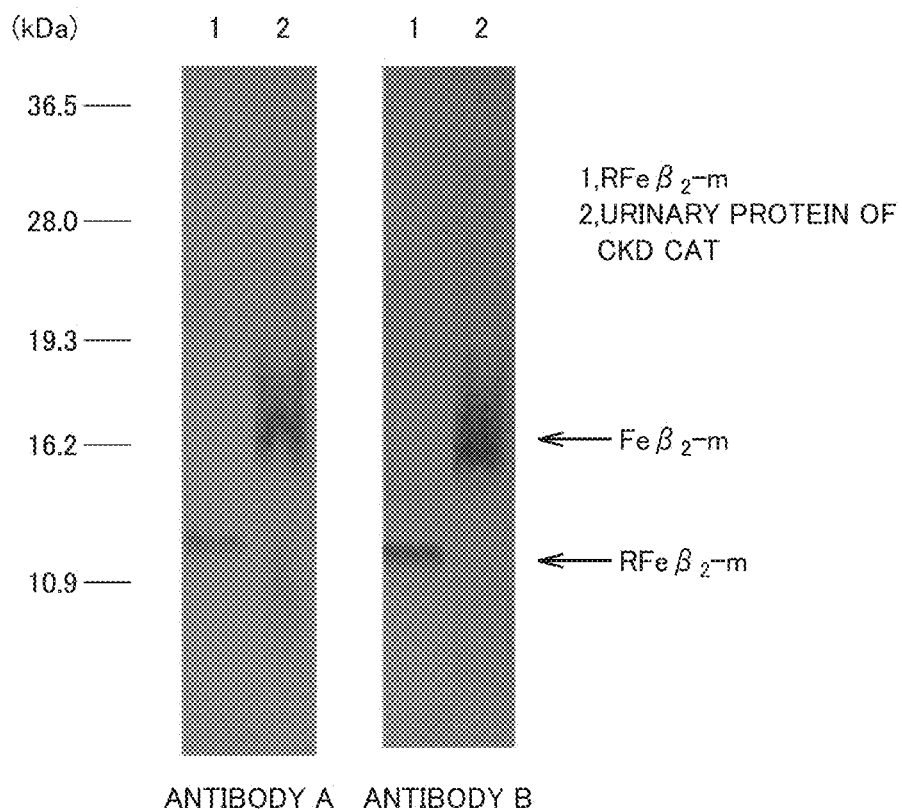
FIG. 13 is a photograph showing an experimental result of specificity of antibodies C and D to feline native $\beta_2$-m in Experimental Example 6.
Figure 14:
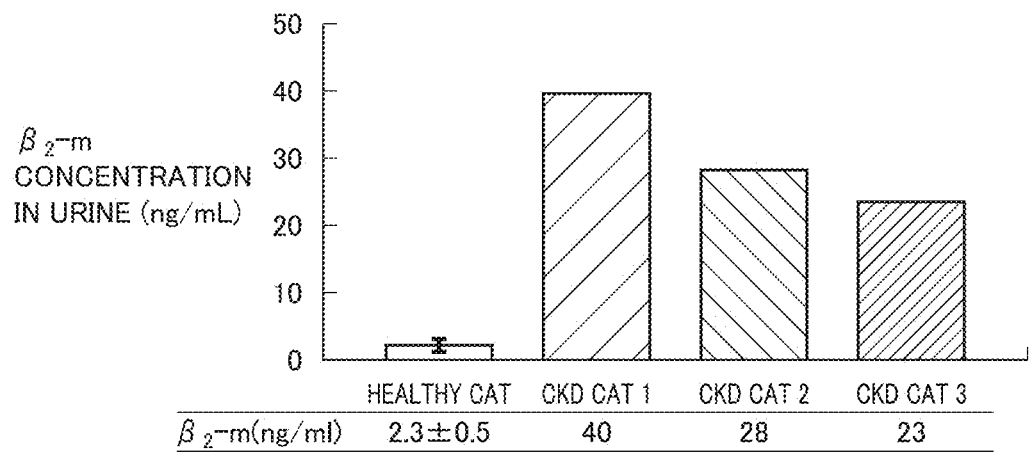
FIG. 14 is a graph showing a result of quantification of $\beta_2$-m in urine of one healthy cat and three cats suffering from chronic kidney disease using antibodies C and D.

The antibody of the present invention is preferably produced by a cell line Mouse-Mouse hybridoma $\beta_2$-m mAb1 (Accession No.: FERM P-21879) or a cell line Mouse-Mouse hybridoma $\beta_2$-m mAb2 (Accession No.: FERM P-21880) against the protein of the present invention as described above as an antigen. Here, FIG. 13 is a photograph showing an experimental result revealing that the antibody of the present invention specifically binds to feline native $\beta_2$-m. While the detail will be described later in Experimental Example 6, antibody C shown in FIG. 13 is a monoclonal antibody of isotype of K chain of IgG1 produced by a cell line Mouse-Mouse hybridoma $\beta_2$-m mAb1 (Accession No.: FERM P-21879), and antibody D is an antibody of isotype of K chain of IgG2b produced by a cell line Mouse-Mouse hybridoma $\beta_2$-m mAb2 (Accession No.: FERM P-21880). As shown in FIG. 13, it is recognized that the antibody of the present invention is capable of specifically binding to feline native $\beta_2$-m. FIG. 14 is a graph showing a result of quantification of $\beta_2$-m in urine of one healthy cat and three cats suffering from chronic kidney disease using antibodies C and D of the present invention. While the detail will be described later in Experimental Example 6, it is recognized from FIG. 14 that the antibodies C and D of the present invention little react with urine of the healthy cat, but react with all the three cats suffering from chronic kidney disease. This suggests that urine of a cat suffering from chronic kidney disease contains plenty of $\beta_2$-m, and it is recognizable that the antibody of the present invention can be used for diagnosis of feline nephropathy.

[3] α1 Microglobulin and Gene Thereof, Anti-α1 Microglobulin Antibody

According to the present invention, a protein having the amino acid sequence represented by SEQ ID NO: 32 is provided. The present inventor first identified a structural gene encoding α1 microglobulin (in the present description, referred to as "$\alpha_1$-m gene") in feline genes, and first analyzed an amino acid sequence of feline-derived α1 microglobulin (in the present description, referred to as "$\alpha_1$-m") by the $\alpha_1$-m gene. The protein of the present invention having the amino acid sequence represented by SEQ ID NO: 32 is feline-derived α1 microglobulin for which the amino acid sequence is first identified by the present inventor.

Figure 29:
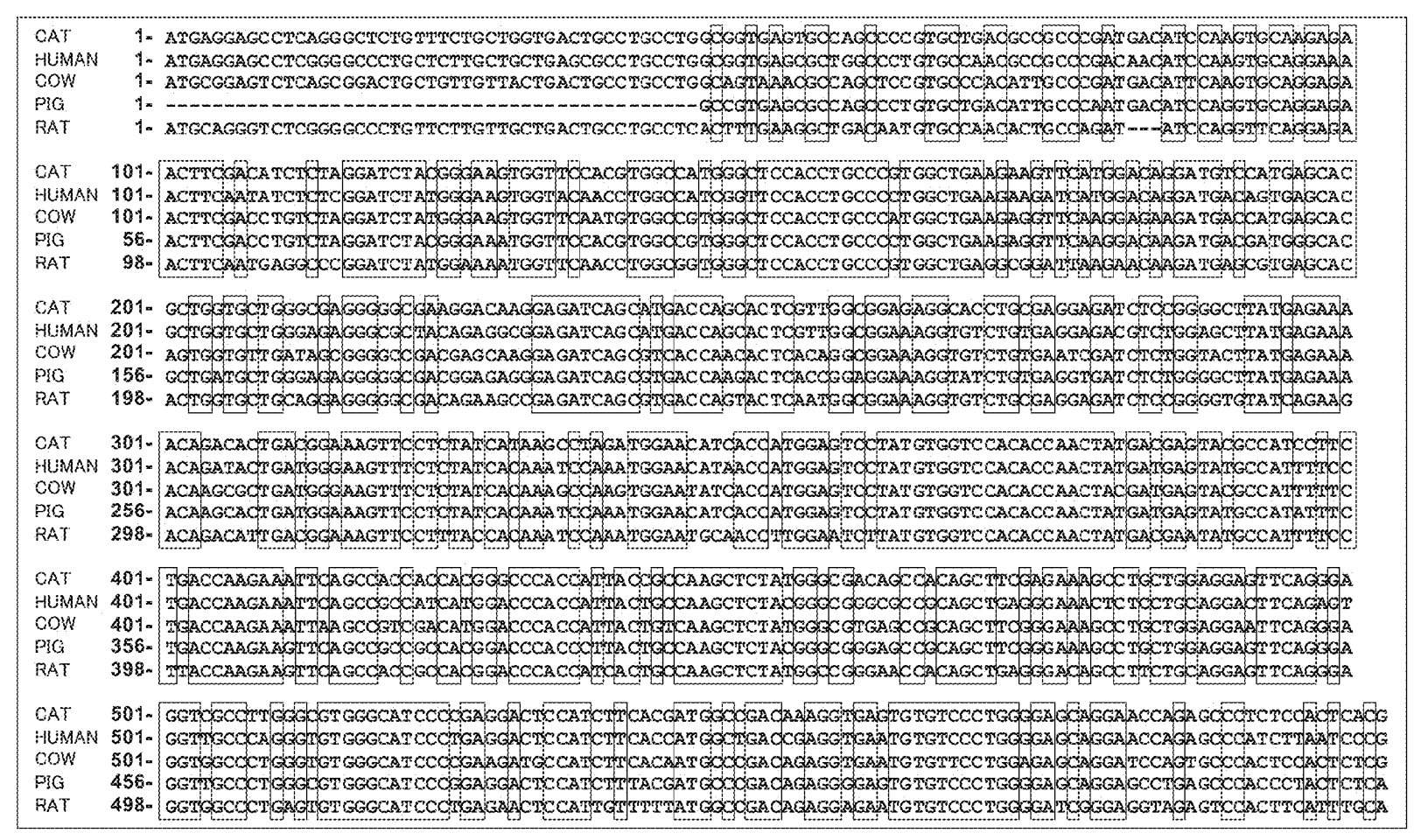

Here, FIG. 29 is a chart showing the amino acid sequence of the protein of the present invention represented by SEQ ID NO: 32 (feline $\alpha_1$-m), in comparison with known amino acid sequences of $\alpha_1$-m in human, cow, pig and rat. In FIG. 29, the part surrounded by a square indicates the amino acid sequence that is common among various animal species. The number of amino acids in the protein of the present invention represented by SEQ ID NO: 32 is 201 in the entire length, which is completely the same with the number of amino acids of 201 in human, cow and pig, and is approximate to the number of amino acids of 200 in rat. While the detail will be described later in Experimental Example 8, from the fact that the amino acid sequence of the protein of the present invention has an average homology of 76.39% with amino acid sequences of $\alpha_1$-m of other animal species, and homologies of amino acid sequence of $\alpha_1$-m among other animal species (human, cow, pig and rat) distribute in the range of 68.32 to 78.71%, the protein of the present invention is estimated as feline-derived $\alpha_1$-m.

The feline-derived $\alpha_1$-m of the present invention is preferably obtained by artificial synthesis. This time, the present inventor first found a nucleotide sequence of a structural gene ($\alpha_1$-m gene) of feline-derived $\alpha_1$-m (nucleotide sequence represented by SEQ ID NO: 33). The present invention also provides a structural gene encoding feline-derived α1 microglobulin, and this structural gene preferably has a nucleotide sequence represented by SEQ ID NO: 33. That is, the structural gene of the present invention may include another nucleotide sequence as an intron as far as it includes the nucleotide sequence represented by SEQ ID NO: 33 as an exon.

Here, FIG. 30 is a chart showing a structural gene of the present invention (feline $\alpha_1$-m gene) represented by SEQ ID NO: 33, in comparison with known nucleotide sequences of $\alpha_1$-m gene of human, cow, pig and rat. In FIG. 30, the part surrounded by a square indicates the nucleotide sequence that is common among various animal species. While nucleic acid length of $\alpha_1$-m gene was 603 bases in human and cow, and 602 bases in rat, the length of feline $\alpha_1$-m gene of the present invention represented by SEQ ID NO: 33 was 603 bases. From the fact that homology between the nucleotide sequence of feline $\alpha_1$-m gene of the present invention represented by SEQ ID NO: 33 and nucleotide sequences of $\alpha_1$-m gene of other animal species is 80.48% on average, and average homologies of nucleotide sequence of $\alpha_1$-m gene among other animal species (human, cow, pig and rat) distribute in the range of 74.30 to 80.30%, the structural gene of the present invention is estimated as feline-derived $\alpha_1$-m gene.

The present invention also provides a novel antibody that specifically binds to feline-derived $\alpha_1$-m. While the detail will be described later in Experimental Example 9, the inventor of the present invention expressed feline-derived $\alpha_1$-m from the feline-derived $\alpha_1$-m gene of the present invention as described above, and prepared a cell capable of producing an antibody against the same as an antigen. Such a cell line is novel, and the present applicant et al. deposited the cell line with International Patent Organism Depositary, National Institute of Advanced Industrial Science and Technology on Feb. 9, 2010 (Accession Nos.: FERM P-21910 and FERM P-21911).

Figure 31:
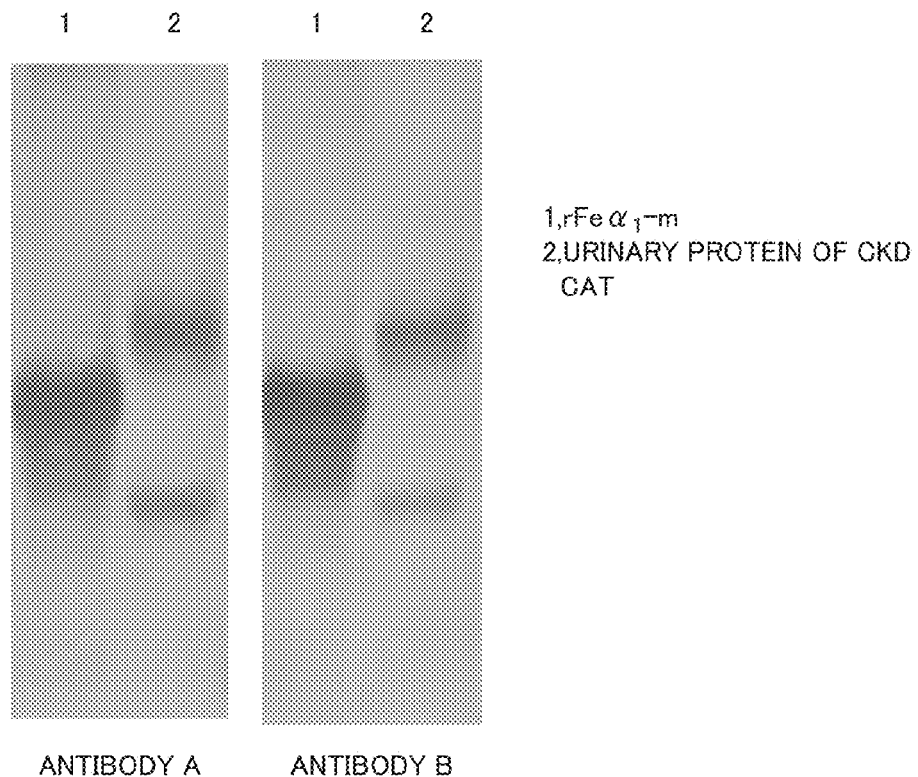
FIG. 31 is a photograph showing an experimental result of specificity of antibodies E and F to feline native $\alpha_1$-m in Experimental Example 9.

The antibody of the present invention is preferably produced by a cell line Mouse-Mouse hybridoma $\alpha_1$-m mAb1 (Accession No.: FERM P-21910) or a cell line Mouse-Mouse hybridoma $\alpha_1$-m mAb2 (Accession No.: FERM P-21911) against the protein of the present invention as described above as an antigen. Here, FIG. 31 is a photograph showing an experimental result revealing that the antibody of the present invention specifically binds to feline native $\alpha_1$-m. While the detail will be described later in Experimental Example 9, antibody E shown in FIG. 31 is a monoclonal antibody of isotype of κ chain of IgG1 produced by a cell line Mouse-Mouse hybridoma $\alpha_1$-m mAb1 (Accession No.: FERM P-21910), and antibody F is an antibody of isotype of κ chain of IgG2b produced by a cell line Mouse-Mouse hybridoma $\alpha_1$-m mAb2 (Accession No.: FERM P-21911). As shown in FIG. 31, it is recognized that the antibody of the present invention is capable of specifically binding to feline native $\alpha_1$-m.

[4] Diagnosis Kit and Diagnosis Method for Feline Nephropathy

The present invention also provides a diagnosis method and a diagnosis kit for feline nephropathy using the antibody of the present invention as described above. Since the antibody of the present invention is capable of specifically binding to CysC, $\beta_2$-m or $\alpha_1$-m which is a marker for feline nephropathy, it becomes possible to diagnose whether or not a cat suffers from nephropathy using, for example, urine of the cat as a sample, rapidly and conveniently in comparison with conventional cases. The diagnosis kit of the present invention may contain, besides the antibody of the present invention, for example, a well, a chromogenic substrate solution, a reaction stopper, a washing liquid, a standard solution and so on.

EXPERIMENTAL EXAMPLES

In the following, the present invention will be described more specifically by way of experimental examples, however, the present invention will not be limited to these examples.

Experimental Example 1

Identification of CysC Gene (1) Subject Animal

In the present experimental example, one 10-year-old male Japanese cat showing no abnormality in a blood biochemical test and a urine biochemical test, kept in an experimental animal facility was used. This cat was bred in a condition of 12 hours of day and 12 hours of night in a cage for cat, and allowed for free eating and free drinking by feeding once a day.

(2) Extraction of Total RNA from Feline Leukocytes

First, feline blood was collected from the external jugular vein of the subject animal using an EDTA blood collection tube. The collected 5 mL of blood was transferred to a conical tube, centrifuged at 3000× rpm for 5 minutes, and then a buffy coat (leukocyte layer) was separated. Then, total RNA was extracted using QIAamp RNA Blood Kit (QIAGEN) according to an attached protocol. The obtained total RNA was stored at 4° C. until use.

Then, mRNA was separated and purified from total RNA using Oligotex™-dT30 Super mRNA Purification Kit (TAKARA BIO INC.) according to an attached protocol. Concretely, first, 60 μL of total RNA was mingled with 70 μL of 2× Binding Buffer and 14 μL of Oligotex™-dT30, and then warmed at 70° C. for 3 minutes by a thermal cycler (PC801, ASTEC). After warming, hybridization between mRNA and Oligotex™-dT30 Super was allowed by leaving still at room temperature for 10 minutes. A column containing the reaction solution was centrifuged at 15700×g for 5 minutes, suspended in 350 μL of Wash Buffer, then transferred to a cup of an attached spin column set, centrifuged at 15700×g for 30 seconds, again suspended in 350 μL of Wash Buffer, and then centrifuged at 15700×g for 30 seconds. Oligotex™-dT30 in the column was suspended in 30 μL of RNase free $H_2O$ warmed in advance to 70° C., and mRNA was eluted by using an attached new centrifugal tube for spin column. This operation was repeated twice, and the obtained solution was regarded as a mRNA solution.

Then, using the obtained mRNA solution and first-strand cDNA Synthesis Kit (GE Healthcare Bio Science), first-strand cDNA was prepared according to an attached protocol. Concretely, first, 30 μL of mRNA was warmed at 65° C. for 10 minutes by a thermal cycler, and then rapidly cooled on ice for 2 minutes. Then, 11 μL of a Bulk first-strand reaction-mix, 1 μL of a DTT Solution and 1 μL of random hexamer were added. The resultant solution was warmed at 37° C. for 1 hour by a thermal cycler, and the obtained solution was regarded as first-strand cDNA.

(3) Determination of Nucleotide Sequence of Intermediate Region of Feline-Derived CysC Gene On the basis of the nucleotide sequence of the region that is highly conserved among revealed nucleotide sequences of mRNA of animal species, specific primers for feline-derived CysC gene having the following nucleotide sequences were designed.

```
Upstream primer 1:
                                     (SEQ ID NO: 3)
5'-SGWSRGCGATWCAACAAR-3'

Downstream primer 1:
                                     (SEQ ID NO: 4)
5'-CTGRCAGSTGGAYTTCRM-3'
```

In the aforementioned nucleotide sequences, S represents G or C, W represents A or T, R represents A or G, Y represents C or T, and M represents A or C.

Using Upstream primer 1 and Downstream primer 1 designed in this manner, the first-strand cDNA was amplified by PCR. Here, FIG. 4 is an electrophoretic photograph of a result of PCR of the first-strand cDNA. After confirming a band appeared near the theoretical length of the PCR product by agarose electrophoresis, the annealing temperature was adjusted to 60° C. which is an ideal condition, and a single band as shown in FIG. 4 was obtained. The single band obtained by electrophoresis was cut out from the agarose gel, and DNA was extracted. DNA extraction was conducted using QIAquick Gel Extraction Kit (QIAGEN) according to an attached protocol. For the cutout DNA band, weight of gel was measured, and 3-times equivalent amount of QG buffer was added, and the resultant was warmed in a thermostat (TR-2A, ASONE) of 50° C. for 10 minutes, to completely dissolve the gel, and then isopropanol of an equivalent amount to the gel was added and mingled well. The DNA solution was added to a 2 mL collection tube equipped with a column attached to the kit, and centrifuged at room temperature at 13400×g for 1 minute. Then, after removing the filtrate in the collection tube, the column was again added with 0.75 mL of PE buffer, and washed at room temperature by centrifugation at 15700×g for 1 minute, and then the filtrate was removed, and further centrifuged for 1 minute. Then, the column was set in a new 1.5 mL microtube, added with 50 μL of EB buffer, left still at room temperature for 1 minute, and an extraction liquid was collected by centrifugation at 15700×g for 1 minute.

Then, the obtained DNA was treated using TOPO TA Cloning Kit (Invitrogen) and pGEM-T Easy Vector System (Promega) according to an attached protocol. Concretely, first, 3 μL of the stored PCR product, 1 μL of pGEM-T Easy Vector, 1 μL of T4 DNA Ligase (3 Weiss units/μL), and 2× Rapid Ligation Buffer, 5 μL of T4 DNA Ligase were mingled in a 500 μL Eppendorf tube, and incubated at 4° C. overnight to cause ligation. The obtained reaction liquid was further transformed into E. coli. 2.5 μL of the ligation reaction liquid was added to E. coli JM109 Competent cells (TAKARA BIO INC.), left still on ice, and then subjected to Heat Shock in a thermostat of 42° C. for 45 seconds, and then rapidly cooled for 2 minutes. Further, the reaction liquid was gently added with 450 μL of a SOC medium (2% Tryptone, 0.5% Yeast Extract, 10 mM NaCl, 2.5 mM KCl, 10 mM $MgCl_2$, 10 mM $MgSO_4$, 20 mM glucose), and shake-cultured at 37° C. for 90 minutes at a rate of 150 rpm in a shake incubator (PERSONA-11, TAITEC). Each 100 μL of E. coli suspension after culture was uniformly spread by a bacteria spreader on a LB agar plate medium (TAKARA BIO INC.) applied with 20 μL of 20 mg/mL X-gal (TAKARA BIO INC.) dissolved in DMSO and 1004 of 100 mM Isopropyl-β-D-thiogalactopyranoside (IPTG), and cultured at 37° C. using an incubator (IS62, TAITEC). After 18 hours, only a white colony was picked up with a sterilized toothpick, and inoculated in 3 mL of a LB liquid medium supplemented with 5 mg/mL of ampicillin, and cultured at 37° C. for 24 hours. After culture, plasmid of E. coli was extracted by using QIAPrep Spin Mini Kit 50 (QIAGEN) according to an attached protocol. The obtained plasmid was treated with a restriction enzyme (EcoRI), and then whether ligation occurred was determined by agarose gel electrophoresis. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 5) of about 260 bases.

Figure 5:
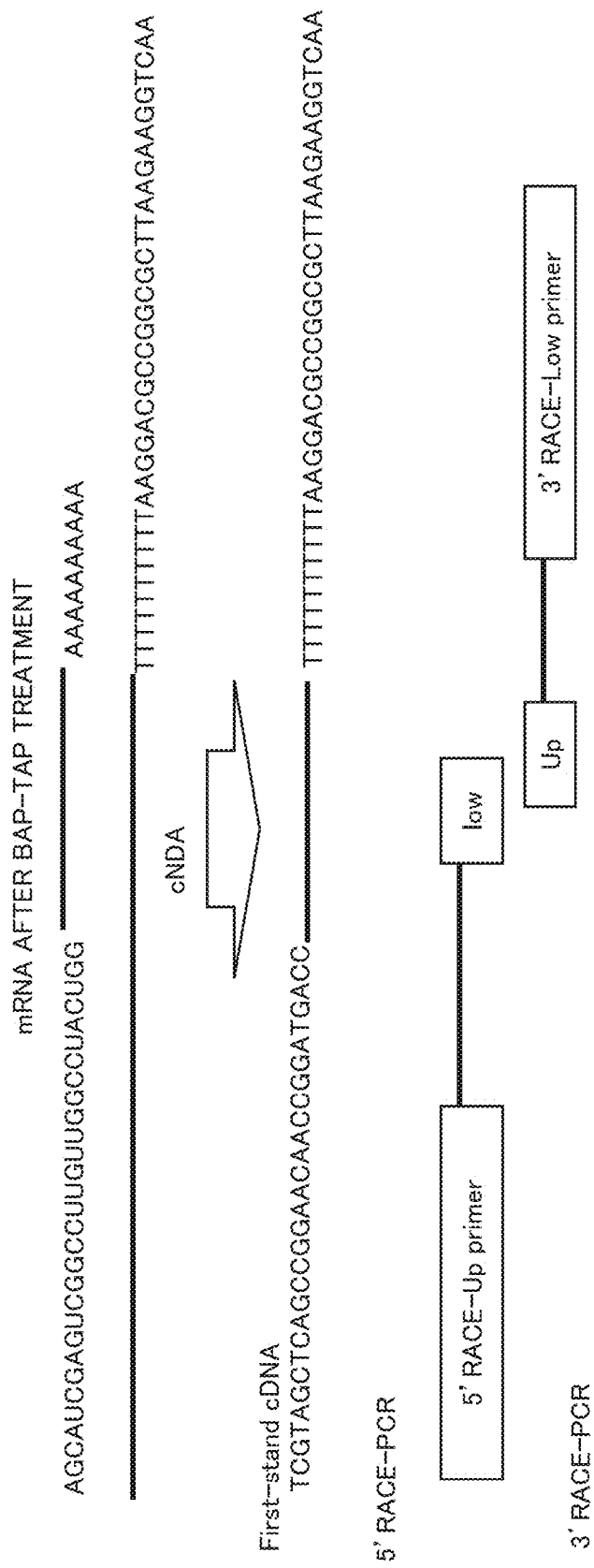
FIG. 5 is an illustration schematically showing a positional relationship between double-stranded DNA synthesizable by a kit used in Experimental Example 1 and primers.

(4) Preparation of Full-Length mRNA Using Oligo-Capping Method 1 to 5 µg of mRNA separated from feline leukocytes by the aforementioned method was mingled in BAP buffer containing 40 U of RNasin Ribonuclease Inhibitor (Promega) and 0.5 U of Bacterial Alkarine Phosphatase (BAP: TAKARA BIO INC.), and allowed to react at 37° C. for 60 minutes. After enzyme reaction, the BAP-treated mRNA solution was subjected to phenol/chloroform extraction, and caused to precipitate by using Ethachinmate (WAKO). The BAP-treated mRNA was further mingled with 60 U of RNasin, 8.0 U of Tobacco Acid Pyrophosphatase (TAP: WAKO) and a TAP buffer, and allowed to react at 37° C. for 60 minutes. After end of the enzyme reaction, the BAP-TAP-treated mRNA solution was subjected to phenol/chloroform extraction, and concentrated by using Ethachinmate. The BAP-TAP-treated mRNA was added with 100 ng of synthesized Oligo-RNA (5'-AGCAUCGAGUCGGCCUUGUUGGCCUACUGG-3': SEQ ID NO: 6), allowed to react at 65° C. for 5 minutes, and then mingled with a ligation buffer containing 40 U of RNasin and 50 U of T4 RNA ligase (TAKARA BIO INC.), and allowed to react at 20° C. for 3 hours. After end of the enzyme reaction, the mRNA solution treated with RNA ligation was subjected to phenol/chloroform extraction, and concentrated by using Ethachinmate (WAKO), and then mingled with DNase buffer containing 40 U of RNasin and 10 U of RNase Free DNase I (TAKARA BIO INC.) and allowed to react at 37° C. for 10 minutes. After end of the enzyme reaction, the obtained mRNA solution was subjected to phenol/chloroform extraction, and concentrated by Ethachinmate (WAKO), and first-strand DNA was synthesized at 42° C. for 60 minutes using first-strand cDNA Synthesis Kit (GE Healthcare Bio Science) according to an attached protocol, by using 5'-AACTGGAAGAATTCGCGGCCGCAGGAAT$_{18}$-3' (SEQ ID NO: 7) as an oligo (dT)Primer and adding AMV Reverse transcriptase, and a first-strand buffer (FIG. 5).

(5) 5'RACE-PCR Method

The dsDNA prepared in the manner as described above was amplified by a 5'RACE-PCR method. The primers used in 5'RACE-PCR method were designed to respectively have the following nucleotide sequences based on the sequence of the added RNA adaptor for the upstream primer, and based on the nucleotide sequence of the intermediate region already determined for the downstream primer.

```
5'RACE-upstream primer:
                                    (SEQ ID NO: 8)
5'-AGCATCGAGTCGGCCTTGTTG-3'

5'RACE-downstream primer:
                                    (SEQ ID NO: 9)
5'-TTCATCCCAGCCACGACCTGCTTTC-3'
```

Figure 6:
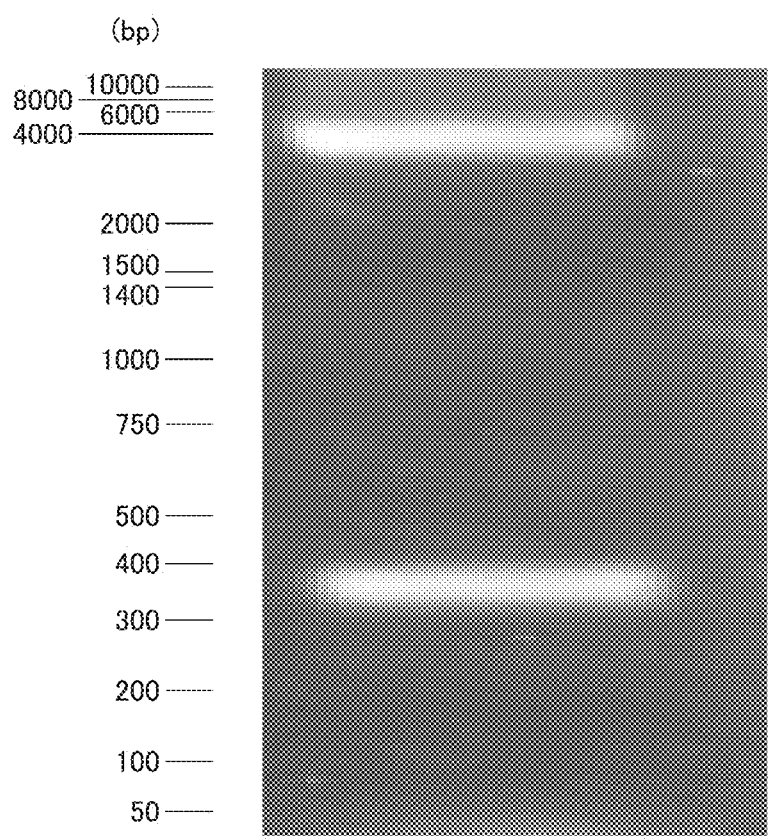
FIG. 6 is an electrophoretic photograph showing a result of 5'RACE-PCR in Experimental Example 1.

Using the primers designed in this manner, PCR was conducted in the condition of 1 cycle of 2 minutes at 95° C., 30 cycles of 1 minute at 95° C., 1 minute at 60° C. and 1 minute at 72° C., and 1 cycle of 10 minutes at 72° C. FIG. 6 is an electrophoretic photograph showing a result of 5'RACE-PCR, and the obtained PCR product was confirmed as two bands as shown in FIG. 6. DNA was extracted from the PCR product using QIAquick Gel Extraction Kit (QIAGEN), and PCR was conducted again, and then ligation and transformation were conducted using TOPO TA Cloning Kit (Invitrogen), pGEM-T Easy Vector System (Promega) and E. coli JM109 Competent cells (TAKARA BIO INC.). From E. coli JM109 after culture, plasmid was extracted using QIAPrep Spin Mini Kit 50 (QIAGEN), and the obtained plasmid was treated with a restriction enzyme (EcoRI), and then insertion of DNA fragment was confirmed by agarose gel electrophoresis. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 10) of about 350 bases.

(6) 3'RACE-PCR Method

The dsDNA prepared in the manner as described above was amplified by a 3'RACE-PCR method. The primers used in the 3'RACE-PCR method were designed to respectively have the following nucleotide sequences based on the nucleotide sequence of the intermediate region already determined for the upstream primer and based on the sequence of the DNA adaptor added to 3' end for the downstream primer.

```
3'RACE-upstream primer:
                                    (SEQ ID NO: 11)
5'-GCTCTTTCCAGATATACACTGTACCCT-3'

3'RACE-downstream primer:
                                    (SEQ ID NO: 12)
5'-AGAATTCGCGGCCGCAGGAATT-3'
```

Figure 7:
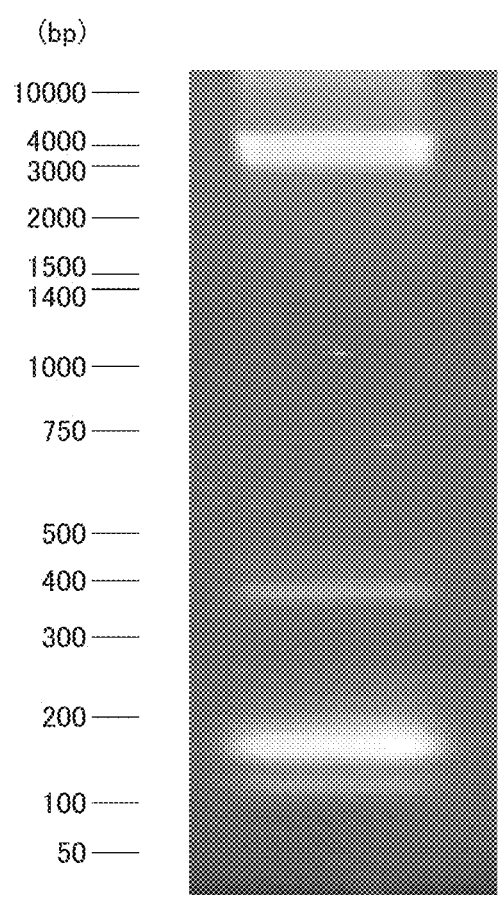
FIG. 7 is an electrophoretic photograph showing a result of 3'RACE-PCR in Experimental Example 1.

Using the primer designed in this manner, PCR was conducted in the condition of 1 cycle of 2 minutes at 95° C., 30 cycles of 1 minute at 95° C., 1 minute at 55° C. and 1 minute at 72° C., and 1 cycle of 10 minutes at 72° C. FIG. 7 is an electrophoretic photograph showing a result of 3'RACE-PCR, and the obtained PCR product was confirmed as a completely single band as shown in FIG. 7. For the obtained PCR product, ligation and transformation were conducted using TOPO TA Cloning Kit (Invitrogen), pGEM-T Easy Vector System (Promega) and E. coli JM109 Competent cells (TAKARA BIO INC.). From E. coli JM109 after culture, plasmid was extracted using QIAPrep Spin Mini Kit 50 (QIAGEN), and the obtained plasmid was treated with a restriction enzyme (EcoRI), and then insertion of DNA fragment was confirmed by agarose gel electrophoresis. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 13) of about 390 bases.

(7) Analysis of Nucleotide Sequence in the Entirety of Obtained cDNA

Based on the nucleotide sequences obtained in the above, an entire sequence (SEQ ID NO: 14) was constructed. The sequence of nucleic acid of the full length represented by SEQ ID NO: 14 had 796 bases, and encoded CysC therein. In the nucleotide sequence represented by SEQ ID NO: 14, it was revealed that the 59th to 502nd bases constitute a structural gene encoding CysC (CysC gene: SEQ ID NO: 2).

FIG. 2 is a chart showing the obtained nucleotide sequence of cDNA of feline CysC gene, in comparison with known nucleotide sequences of CysC genes of human, monkey, cow, pig and rat. In the chart, the part of the nucleotide sequence that is common is indicated by a surrounding square. While nucleic acid length of CysC gene was 441 bases in human, monkey and pig, 447 bases in cow, and 423 bases in rat, nucleic acid length of CysC gene was 444 bases in feline CysC gene obtained herein. Also, as shown in Table 1, while homologies of nucleotide sequences of CysC genes among other animal species (human, monkey, cow, pig and rat) distributed in the range of 67.21 to 96.71%, homology between the nucleotide sequence of the feline CysC gene obtained herein and nucleotide sequences of CysC genes of other animal species was 77.69% on average, and it was revealed that the obtained nucleotide sequence was feline CysC gene.

TABLE 1

|        | Rat    | Pig    | Cow    | Monkey | Human  | Average |
|--------|--------|--------|--------|--------|--------|---------|
| Cat    | 73.55% | 81.18% | 78.20% | 77.88% | 77.65% | 77.69%  |
| Human  | 69.30% | 76.10% | 73.27% | 96.71% |        |         |
| Monkey | 68.69% | 76.32% | 73.27% |        |        |         |
| Cow    | 67.21% | 83.00% |        |        |        |         |
| Pig    | 68.29% |        |        |        |        |         |

Experimental Example 2

Synthesis of Feline-Derived CysC (1) Analysis of Amino Acid Sequence of Feline-Derived Cysc The nucleotide sequence (SEQ ID NO: 2) of feline-derived CysC gene obtained in Experimental Example 1 was translated into an amino acid sequence, and the amino acid sequence (SEQ ID NO: 1) of feline-derived CysC was analyzed. FIG. 1 is a chart showing the obtained amino acid sequence of feline CysC, in comparison with the known amino acid sequences of CysC of human, monkey, cow, pig and rat. In the chart, the part of the amino acid sequence that is common is indicated by a surrounding square. As a result, the number of amino acids in feline-derived CysC was 147 in the entire length, and the number of amino acids in human, monkey and pig was 146, and the number of amino acids in cow was 148, and the number was approximate to the number of amino acids of 140 in rat. The position and number of structural amino acid cysteine conserved among other animal species were also similar. As shown in Table 2, regarding homology, while homologies of amino acid sequences of CysC among other animal species (human, cow, pig and rat) distributed in the range of 62.22 to 97.26%, average homology between the amino acid sequence of the feline CysC obtained herein and those of other animal species was 69.15%. Therefore, it was revealed that the obtained amino acid sequence was feline-derived CysC.

TABLE 2

|        | Rat    | Pig    | Cow    | Monkey | Human  | Average |
|--------|--------|--------|--------|--------|--------|---------|
| Cat    | 65.44% | 76.03% | 68.92% | 68.03% | 67.35% | 69.15%  |
| Human  | 70.55% | 63.45% | 63.51% | 97.26% |        |         |
| Monkey | 70.55% | 65.52% | 64.19% |        |        |         |
| Cow    | 63.50% | 75.00% |        |        |        |         |
| Pig    | 62.22% |        |        |        |        |         |

(2) Expression and Purification of Recombinant Protein Using GST Fusion Protein

In order to amplify nucleic acids for the feline-derived CysC protein region excluding the part of putative signal peptide region, PCR was conducted. Primers were designed to respectively have the following nucleotide sequences by adding a restriction enzyme site of EcoRI to 5' end for an upstream primer and adding a restriction enzyme site of XhoI to 3' end for a downstream primer.

```
Upstream primer:
                                   (SEQ ID NO: 15)
5'-CACGAATTCACCGGCAGGAGAAACAACAAG-3'

Downstream primer:
                                   (SEQ ID NO: 16)
5'-CACCTCGAGTTATGCATCCTGGCAGCTGGACTTCACCAG-3'
```

Using the upstream primer and the downstream primer as described above, PCR was conducted in the condition of 1 cycle of 2 minutes at 95° C., 30 cycles of 1 minute at 95° C., 1 minute at 75° C. and 1 minute at 72° C., and 1 cycle of 10 minutes at 72° C. After subjecting the PCR product to agarose gel electrophoresis, DNA was extracted from the agarose gel. After mixing equivalent amounts of the DNA extraction solution and phenol, centrifugation at 15700×g was conducted for 5 minutes, and then an aqueous layer containing nucleic acid was separated. The separated aqueous layer was mixed with the equivalent amount of chloroform, and centrifuged at 15700×g for 5 minutes, and then the supernatant was separated. Then, the solution after separation was added with 2.5-times equivalent amount of 100% ethanol, left still at −80° C. for 30 minutes, and then centrifuged at 15700×g for 5 minutes, and then the supernatant was removed, to obtain a sediment. The sediment was added with 70% ethanol, centrifuged at 15700×g for 5 minutes, and then the supernatant was removed, to obtain a concentrated sample of the PCR product. The concentrated sample of the PCR product was mingled with 5 μL of EcoRI (TAKARA BIO INC.), 5 μL of XhoI (TAKARA BIO INC.), 5 μL of H. Buffer (500 mM Tris-HCl, pH 7.5, 100 mM $MgCl_2$, 10 mM Dithiothreitol, 1000 mM NaCl) and 35 μL of RNase free $H_2O$. Also, 5 μL (2.5 μg) of pGEX6P-1 (GE Healthcare Bio Science) was mingled with 5 μL of EcoRI, 5 μL of XhoI, 5 μL of H. Buffer and 30 μL of RNase free $H_2O$. After treating each solution with the restriction enzymes by incubation at 37° C. overnight, agarose gel electrophoresis was conducted, and each DNA band was extracted by using QIAquick Gel Extraction Kit (QIAGEN). Ligation was conducted using DNA Ligation Kit (TAKARA BIO INC.). To be more specific, 5 μL of Ligation Mix, 1 μL of cDNA solution of CysC treated with restriction enzymes and 4 μL of pGEX6P-1 were mingled, and left still at 16° C. overnight, and thus, a plasmid vector (pGEX-CysC) ligated with cDNA of CysC was created. Further, 2.5 μL of this pGEX-CysC solution was added to 25 μL of *E. coli* JM109 Competent Cells (TAKARA BIO INC.), left still on ice for 30 minutes, and subjected to Heat shock in a thermostat of 42° C. for 45 seconds, and immediately cooled on ice for 2 minutes, and then gently added with 250 μL of a SOC medium (2% Tryptone, 0.5% Yeast extract, 10 mM NaCl, 2.5 mM KCl, 10 mM $MgSO_4$, 10 mM $MgCl_2$, 20 mM Glucose) and kept at 37° C. for 1 hour. 100 μL of *E. coli* solution transfected with pGEX-CysC was applied on a LB medium supplemented with ampicillin, and left still at 37° C. overnight, and then a colony was picked up, and mingled with 1.2 mL of a LB liquid medium supplemented with ampicillin and cultured at 37° C. overnight. The liquid medium after culture was centrifuged at 13400×g for 1 minute, and then the supernatant was completely removed, and from the obtained sediment, pGEX-CysC was extracted using QIAPrep Spin Mini Kit (QIAGEN). This pGEX-CysC was confirmed by an agarose gel electrophoresis method. Whether subcloning of pGEX-CysC was succeeded or not was determined by using Dye Deoxy Terminator Cycle Sequencing Kit (Applied Biosystems) using T7 primer and nucleotide sequence analysis using Applied Biosystems 3130xl Genetic Analyzer (Applied Biosystems).

(3) Confirmation of Expression of GST Fusion Protein

*E. coli* transfected with pGEX-CysC was cultured at 37° C. overnight in a LB medium, and then 100 μL of the culture was mingled with 20 μL of Isopropyl-β-D-thiogalactopyranoside (IPTG: 0.1 mM), and shake-cultured (BR40-LF, TAITEC) at 30° C. for about 2 hours. The *E. coli* solution after the shake culture was centrifuged at 15700×g for 1 minute, and then the supernatant was removed, and the sediment was added with 30 μL of a solubilizing agent (50 μL of 50 mM Tris-HCl, 100 μL of 1×RIPA Lysis Buffer (Up State), 140 μL of Protease Inhibitor, 710 μL of $H_2O$) to be solubilized, and then centrifugation at 15700×g for 5 minutes was conducted to separate the mixture into a supernatant and a sediment. 30 μL of the supernatant was added with 30 μL of 2×SB solution (2% SDS, 40% Glycerol, 0.6% BPB, 25 mM Tris-HCl Buffer (pH 6.8, 20° C.)) and 1 μL of 2ME, and the mixture was warmed at 95° C. for 3 minutes. The sediment was added with 20 μL of SB solution, and crushed for 5 seconds by an ultrasonic crusher (UR-20P, TOMY SEIKO CO, LTD), and then warmed at 95° C. for 3 minutes. Then, for the supernatant and the sediment, expression of GST fusion protein and solubility of GST fusion protein in *E. coli* were confirmed by SDS-PAGE.

(4) SDS-PAGE Method

SDS-PAGE was conducted using a compact PAGE (AE-7300, ATTO) according to a method of Laemmli with modification as shown below. To be more specific, a separation gel was composed of 15% Acrylamide, 0.2% N,N-Methylene-bis-Acrylamide, 0.1% SDS, and 375 mM Tris-HCl buffer (pH 8.8, 20° C.). Gel was prepared by using a 2/4 gel cast (AE-7344, ATTO). An electrode buffer was composed of 0.1% SDS, 129 mM Glycine, and 25 mM Tris (pH 8.3, 20° C.). A sample for loading (SB) was composed of 1% SDS, 20% Glycerol, 0.3% BPB, and 12.5 mM Tris-HCl Buffer (pH 6.8, 20° C.). As a marker, pre-stained SDS-PAGE standard (Broad) marker (BIO-RAD) or SDS-PAGE standard (Broad) marker (BIO-RAD) was used. Electrophoresis was conducted for 30 minutes in a Tris-Gly/PAGE High mode, and then changed into a Tris-Gly/PAGE Low mode, and stopped when the lower ion interface migrates to the position of 1 to 2 mm above the lower end of the gel. For the gel after end of SDS-PAGE, a silver staining method according to an Oakley method was conducted. Concretely, the gel was immobilized in a solution of 30% ethanol and 10% acetic acid, and then washed, and dipped twice in 20% ethanol for 5 minutes. After removal of 20% ethanol, the gel was reacted with a 5% glutaraldehyde solution for 4 minutes, washed with pure water, and then dipped twice in 20% ethanol for 4 minutes. Thereafter, the gel was washed with pure water, reacted with an ammonical silver nitrate solution for 5 minutes, washed with pure water, and then caused to color by a solution of 0.005% citric acid and 0.019% formaldehyde. The gel for which coloring was confirmed was immobilized in a solution of 20% ethanol and 10% acetic acid for 5 minutes, and dipped twice in 20% ethanol for 5 minutes, and then photographed. The silver staining method was conducted entirely in a light-shielded condition.

(5) Expression Induction and Isolation of GST Fusion Protein

Figure 8:
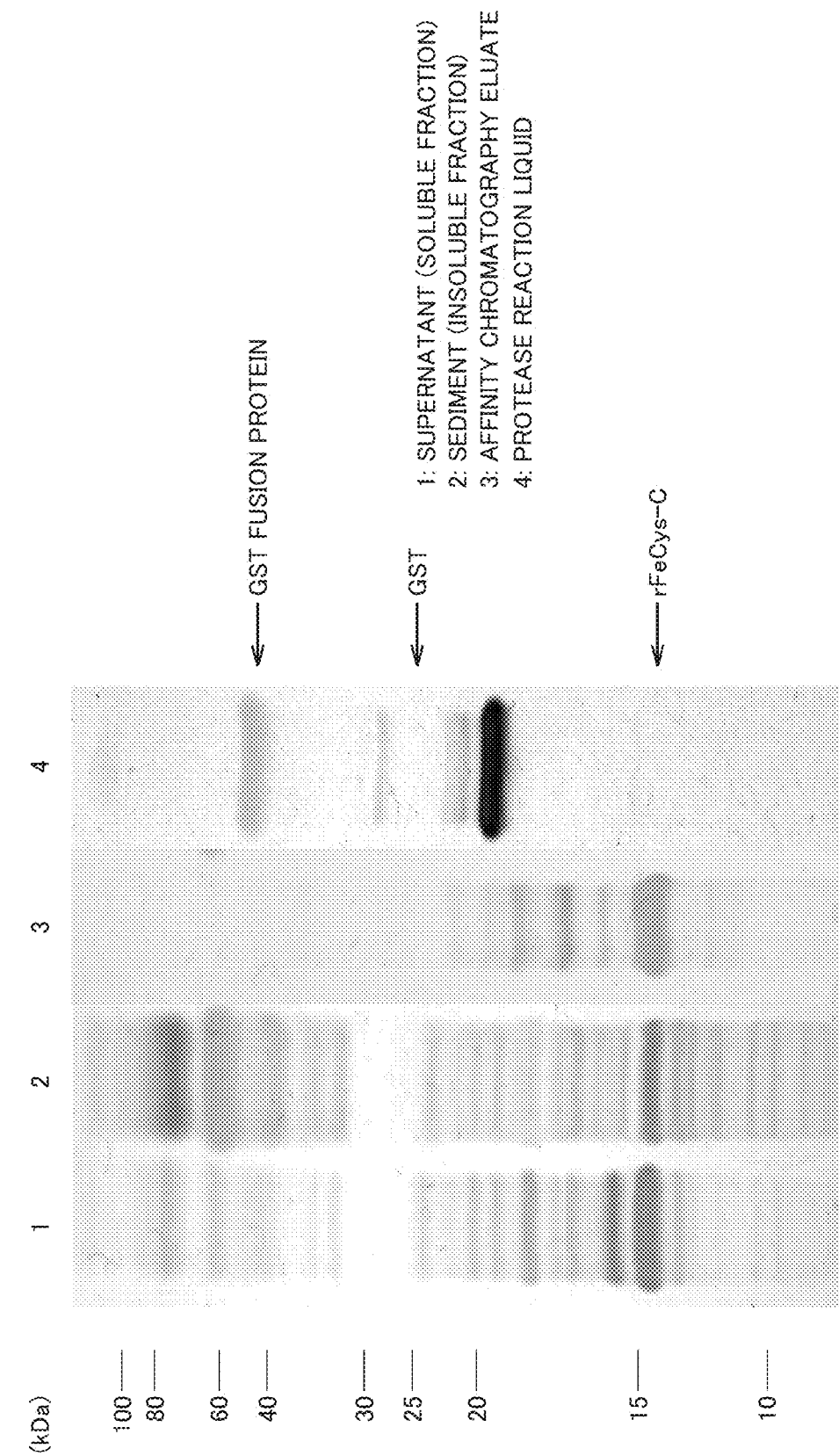
FIG. 8 is a photograph showing a result of SDS-PAGE after expression of GST fusion protein in Experimental Example 2.

*E. coli* in which expression of GST fusion protein with His-Tag was confirmed was applied on a LB agar medium supplemented with ampicillin, and a colony was picked up and added into 3 mL of a LB liquid medium supplemented with ampicillin and shake-cultured at 37° C. overnight. Sequentially, 3 mL of the culture liquid was added into 250 mL of a LB liquid medium supplemented with ampicillin, and shake-cultured at 37° C. for about 150 minutes, and then added with 2.5 mL of 0.1 mM IPTG, and shake-cultured at 30° C. for about 2 hours. The culture liquid after induction of GST fusion protein expression was centrifuged at 6000×g for 15 minutes, and the resultant sediment was suspended in Phosphate buffer saline (PBS: 140 mM NaCl, 2.7 mM KCl, 10 mM $Na_2PO_4$, 1.8 mM $KH_2PO_4$, pH 7.3), and crushed for 20 seconds 5 times by an ultrasonic crusher, and added with Triton X100 in a final concentration of 1%, and left still at room temperature for 30 minutes under stirring, and then centrifuged at 9300×g for 20 minutes, and the supernatant and the sediment were analyzed by SDS-PAGE. As a result of electrophoresis, GST fusion protein was contained both in the supernatant fraction and in the sediment fraction, however, for affinity chromatography, the supernatant was used because a soluble fraction is more convenient (FIG. 8).

(6) Affinity Chromatography Method

For the supernatant obtained in the manner as described above, affinity chromatography was conducted using GSTrap HP column (GE Healthcare Bio Science). After dialysis against PBS which is a binding buffer, the supernatant was added to a column and washed well with the binding buffer, and eluted with 50 mM Tris-HCl (pH 8.0) supplemented with 10 mM reduced glutathione. For column operation, addition was made at a flow rate of 0.5 mL/min using a peristaltic pump (SJ-1211L, ATTO). Absorbance of the eluate was monitored at an absorption wavelength of 220 nm by using a UV region absorbance monitor (AC-5100L, ATTO), and recorded by a recorder (R-01A, RIKADENKI). In an SDS-PAGE image of the eluate, a plurality of bands including GST fusion protein as a main band were confirmed as shown in FIG. 8. 2 mL of the obtained GST fusion protein eluate was added with DTT in a concentration of 1 mM and mingled, and then put into a dialysis membrane for cutting at a molecular weight of 13 kDa (UC30-32-100, Sanko Junyaku Co., Ltd.) and dialyzed against 2 L of 50 mM Tris-HCl (pH 7.5) supplemented with 150 mM NaCl and 1 mM EDTA for about 6 hours. For the eluate of GST fusion protein after dialysis, after protein quantification using DC Protein Assay (Bio-Rad), 1 μL of PreScission Protease (GE Healthcare Bio Science) was added per 200 μg of protein quantity and mingled, and the mixture was reacted at 4° C. for 6 hours or longer. In an SDS-PAGE image after enzymatic cleavage, cleaved GST and feline recombinant CysC (rFeCysC) were confirmed. Further, this solution was used as a sample for high performance liquid chromatography (HPLC).

(7) HPLC Method

Figure 9:
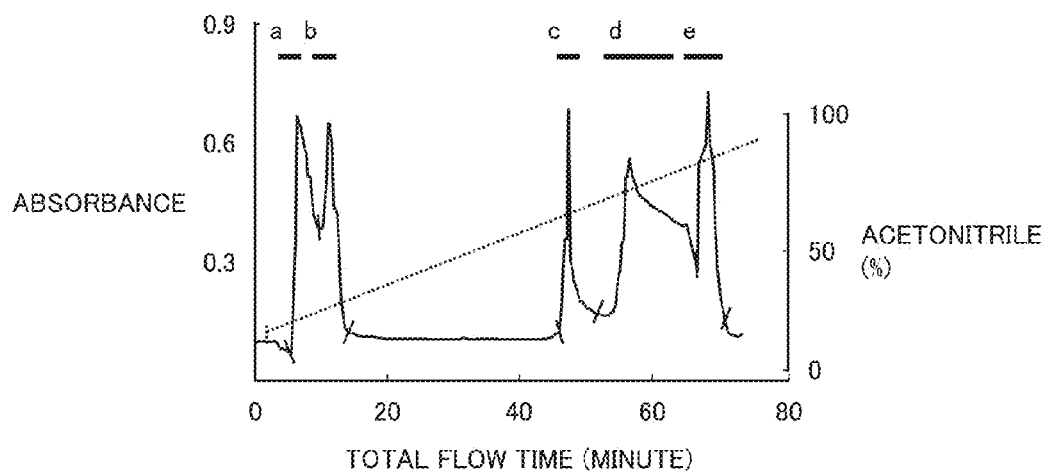
FIG. 9 is a graph showing a chromatographic pattern obtained as a result of HPLC in Experimental Example 2, wherein the left vertical axis represents absorbance at a wavelength of 220 nm, the right vertical axis represents acetonitrile concentration (%), and the horizontal axis represents time (minute).
Figure 10:
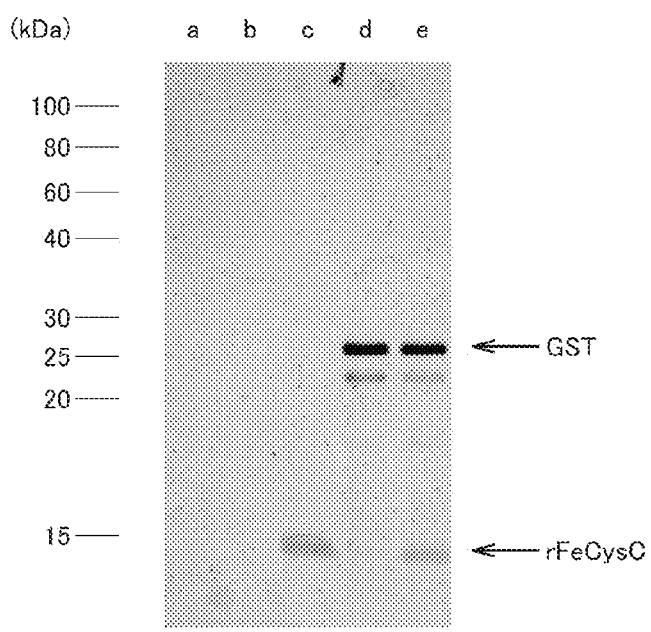
FIG. 10 is a photograph showing a result of SDS-PAGE for major fractions a, b, c, d and e of HPLC in Experimental Example 2.

An HPLC system consists of a system controller (SCL-10A VP, Shimadzu), a liquid sending unit (LC-10AD VP, Shimadzu), a UV region spectrophotometer (SPD-10A VP, Shimadzu), a column oven (CTO-10A VP, Shimadzu) and a deaeration unit (DGU-14A, Shimadzu), and as a column, MightysilRP-18 GP250-4.6 (KANTO CHEMICAL CO., INC) was used. As a separation condition of HPLC, a flow rate of mobile phase of 1 mL/min, and a sample addition amount of 400 μL were used, and for a column equilibrated with a 0.1% trifluoroacetic acid (TFA) solution, a liner gradient of 0 to 80% of acetonitrile concentration was applied using an acetonitrile solution supplemented with 0.1% TFA. The eluate was monitored by its absorbance at an absorption wavelength of 220 nm, and a detected peak was fractionated and centrifuged by a centrifugal concentrator (CC-181, TOMY) for 1 hour, and then dried in a lyophilizer (FDU-540, EYELA) and then stored at −20° C. The chromatography pattern is as shown in FIG. 9, and is generally separated into five peaks a, b, c, d and e, and protein compositions of respective eluted fractions were analyzed by an SDS-PAGE method. FIG. 10 is a photograph showing a result of SDS-PAGE for major fractions a, b, c, d and e of HPLC. As a result of analysis, as shown in FIG. 10, the target protein was eluted singly in the fraction c.

Experimental Example 3

Preparation of Antibody-Producing Hybridoma, and Anti-rFeCysC Antibody

For preparing a monoclonal antibody against the protein synthesized in Experimental Example 2 as an antigen of recombinant feline CysC (rFeCysC), first, an antibody-producing hybridoma was prepared.
(1) Preparation of Antibody-Producing Hybridoma
(1-1) Immunological Method
An immunological method was conducted by subcutaneous injection of purified rFeCysC as an antigen on a hindlimb footpad of Balb/c mouse. Immunization was conducted 4 times every 5 days, and first to third immunizations were conducted using 200 μL (50 μg/foot) of an antigen liquid that was prepared by mixing equivalent amounts of 100 μL (1 mg/mL) of an antigen solution and an adjuvant, and emulsifying the same, and the last immunization was conducted using only 20 μL (10 μg/foot) of an antigen solution. As the adjuvant, Adjuvant Complete Freund (Wako Pure Chemical Industries, Ltd.) was used in the first immunization, and Adjuvant Incomplete Freund (Wako Pure Chemical Industries, Ltd.) was used in the second to third immunizations.
(1-2) Cell Fusion
After 3 days from the last immunization, a popliteal lymph node was extracted, and after collection of lymphocytes, cell fusion was conducted using GenomONE-CF (ISHIHARA SANGYO KAISHA, LTD.). As a myeloma cell, P3X63-Ag8.653 (Dainippon Sumitomo Pharma Co., Ltd.) was used. A fusion method was conducted according to an attached protocol. Concretely, first, lymphocytes and myeloma cells were mixed at a cell number ratio of 5:1, and centrifuged at 1000 rpm and 4° C. for 5 minutes, and then the supernatant was removed. Then an ice-cooled buffer for fusion was added in an amount of 1 mL per $10^8$ cells of lymphocytes, and suspended uniformly, and then an ice-cooled HVJ-Envelope suspension was added in an amount of 25 μL per 1 mL of the cell mixture. After leaving the cell suspension on ice for 5 minutes, centrifugation at 1000 rpm and 4° C. was conducted for 5 minutes, and the resultant was incubated at 37° C. for 15 minutes in the condition that the supernatant was not removed and the cells were pelletized.

After end of the incubation, a growth medium warmed at 37° C. was added in an amount of 50 mL per $10^8$ cells of lymphocytes, and after suspending, a 96-well plate (96 Well Cell Culture Plate: Greiner bio-one) was seeded with the same in an amount of 100 μL/well. As the growth medium, RPMI1640 (Invitrogen) supplemented with 100,000 IU/mL of penicillin G (PG; Meiji Seika Pharma Co., Ltd.), 100 mg/mL of streptomycin (SM; Meiji Seika Pharma Co., Ltd.), 7.5% Briclone (IL-6, human, BriClone; Cat. No. BR-001, Dainippon Sumitomo Pharma Co., Ltd.), and 10% inactivated fetal bovine serum (FBS; NICHIREI CORPORATION) was used, and operations at the time of addition and suspending were conducted gently. After culturing for 24 hours, the culture medium was replaced with a HAT medium prepared by adding 2% HAT (Invitrogen) to the growth medium as described above.
(2) Screening of Antibody-Producing Hybridoma
For the obtained hybridoma, primary screening using an ELISA method was conducted after 1 week from the cell fusion, and only hybridoma in the well determined as reaction positive as a result of the screening was confirmed by secondary screening using a Western blotting method.
(2-1) Primary Screening
By the ELISA method using rFeCysC as an antigen, primary screening of an antibody-producing hybridoma was conducted. As an ELISA plate, a 96 Well ELISA
Microplate (Greiner bio-one) was used. For washing of the plate, an automated washing machine (Auto Mini Washer AMW-8, BIOTEC Co., Ltd.) was used, and as a washing liquid, PBS (1.37 M NaCl, 27 mM KCl, 100 mM $Na_2HPO_4$, 18 mM $KH_2PO_4$, pH 7.4, 25° C.) was used. As a solid phase, rFeCysC that was adjusted to be 3 μg/mL by PBS was added to a plate in an amount of 50 μL/well, and allowed to react at 4° C. overnight. After end of the solid phase reaction, the antigen liquid on the plate was removed, and PBS supplemented with 0.5% Bovine Serum Albumin (BSA; Wako Pure Chemical Industries, Ltd.) was added as a blocking liquid in an amount of 150 μL/well, and allowed to react at 37° C. for 60 minutes. After end of the blocking reaction, the plate was washed once, and a culture supernatant of each hybridoma culture was added as a primary antigen in an amount of 50 μL/well, and allowed to react at 37° C. for 60 minutes. After end of the primary antigen reaction, the plate was washed once, and as a secondary antibody, a peroxidase-labeled anti-mouse IgG antibody (SIGMA-ALDRICH) diluted 1000 times with PBS supplemented with 0.1% BSA was added in an amount of 50 μL/well, and allowed to react at 37° C. for 60 minutes. After end of the secondary antibody reaction, the plate was washed 3 times, and as a substrate liquid, PBS supplemented with 0.04% o-phenylenediamine and 0.04% $H_2O_2$ was added in an amount of 150 μL/well, and allowed to react at room temperature under light shielding for 30 to 60 minutes. After end of the substrate reaction, 3 M $H_2SO_4$ was added as a reaction stopper in an amount of 50 μL/well, and the mixture was shaken for 1 minute, and then absorbance at a wavelength of 490 nm was measured by Microplate Reader (Model 550, BIO-RAD). A cell in a positive well showing high absorbance was transferred to a 24-well plate (24 Well Cell Culture Plate; Greiner bio-one) and cultured.
(2-2) Secondary Screening
Secondary screening of an antibody-producing hybridoma was conducted by confirmation by the Western blotting method using rFeCysC as an antigen. According to the method of Lowry, and using DC Protein Assay Kit (BIO-RAD), absorbance at a wavelength of 655 nm was measured by a Microplate Reader, and protein was quantified. A calibration curve was prepared using BSA. The Western blotting method was conducted in the following manner according to a method of Towbin et al. As a transfer membrane, a polyvinylidene difluoride (PVDF) membrane (BIO-RAD) was used. The PVDF membrane was infiltrated with 100% methanol for 10 seconds, followed by a transferring electrode buffer (25 mM Tris-HCl (pH 8.3, 20° C.), 192 mM glycine, 5% methanol) for 30 minutes, and then subjected to electrophoresis. A transfer device was assembled by laminating on a positive electrode plate, filter paper (BIO-RAD), a PVDF membrane, gel after end of SDS-PAGE, and filter paper in this order from bottom, and fixing a negative electrode plate thereon. Filter paper was dipped in advance in an electrode buffer for 2 to 3 minutes. The transfer condition was 60 minutes at a constant current of 1.9 mA/cm². The PVDF membrane after end of the transfer was added with 10 mM Tris-HCl (pH 7.5, 20° C.), 140 mM NaCl, 0.01% Tween 20 (TBST) and 0.5% BSA, and shaken at room temperature for 60 minutes, to effect a blocking operation. After end of the blocking, the membrane was washed with TBST for 5 minutes twice under shaking, and a culture supernatant of cell was used as a primary antibody, and allowed to react at room temperature for 90 minutes under shaking. After end of the primary antibody reaction, the membrane was washed with TBST for 5 minutes twice under shaking, and a peroxidase-labeled anti-mouse IgG antibody diluted 1000 times with TBST was reacted at room temperature for 60 minutes under shaking. After end of the secondary antibody reaction, the membrane was washed with TBST for 5 minutes twice under shaking, and allowed to react for 1 to 5 minutes using 0.06% 3,3-diaminobenzidine tetra-hydrochloride, 0.03% $H_2O_2$, and 50 mM Tris-HCl (pH 7.6, 20° C.) as a substrate reaction liquid. After end of the substrate reaction, the reaction was stopped by washing with water, and then the resultant was dried and stored. For a hybridoma showing reaction positively, cloning was conducted by a limiting dilution method as will be described later.

(3) Cloning

For cloning of hybridoma, a limiting dilution method was used. Concretely, a hybridoma after screening was diluted in a HAT medium so that 2 cells/100 μL was achieved, and seeded in a 96-well plate so that 100 μL/well was achieved. The hybridoma was expansion-cultured on a 24-well plate when semi-confluence was achieved, and again cultured until semi-confluence was achieved, and then confirmed by the Western blotting method using rFeCysC as an antigen similarly to the secondary screening. This cloning operation was conducted twice. Also, for preventing the antibody producibility from decreasing due to subculture of the hybridoma for a long period of time, the hybridoma was stored for every cloning using a cell cryopreservation liquid (Cell Banker (BLC-1), JUJI FIELD INC.).

(4) Large Scale Culture of Antibody-Producing Hybridoma and Collection and Purification of Anti-rFeCysC•mAb A hybridoma having completed cloning was large-scale cultured using a floating cell culture flask (Filter Top SC flask 250 mL 75 cm²; Greiner bio-one). Culture was conducted at 37° C., 5% $CO_2$, for 5 days in a $CO_2$ incubator (JUJI FIELD INC.), and as a medium, a HAT medium was used. The large-scale cultured hybridoma was suspended in serum-free RPMI, and intraperitoneally administered to a nude mouse (Balb/c-nu) in an amount of $2\times10^7$ cells/head. After 10 to 20 days from the administration, a peritoneal fluid was collected. The peritoneal fluid collected from the nude mouse was left still at room temperature for 1 hour or at 4° C. overnight, and then centrifuged at 3000 rpm and 4° C. for 5 minutes, to remove fibrin, hybridoma, erythrocytes and the like in the peritoneal fluid. The separated supernatant was salted out with 50% ammonium sulfate. Concretely, a saturated ammonium sulfate solution in an equivalent amount as the supernatant was gradually dropped under stirring on ice, and stirred for another 1 hour after the dropping. The resultant solution was centrifuged at 10000 rpm and 4° C. for 10 minutes, and the precipitate was dissolved in 20 mM sodium phosphate buffer (pH 7.0). The globulin solution after the salting-out was demineralized using a Sephadex G-25 Fine (GE Healthcare Bio Science) column (inner diameter 1.5 cm, length 30 cm) equilibrated with 20 mM sodium phosphate buffer (pH 7.0). Flow rate of the chromatography was adjusted to 0.5 mL/min by a peristaltic pump (SJ-1211L, ATTO). The globulin solution after demineralization was purified by an affinity chromatography method using Protein G Sepharose 4 Fast Flow (GE Healthcare Bio Science) charged in Eco column (inner diameter 2.5 cm, length 10.0 cm: BIO-RAD). Concretely, the globulin solution after demineralization was added to a column equilibrated with 20 mM sodium phosphate buffer (pH 7.0) at a flow rate of 0.5 mL/min, and then the column was eluted with 100 mM glycine (pH 3.0). The eluate was immediately neutralized with one-tenth amount of 1 M Tris-HCl (pH 9.0). The eluate after purification was demineralized by a Sephadex G-25 Fine column (inner diameter 2 cm, length 30 cm) equilibrated with 50 mM ammonium acetate (pH 7.0), and then lyophilized by using Freeze Dryer (FDU540, EYELA TOKYO RIKAKIKAI CO., LTD.), and stored at −20° C.

(5) Determination of Isotype

Using a Mouse Monoclonal Isotyping Kit (COSMO BIO co., ltd.), isotype of the obtained anti-rFeCysC•mAb was determined according to an attached protocol. Concretely, 150 μL an anti-rFeCysC•mAb sample was added to a development tube, and incubated at room temperature for 30 seconds, and then stirred. To this, an isotyping strip was introduced, and the sample was further incubated at room temperature for 10 to 15 minutes, and then a class and a subclass were read out. As the anti-rFeCysC•mAb sample, the one prepared by diluting a culture supernatant of hybridoma having completed the second cloning 10 times with PBS supplemented with 1% BSA was used. Two kinds of monoclonal antibodies were obtained, and isotype of one antibody C was κ chain of IgG1, and isotype of the other antibody D was κ chain of IgG2a.

(6) Specificity to Feline Native CysC

For antibodies C and D, specificity to feline native CysC was confirmed by using a Western blotting method using urinary protein of cat suffering from chronic kidney disease (CKD) as an antigen. The Western blotting method was executed in a similar manner as described above. As a urinary protein sample for loading in SDS-PAGE, the one prepared by cutting SS bonds in feline urinary protein with 2-Mercaptoethanol was used. FIG. 3 is a photograph showing an experimental result of specificity of antibodies C and D to feline native CysC, and lane 1 represents rFeCysC, and lane 2 represents urinary protein of CKD cat. As shown in FIG. 3, both antibodies C and D were confirmed to specifically react with native CysC.

Experimental Example 4

Identification of $\beta_2$-m Gene (1) Subject Animal

In the present experimental example, one 10-year-old male Japanese cat showing no abnormality in a blood biochemical test and a urine biochemical test, kept in an experimental animal facility was used. This cat was bred in a condition of 12 hours of day and 12 hours of night in a cage for cat, and allowed for free eating and free drinking by feeding once a day.

(2) Extraction of Total RNA from Feline Leukocytes

First, feline blood was collected from the external jugular vein of the subject animal using an EDTA blood collection tube. The collected 5 mL of blood was transferred to a conical tube, centrifuged at 3000× rpm for 5 minutes, and then a buffy coat (leukocyte layer) was separated. Then, total RNA was extracted using QIAamp RNA Blood Kit (QIAGEN) according to an attached protocol. The obtained total RNA was stored at 4° C. until use.

Then, mRNA was separated and purified from total RNA using Oligotex™-dT30 Super mRNA Purification Kit (TAKARA BIO INC.) according to an attached protocol. Concretely, first, 60 μL of total RNA was mingled with 70 μL of 2× Binding Buffer and 14 μL of Oligotex™-dT30, and then warmed at 70° C. for 3 minutes by a thermal cycler (PC801, ASTEC). After warming, hybridization between mRNA and Oligotex™-dT30 Super was allowed by leaving still at room temperature for 10 minutes. A column containing the reaction solution was centrifuged at 15700×g for 5 minutes, suspended in 350 μL of Wash Buffer, and then transferred to a cup of an attached spin column set, centrifuged at 15700×g for 30 seconds, again suspended in 350 μL of Wash Buffer, and then centrifuged at 15700×g for 30 seconds. Oligotex™-dT30 in the column was suspended in 30 μL of RNase free $H_2O$ warmed in advance to 70° C., and mRNA was eluted by using an attached new centrifugal tube for spin column. This operation was repeated twice, and the obtained solution was regarded as a mRNA solution.

Next, from the obtained mRNA solution, first-strand cDNA was prepared by using SMART™ RACE cDNA Amplification Kit (Clontech) for sequencing an intermediate region and 3' end, and using CapFishing™ Full-length cDNA Premix Kit (Seegene) for sequencing 5' end according to an attached protocol.

(3) Determination of Nucleotide Sequence of Intermediate Region of Feline-Derived $β_2$-m Gene In a region where homology is high among revealed nucleotide sequences of animal species, specific primers to feline-derived $β_2$-m gene having the following nucleotide sequences were designed using Genetyx-Win version 7.1 (Software Development Co., Ltd.).

```
Upstream primer 1:
                              (SEQ ID NO: 19)
5'-GGAAAGTCAAATAACCTGAA-3'

Downstream primer 1:
                              (SEQ ID NO: 20)
5'-TCTCGATCCCACTTAACTATC-3'
```

Using Upstream primer 1 and Downstream primer 1 designed in this manner, first-strand cDNA was amplified by PCR using TaKaRa PCR Kit (TAKARA BIO INC.) according to an attached protocol. Concretely, a 0.2 mL PCR tube was charged with 1 μL of prepared First-strand cDNA, 2 μL of 10×PCR Buffer, 2 μL of 25 mM $MgCl_2$, 2 μL of 8 mM dNTP, 0.1 μL of 5 units/mL AmpliTaq Gold (EC2.7.7.7, Applied Biosystems), and each 1 mL of 10 pmol/μL of gene specific primers, a sense primer and an antisense primer and adjusted to 20 μL with distilled water ($dH_2O$), and target cDNA was amplified using Mastercycler Gradient (Eppendorf). Amplification was conducted by 1 cycle of 10 minutes at 95° C., 35 cycles of 1 minute at 95° C., 1 minute at 65° C., and 3 minutes at 72° C., and 1 cycle of 30 seconds at 72° C.

Figure 15:
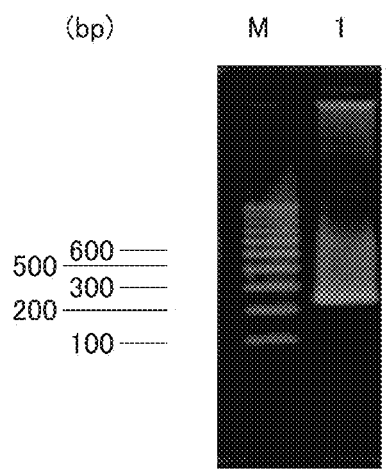
FIG. 15 is an electrophoretic photograph showing a result of PCR of first-strand cDNA in Experimental Example 4.

For confirmation of the amplified cDNA fragment, agarose (SIGMA) was dissolved at a rate of 1% or 2% in 1×TAE (40 mM Tris-HCl, 40 mM acetic acid, 1 mM EDTA, pH 8.0). 18 μL of a PCR product and 2 μL of a loading buffer were mixed, to prepare a loading sample. As the loading buffer, 1×TAE was used, and electrophoresis was conducted by electrification at a constant voltage of 100 V for 30 minutes using an electrophoretic device (Mupid-3, COSMO BIO co., ltd.). Agarose gel after end of the electrophoresis was stained with a 100 ng/mL ethidium bromide (BIO-RAD) solution for 15 minutes, and imaged using Epi-Light (FA500, AISIN COSMOS R&D Co., LTD.). FIG. 15 is a photograph showing a result of agarose gel electrophoresis analysis of cDNA amplified by the PCR method using Upstream primer 1 and Downstream primer 1. Although a band was observed near 240 bp, a smeared migration image was observed. For this reason, a nucleotide sequence was analyzed after cloning this PCR product.

Ligation was conducted using TOPO™ TA Cloning Kit (Invitrogen), according to an attached protocol. Concretely, first, a 0.5 mL PCR tube was added with 2 μL of a PCR solution (Salt Solution 2 M NaCl, 60 mM $MgCl_2$) adjusted to 15 ng/μL, 1 μL of vector plasmid (pCR2.1-TOPO) and 1 μL of $dH_2O$, and the contents were allowed to react at 22.5° C. for 30 minutes.

Next, transformation was conducted using One Shot Chemical Transformation Kit (Invitrogen), according to an attached protocol. Concretely, first, 2 μL of a ligation reaction liquid was added to a tube containing TOP 10 *E. Coli* and left still on ice for 30 minutes, then warmed at 42° C. for 30 seconds, and immediately cooled on ice. Further, 250 μL of a SOC medium was added, and cultured at 37° C. for 60 minutes, and then 50 μL was inoculated on a LB agar plate medium applied with 20 μL of 100 mg/mL X-Gal (TAKARA BIO INC.) per 1 plate, and uniformly spread by a bacteria spreader, and cultured at 37° C. for 18 hours. The LB agar plate medium was prepared by adding 100 mL of ultrapure water to 3.2 mg of LB AGAR (GIBCO BRL™), sterilizing the resultant in an autoclave of 121° C. for 15 minutes, and adding ampicillin in a rate of 0.05 mg/mL, and solidifying the resultant in a petri dish of 9 cm in diameter.

Next, plasmid extraction was conducted using QIAprep™ Spin Miniprep Kit (QIAGEN), according to an attached protocol. Colonies of TOP 10 *E. Coli* for which insertion of the target DNA fragment was confirmed were picked up as many as possible with toothpicks, and inoculated in 10 mM LB liquid medium, and cultured at 37° C. for 18 hours under shaking. Then the culture was centrifuged at 15000×g for 10 minutes, and then the supernatant was removed, to obtain a pellet of TOP 10 *E. Coli*. This TOP 10 *E. Coli* was floated again in 250 μL of TOP 10 *E. Coli* floating buffer (P1 Buffer), and transferred into a 1.5 μL tube. 250 μL of β2 Buffer (alkaline lysis buffer) was added, and slowly inversion-mixed to lyse the bacteria, and then added in 5 minutes with a neutralizing buffer (N3 Buffer) to stop the lysis of bacteria. After centrifugation at 10000×g for 10 minutes, the supernatant was transferred to a spin column set in a 2 mL tube, and centrifuged at 10000×g for 1 minute. After removing the centrifugal supernatant, the spin column was added with 500 μL of propanol-containing guanidine hydrochloride buffer (PB Buffer) and washed by centrifugation at 10000×g for 1 minute, and further centrifugally washed similarly with 750 μL of ethanol-containing demineralized buffer (PE Buffer). After replacing the tube with a new tube, 50 μL of $dH_2O$ was dropped in the center of the spin column, and centrifuged at 10000×g for 1 minute to obtain a plasmid solution. The LB liquid medium used for culture of TOP 10 *E. Coli* was prepared by adding 100 mL of ultrapure water to 2 mg of LB (GIBCO BRL™), sterilizing the resultant at 121° C. for 15 minutes in an autoclave, and adding ampicillin in a rate of 0.05 mg/mL.

(4) Analysis of Nucleotide Sequence in Entire cDNA

A sample for determination of nucleotide sequence was prepared using ABI PRISM® BigDye™ Terminator Cycle Sequencing Ready Reaction Kit (Applied Biosystems), according to an attached protocol. A 0.2 mL PCR tube was added with 1 µL of extracted plasmid adjusted into a concentration of 300 ng/µL, 8 µL of Terminator Ready Reaction Mix (fluorescein donor dye, 6-carboxy fluorescein), 10.68 µL of dH$_2$O, and 0.32 µL of 10 pmol/µL of M13F and M13R primers and PCR reaction was conducted by using a thermal cycler. The PCR reaction was conducted by 25 cycles of 10 seconds at 96° C., 5 seconds at 50° C., and 4 minutes at 60° C.

After end of the reaction, the reaction liquid was transferred to a 1.5 mL tube, added with 60 µL of 75% isopropyl alcohol, lightly mingled and left still for 20 minutes, and then centrifuged at 20000×g for 20 minutes. The supernatant was entirely removed, added again with 250 µL of 75% isopropyl alcohol, centrifuged at 20000×g for 10 minutes, and then moisture of the sediment was evaporated. The obtained PCR product was completely dissolved in 20 µL of Template Suspension Reagent (TSR, Applied Biosystems), and then denatured at 95° C. for 2 minutes. As for analysis of nucleotide sequence, the sequence was analyzed using ABIPrism 310 genetic Analyzer (Applied Biosystems). From the obtained nucleotide sequence data, a nucleotide sequence of cDNA was determined using GENETYX-MAC ver. 8.0 (Software Development) which is analysis software.

After cloning the PCR product, the nucleotide sequence was analyzed, and as a result, the nucleotide sequence as represented by SEQ ID NO: 21 was obtained. This sequence was compared with nucleotide sequences of $β_2$-m cDNA of human, horse, cow, pig and mouse, and homology with each animal of this sequence was analyzed, and respective homologies were 75.3%, 80.0%, 77.1%, 79.6%, and 69.1%. Therefore, it was determined as an intermediate sequence of $β_2$-m cDNA.

(5) 3'-Rapid Amplification of cDNA Ends (RACE)-Neasted PCR Method

Figure 16:
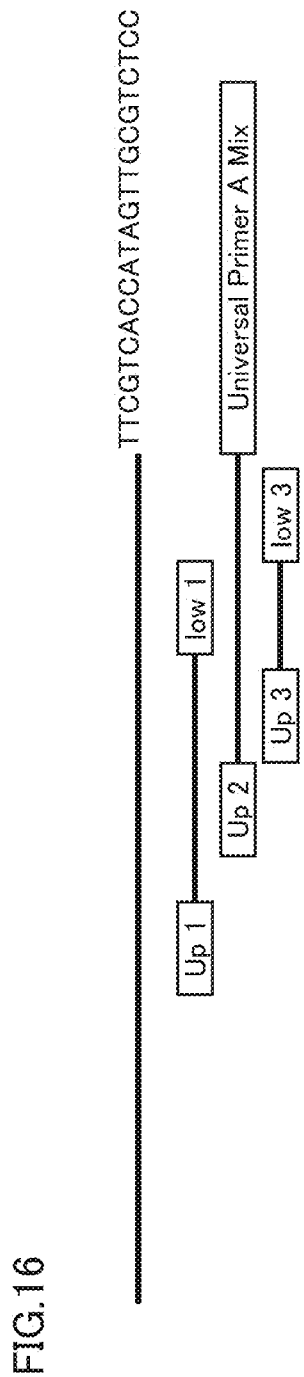
FIG. 16 is an illustration schematically showing a positional relationship between cDNA synthesizable by a kit used in Experimental Example 4 and primers.

Using First-strand cDNA prepared from SMART™ RACE cDNA Amplification Kit, 3'-RACE-Neasted PCR method was conducted. For designing the primers, from the obtained intermediate sequence, specific Upstream primer 2 and Upstream primer 3 respectively having the following nucleotide sequences were prepared. Further, Downstream primer 3 for Nested-PCR was prepared in the region where homology is high from nucleotide sequences of human, mouse, cow, pig, monkey, and rat (FIG. 16).

```
Upstream primer 2:
                                  (SEQ ID NO: 22)
5'-GGGTTCCACCCACCAACAATTCAAAT-3'

Upstream primer 3:
                                  (SEQ ID NO: 23)
5'-TGGTCCACACCGAA-3'

Downstream primer 3:
                                  (SEQ ID NO: 24)
5'-GAAAATATGAAATACGTGTATT-3'
```

First PCR was conducted by using Upstream primer 2 and Universal Primer A Mix (UPM: Clontech) (5'-AAGCAGTG-GTATCAACGCAGAGG-3' (SEQ ID NO: 25)), and then Second Nested-PCR was conducted by using a combination of Upstream primer 3 and Downstream primer 3. PCR was conducted in the condition of 1 cycle of 10 minutes at 95° C., 35 cycles of 1 minute at 95° C., 1 minute at 65° C., and 3 minutes at 72° C. and 1 cycle of 30 seconds at 72° C.

(6) Analysis of cDNA Obtained by 3'RACE Method and Nested-PCR

Figure 17:
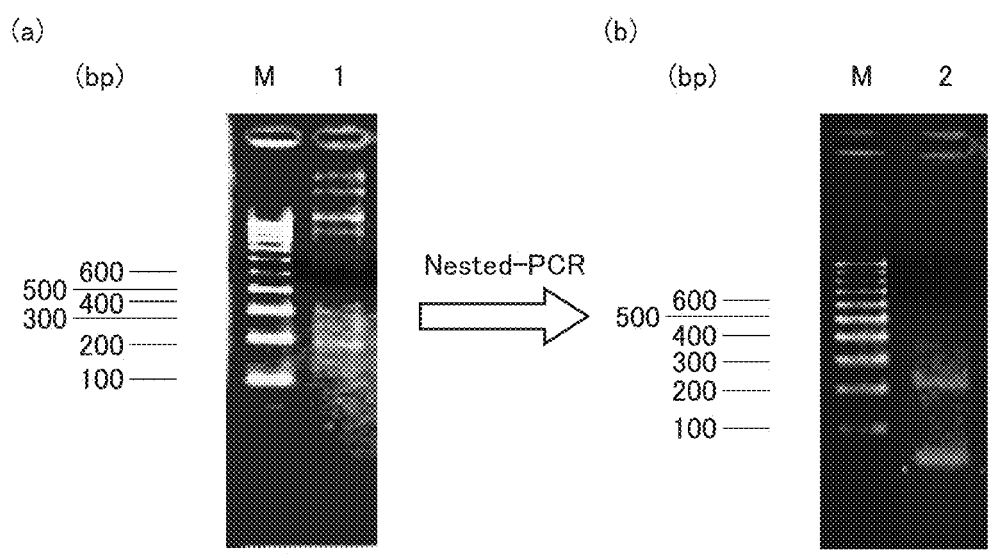
FIG. 17(a) is a photograph of an analysis result by agarose gel electrophoresis of cDNA amplified by Upstream primer 2 and Universal Primer A Mix.
FIG. 17(b) is a photograph showing an analysis result by electrophoresis after nested-PCR.

FIG. 17(a) is a photograph showing a result of analysis by agarose gel electrophoresis of cDNA amplified by Upstream primer 2 and Universal Primer A Mix. As shown in FIG. 17(a), since a plurality of bands were confirmed in the electrophoresis image, nested-PCR was conducted using the cDNA as a template and Upstream primer 3 and Downstream primer 3. FIG. 17(b) is a photograph showing a result of electrophoresis analysis after nested-PCR. As a result, as shown in FIG. 17(b), a band was not observed by Upstream primer 2 and Universal Primer A Mix, but in an electrophoretic image of cDNA amplified by using Upstream primer 3 and Downstream primer 3, bands were observed near about 220 bp and the position of 100 bp or less. For this reason, nucleotide sequence analysis was conducted after cloning the PCR product confirmed near about 220 bp, and a nucleotide sequence represented by SEQ ID NO: 26 was determined. Homologies among the obtained nucleotide sequence of cDNA and $β_2$-m cDNA sequences of human, horse, cow, pig and mouse were analyzed, and the respective homologies were 75.3%, 80.0%, 77.1%, 79.6% and 69.1%, and 3' end nucleotide sequence of feline-derived $β_2$-m gene was revealed.

(7) 5'-Rapid Amplification of cDNA Ends (RACE) PCR Method

Figure 18:
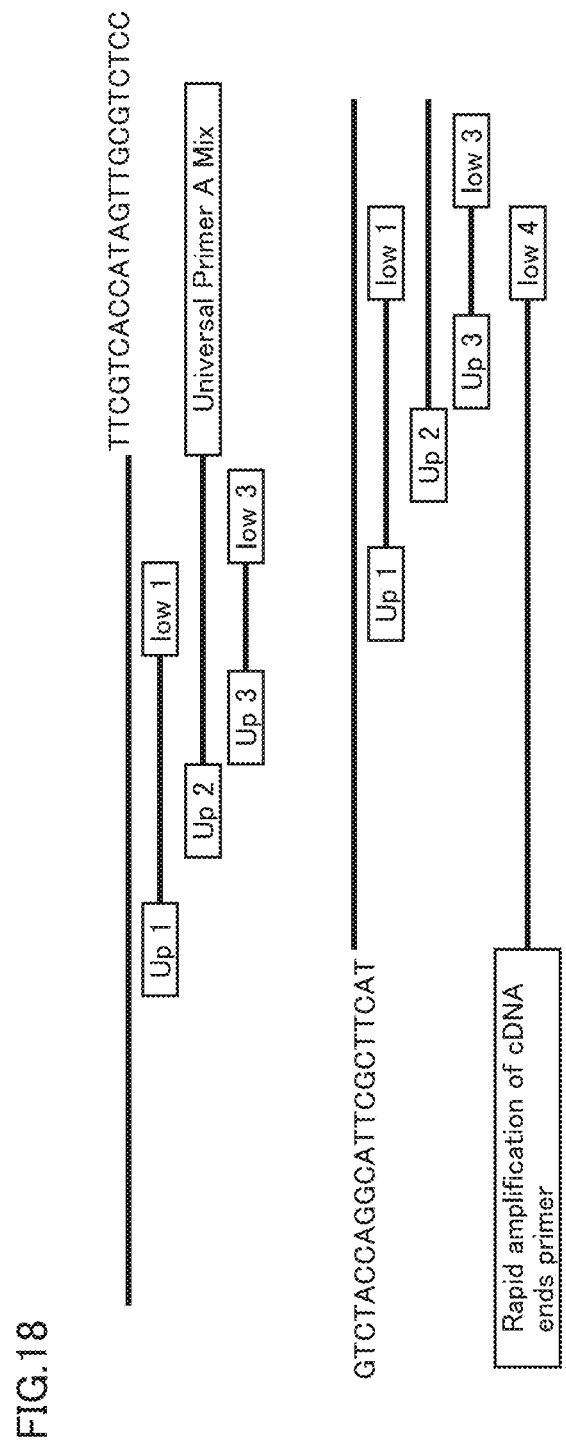
FIG. 18 is an illustration schematically showing a positional relationship between cDNA synthesizable by a kit used in Experimental Example 4 and primers.

5'-RACE PCR method was conducted using CapFishing™ Full-length cDNA Premix Kit (Seegene). mRNA concentrated and dried in the manner as described above was dissolved and mingled in 4 µL of 5 mM dNTP, 2 µL of 10 mM dT-adaptor and 4.5 µL of DEPC-treated water, and warmed in a thermostat of 75° C. for 3 minutes followed by rapid cooling on ice for 2 minutes, and added with 4 µL of RT Buffer of 5-fold concentration, 1 µL of 0.1 M DTT, 1 µL of CapFishing™ Solution, 2 µL of BSA (1 mg/mL), 0.5 µL of RNase inhibitor (40 IU/µL) and 1 µL of Reverse transcriptase (200 IU/µL), and incubated at 42° C. for 1 hour using a thermal cycler (ASTEC PC801). Sequentially, the reaction liquid was added with 3 mL of CapFishing™ adaptor that was warmed in advance in a thermostat of 75° C. for 3 minutes and then rapidly cooled on ice for 2 minutes and 0.3 mL of Reverse transcriptase (200 IU/µL), and warmed again for 30 minutes at 42° C., 15 minutes at 70° C., and 5 minutes at 94° C. by a thermal cycler. After warming at 94° C. for 5 minutes, the reaction liquid was rapidly cooled on ice for 2 minutes, and then added with 180 µL of DEPC-treated water, to prepare First-strand cDNA. Stored First-strand cDNA was subjected to PCR at an annealing temperature of 70° C. Downstream primer 4 used herein was designed to have the following nucleotide sequence based on the nucleotide sequence determined by the analysis of intermediate sequence. As an upstream primer, 10 mM 5'RACE (Rapid amplification of cDNA ends) primer of CapFishing™ Full-length cDNA Premix Kit (Seegene) was used (FIG. 18).

```
Downstream primer 4:
                                  (SEQ ID NO: 27)
5'-GTGTGGACCAGAAGATAGAAAGTCC-3'

5'RACE primer:
                                  (SEQ ID NO: 28)
5'-GTCTACCAGGCATTCGCTTCAT-3'
```

After confirming the band appeared near the theoretical length of the PCR product by agarose electrophoresis, the annealing temperature was adjusted to an ideal condition according to the appearing condition of the band. Cloning was conducted using the one confirmed as a single band in the agarose electrophoresis as a DNA sample, and plasmid extraction DNA was extracted, and then a nucleotide sequence of inserted DNA was determined. For determination of a nucleotide sequence, ABI PRISM BigDye™ Terminator Cycle Sequencing Ready Reaction Kit (Applied Biosystems) was used according to an attached protocol.

(8) Analysis of Agarose Gel Electrophoresis Image of 5'RACE Method

Figure 19:
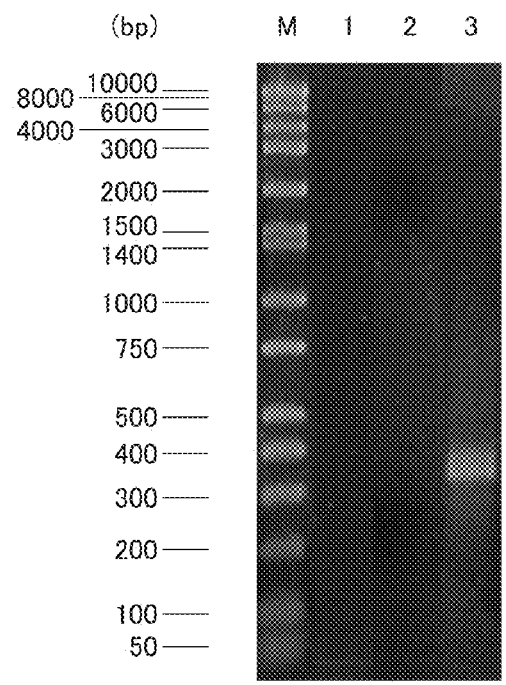
FIG. 19 is an electrophoretic photograph showing a result of 5'RACE-PCR in Experimental Example 4.

An annealing temperature in PCR was set at 75° C., and the 5'RACE method was conducted. Since no band appeared as a result of agarose gel electrophoresis of the PCR product, the annealing temperature was decreased to 70° C., and the 5'RACE method was conducted again. Here, FIG. 19 is a photograph showing a result of agarose gel electrophoresis of the 5'RACE method, and lanes 1 to 3 show the results with the annealing temperatures of 75° C., 71° C. and 70° C., respectively. As shown in FIG. 19, since a band appeared near the intended about 350 bp was smeared, the annealing temperature was increased to 71° C., however, no band appeared again. Therefore, an appropriate annealing temperature of 5'RACE-PCR condition prepared by using 5'RACE primer and Downstream primer 3 was determined to be 70° C., and after cloning, a nucleotide sequence was determined. As a result of analysis of the nucleotide sequence, the nucleotide sequence represented by SEQ ID NO: 29 was revealed. Homologies among the obtained nucleotide sequence and nucleotide sequences of cDNA of $\beta_2$-m of human, horse, cow, pig, mouse, monkey and rat were analyzed, and respective homologies were 74.4%, 78.3%, 78.3%, 78.3%, 69.3%, 72.7% and 69.3%. So, this sequence was determined as 5' end sequence.

(9) Analysis of Nucleotide Sequence in Entire Obtained cDNA

Based on the nucleotide sequences obtained in the above, an entire sequence (SEQ ID NO: 18) was constructed. FIG. 12 is a chart showing the obtained nucleotide sequence of cDNA of feline $\beta_2$-m gene, in comparison with known nucleotide sequences of $\beta_2$-m genes of human, horse, cow, pig, mouse, monkey and rat. In the chart, the part of the nucleotide sequence that is common is indicated by a surrounding square. cDNA length was 360 bases in human, monkey, mouse, and rat, 357 bases in horse, cow, and pig, and 357 bases in the feline cDNA represented by SEQ ID NO: 18 obtained herein. While homology of $\beta_2$-m cDNA nucleotide sequences among other animal species (human, horse, cow, pig, mouse, monkey and rat) was 72.9% on average (Table 3), homologies among the nucleotide sequence obtained herein and other animal species were 73.4%, 76.7%, 74.5%, 76.5%, 67.3%, 71.2% and 68.1%, and average homology was 72.5% (Table 4). This reveals that the obtained nucleotide sequence is feline $\beta_2$-m gene.

TABLE 4

| Species | Nucleotide homology | Reference (EMBL/DDBJ/Gen Bank) |
|---|---|---|
| Horse | 76.73% | AY124653 |
| Cow | 74.52% | X69084 |
| Pig | 76.45% | L13854 |
| Human | 73.41% | NM004048 |
| Mouse | 67.32% | X01838 |
| Monkey | 71.19% | AY349163 |
| Rat | 68.14% | NM012775 |
| Average | 72.54% | |

Experimental Example 5

Synthesis of Feline-Derived $\beta_2$-m (1) Analysis of Amino Acid Sequence of Feline-Derived $\beta_2$-m The nucleotide sequence (SEQ ID NO: 18) of feline-derived $\beta_2$-m gene obtained in Experimental Example 4 was translated into an amino acid sequence, and the amino acid sequence (SEQ ID NO: 17) of feline-derived $\beta_2$-m was analyzed. FIG. 11 is a chart showing the obtained amino acid sequence of feline $\beta_2$-m, in comparison with the known amino acid sequences of $\beta_2$-m of human, horse, cow, pig, mouse, monkey and rat. The number of amino acids in the protein of the present invention represented by SEQ ID NO: 17 was 118 in the entire length, and was extremely approximate to 119 in human, monkey, mouse and rat and 118 in horse, cow and pig. Average homology of amino acid sequence of $\beta_2$-m among other animal species (human, horse, cow, pig, mouse, monkey, and rat) was 72.8% (Table 5). The sequence of the amino acid translated from the nucleotide sequence obtained herein was compared with amino acid sequences of $\beta_2$-m of other animal species, and respective homologies were 65.3%, 72.6%, 68.4%, 74.4%, 60.8%, 63.6% and 62.7%, and average homology was 66.8% (Table 6). Therefore, it was revealed that the obtained amino acid sequence was feline-derived $\beta_2$-m.

TABLE 3

|  | Human | Horse | Cow | Pig | Mouse | Monkey | Average |
|---|---|---|---|---|---|---|---|
| Rat | 64.12% | 60.20% | 66.86% | 65.24% | 81.89% | 71.35% | 72.88% |
| Monkey | 94.23% | 77.47% | 78.30% | 75.55% | 70.80% | | |
| Mouse | 63.01% | 63.14% | 64.37% | 66.17% | | | |
| Pig | 76.82% | 81.19% | 82.10% | | | | |
| Cow | 76.89% | 76.95% | | | | | |
| Horse | 73.87% | | | | | | |

TABLE 5

|  | Human | Horse | Cow | Pig | Mouse | Monkey | Average |
|---|---|---|---|---|---|---|---|
| Rat | 69.75% | 63.87% | 68.01% | 67.80% | 83.19% | 68.07% | 72.78% |
| Monkey | 90.76% | 73.11% | 74.79% | 73.68% | 66.39% | | |
| Mouse | 68.07% | 63.87% | 67.23% | 64.41% | | | |
| Pig | 72.88% | 82.91% | 84.62% | | | | |
| Cow | 74.79% | 77.12% | | | | | |
| Horse | 73.11% | | | | | | |

TABLE 6

| Species | Amino acid homology |
|---|---|
| Horse | 72.55% |
| Cow | 68.38% |
| Pig | 74.36% |
| Human | 65.25% |
| Mouse | 60.78% |
| Monkey | 63.56% |
| Rat | 62.71% |
| Average | 66.80% |

(2) Design of Primer

From the obtained nucleotide sequence of mRNA of feline $\beta_2$-m, a primer was designed using Genetyx-Win version 5.1 (Software Development Co., Ltd.). For using pGEX-6P-1 (GE Healthcare Bio Science) as a vector, primers were prepared to have the following nucleotide sequences by adding a restriction enzyme recognition sequence of BamHI to 5' end of the upstream primer, and a restriction enzyme recognition sequence of SalI to 5' end of the downstream primer. N represents T, A, C or G.

```
Upstream primer:
                              (SEQ ID NO: 30)
5'-NNNGGATCCGTCCAGCATTCCAAAGGTTCAGGT-3'

Upstream primer:
                              (SEQ ID NO: 31)
5'-NNNGTCGACTTACATGTCTCGATCCCACTTAACGACCTT-3'
```

(3) PCR Method

Figure 20:
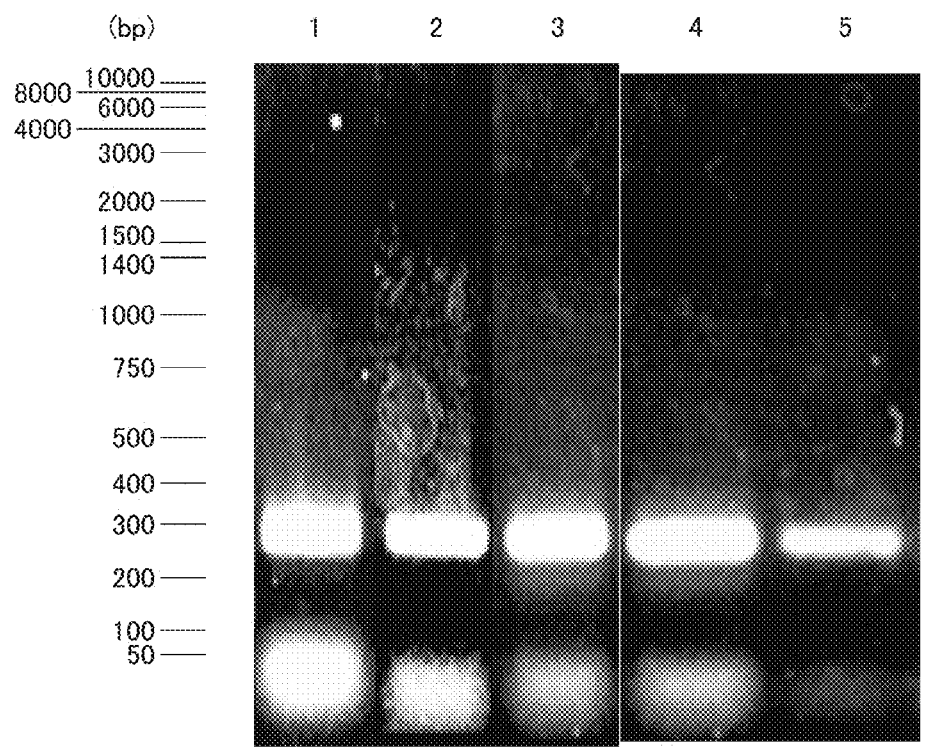
FIG. 20 is a photograph showing a result of electrophoresis for the cases where PCR was conducted at different annealing temperatures in Experimental Example 5.

4 µL of the aforementioned first strand cDNA, 12.5 µL of Go TaqR Green Master Mix (Promega), 1 µL of the upstream primer, 1 µL of the downstream primer and 6.5 µL of RNase free H$_2$O were mingled in a PCR tube, and subjected to PCR by using a thermal cycler. The PCR condition was programmed to include warming at 95° C. for 2 minutes, and 35 cycles of 45 seconds at 95° C., 45 seconds at an annealing temperature of primer pair, and 1 minute at 72° C., and 7 minutes at 72° C. For finding an optimum condition of PCR, the annealing temperature was examined. In RT-PCR conducted with an annealing temperature of 77.5° C., a band of about 50 bp appeared besides a band of about 300 bp estimated as target $\beta_2$-m cDNA. Here, FIG. 20 is a photograph showing a result of electrophoresis by 2% agarose gel for samples subjected to PCR at different annealing temperatures, and lanes 1 to 3 are the cases with different annealing temperatures of 77.5° C., 80° C. and 85° C. respectively, and lanes 4 and 5 are the cases with different addition amounts of primers. The band of about 50 bp reduced as the annealing temperature increased to 77.5° C., 80° C. and 85° C., but not disappeared. Therefore, when the annealing temperature was set at 85° C., the addition amount of primer was varied, and in lane 5, the addition amount of primer was decreased to half, the band of about 50 bp was reduced, and a PCR product of a substantially single band of about 300 bp estimated as a band of $\beta_2$-m cDNA was obtained, which was regarded as insertion cDNA into a vector plasmid.

(4) DNA Extraction from Gel

DNA extraction from gel was conducted using QIAquick Gel Extraction Kit (QIAGEN), according to an attached protocol. A target DNA band in the agarose gel was cut out, and weight of the gel was weighed. The cutout gel was added with 3-times amount of QG buffer, and warmed in a thermostat (TR-2A, ASONE) of 50° C. for 10 minutes, to completely dissolve the gel, and then isopropanol of an equivalent amount to the gel was added and mingled well. The DNA solution was added to a 2 mL collection tube equipped with a column attached to the kit, and centrifuged at room temperature at 13400×g for 1 minute. Then, after removing the filtrate in the collection tube, the column was again added with 0.75 mL of PE buffer, and washed at room temperature by centrifugation at 15700×g for 1 minute, and then the filtrate was removed, and further centrifuged for 1 minute. Then, the column was set in a new 1.5 mL microtube, added with 50 µL of EB buffer, left still at room temperature for 1 minute, and an extraction liquid was collected by centrifugation at 15700×g for 1 minute, and the resultant solution was regarded as a DNA extraction solution.

(5) Concentration of PCR Product

After mixing equivalent amounts of the DNA extraction solution and phenol, the mixture was centrifuged at 15700×g for 5 minutes, and an aqueous layer containing nucleic acid was separated. The aqueous layer was added with the equivalent amount of chloroform and centrifuged at 15700×g for 5 minutes, and then the supernatant was separated. Then the solution after separation was added with 2.5-times amount of 100% ethanol, left still at −80° C. for 30 minutes, and then centrifuged at 15700×g for 5 minutes, and the supernatant was removed to obtain a sediment. The sediment was added with 70% ethanol, and centrifuged at 15700×g for 5 minutes, and then the supernatant was removed, to give a concentrated sample of PCR product.

(6) Preparation of $\beta_2$-m cDNA Incorporated Vector and Transformation Method of E. coli The concentrated sample of PCR product was mingled with 5 µL of BamHI (TAKARA BIO INC.), 5 µL of SalI (TAKARA BIO INC.), 5 µL of H. Buffer (500 mM Tris-HCl, pH 7.5, 100 mM MgCl$_2$, 10 mM Dithiothreitol, 1000 mM NaCl) and 35 µL of RNase free H$_2$O. Also, 5 µL (2.5 µg) of pGEX6P-1 was mingled with 5 µL of BamHI, 5 µL of SalI, 5 µL of H. Buffer and 30 µL of RNase free H$_2$O. Each solution was subjected to a restriction enzyme treatment by overnight incubation at 37° C. and then agarose gel electrophoresis was conducted, and each DNA band was extracted by using QIAquick Gel Extraction Kit. Ligation was conducted by using DNA Ligation Kit (TAKARA BIO INC.). Specifically, 5 µL of Ligation Mix, 1 µL of the $\beta_2$-m cDNA solution having been subjected to a restriction enzyme treatment and 4 µL of pGEX6P-1 were mingled, and left still at 16° C. overnight. Then, by using the reaction solution, transfection of $\beta_2$-m cDNA was conducted. 2.5 µL of the reaction solution was added to 25 µL of E. coli JM109 Competent Cells (TAKARA BIO INC.), and left still on ice for 30 minutes, and heat shock was given in a thermostat of 42° C. for 45 seconds, and the mixture was immediately cooled on ice for 2 minutes, and then gently added with 250 µL of a SOC medium (2% tryptone, 0.5% Yeast extract, 10 mM NaCl, 2.5 mM KCl, 10 mM MgSO$_4$, 10 mM MgCl$_2$, 20 mM glucose) and warmed at 37° C. for 1 hour. Each 100 µL of the $\beta_2$-m cDNA transfected solution was applied on a LB medium supplemented with ampicillin, left still at 37° C. overnight, and then a colony was picked up, and mingled in 1.2 mL of a LB liquid medium supplemented with ampicillin, and cultured at 37° C. overnight. The liquid medium after culture was centrifuged at 13400×g for 1 minute, and then the supernatant was completely removed, and from the obtained sediment, plasmid extraction was conducted.

(7) Plasmid Extraction

Figure 21:
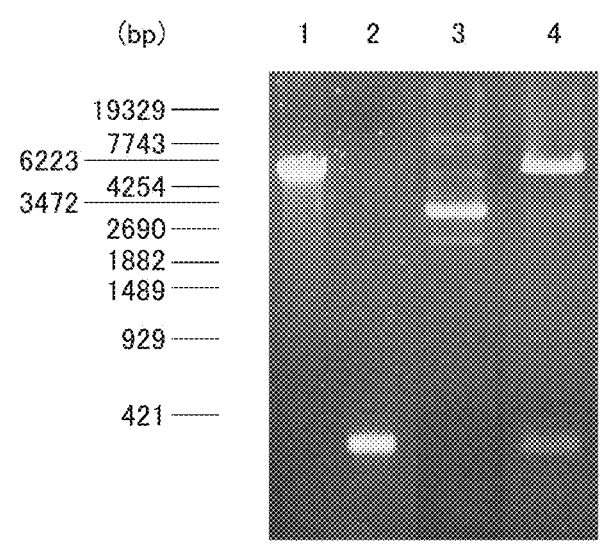
FIG. 21 is a photograph showing a result of agarose gel electrophoresis of pcDNA-F $\beta_2$-m extracted from transformed E. coli in Experimental Example 5.

Plasmid extraction was conducted using QIAPrep Spin Mini Kit 50 (QIAGEN), according to an attached protocol. Concretely, first, the sediment obtained as described above was dissolved in 250 µL of buffer P1, and added with 250 µL of buffer P2, and then gently inversion-mingled to lyse the bacteria. After stopping the lysis reaction by addition of 350 µL of neutralizing N3 buffer, centrifugation at 15700×g was conducted for 10 minutes, and the supernatant was added to an attached collection tube equipped with a column. The column was centrifuged at 5900×g for 1 minute, and then the filtrate was removed, and 500 µL of Binding Buffer was added. Sequentially, after washing by centrifugation at 9300×g for 1 minute, the filtrate was removed, and 750 µL of ethanol-containing demineralized buffer was added, and the mixture was centrifugally washed at 9300×g for 1 minute, and then transferred to a new tube. The membrane of the column was added with 50 µL of Elution Buffer, and centrifuged at 9300×g for 1 minute, to obtain a plasmid extraction solution, and this plasmid was regarded as pcDNA-F $\beta_2$-m, and confirmed by an agarose gel electrophoresis method. FIG. 21 is a photograph showing a result of agarose gel electrophoresis of pcDNA-F $\beta_2$-m extracted from transformed E. coli. In FIG. 21, lanes 1 and 2 respectively show results for plasmid (pGEX6p-1) and $\beta_2$-m cDNA treated with restriction enzymes (BamHI and SalI), lane 3 shows a result for pcDNA-F $\beta_2$-m, and lane 4 shows a result for the sample obtained by treating pcDNA-F $\beta_2$-m with restriction enzymes (BamHI and SalI). As shown in FIG. 21, a thick band was observed at about 3000 bp, and thin bands were observed at about 8000 bp, about 5000 bp and about 2000 bp. Also, in lane 4 for the sample obtained by treating the extracted pcDNA-F $\beta_2$-m with restriction enzymes of BamHI and SalI, bands were observed at about 5000 bp and about 300 bp. These two bands at about 5000 bp and about 300 bp were bands of substantially the same molecular weight in comparison with the migration results of $\beta_2$-m cDNA and pGEX6P-1 before transduction. Whether subcloning of pcDNA-F $\beta_2$-m was succeeded or not was determined by a sequence analysis by Dye Deoxy Terminator Cycle Sequencing Kit (Applied Biosystems) using T7 primer and Applied Biosystems 3130xl Genetic Analyzer (Applied Biosystems). FIG. 22 is an illustration schematically showing a sequence analysis result of pcDNA-F $\beta_2$-m. From the result shown in FIG. 22, it was confirmed that the nucleotide sequence of incorporated $\beta_2$-m cDNA was correctly incorporated into the vector.

(8) Confirmation of GST Fusion Protein Expression

Figure 23:
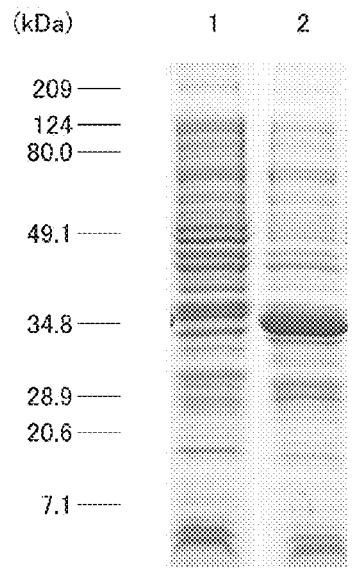
FIG. 23 is a photograph showing a result of SDS-PAGE in Experimental Example 5.

Transfected E. coli was cultured at 37° C. overnight in a LB medium, and then 100 µL of the culture was mingled with 20 µL of Isopropyl-$\beta$-D-thiogalactopyranoside (IPTG: 0.1 mM), and shake-cultured (BR40-LF, TAITEC) at 37° C. for about 2 hours. The E. coli solution after the shake culture was centrifuged at 15700×g for 1 minute, and then the supernatant was removed, and the sediment was added with 30 µL of a solubilizing agent (50 µL of 50 mM Tris-HCl, 100 µL of 1×RIPA Lysis Buffer (Up State), 140 µL of Protease Inhibitor, 710 µL of H$_2$O) to be solubilized, and then centrifugation at 15700×g for 5 minutes was conducted to separate the mixture into a supernatant and a sediment. 30 µl of the supernatant was added with 30 µL of 2×SB solution (2% SDS, 40% Glycerol, 0.6% BPB, 25 mM Tris-HCl Buffer (pH 6.8, 20° C.)) and 1 µL of 2ME, and the mixture was warmed at 95° C. for 3 minutes. The sediment was added with 20λ of SB solution, and crushed for 5 seconds by an ultrasonic crusher (UR-20P, TOMY SEIKO CO, LTD), and then warmed at 95° C. for 3 minutes. Then, for the supernatant and the sediment, GST fusion protein expression and solubility of GST fusion protein in E. coli were confirmed by SDS-PAGE. E. coli obtained after induction expression of GST fusion protein was sonicated and centrifuged, and the obtained supernatant and sediment were migrated in SDS-PAGE. FIG. 23 is a photograph showing a result of SDS-PAGE, and lane 1 shows a result of the supernatant, and lane 2 shows a result of the sediment. Molecular weight of the GST fusion protein was about 37 kDa, and no significant band was observed in the supernatant, however, a clear thick band was observed in the sediment. Therefore, it was confirmed that the GST fusion protein expressed in an insoluble fraction.

(9) SDS-PAGE Method

SDS-PAGE was conducted using a compact PAGE (AE-7300, ATTO) according to the method of Laemmli with modification as shown below. To be more specific, a separation gel was composed of 15% acrylamide, 0.2% N,N-methylene-bis-acrylamide, 0.1% SDS, and 375 mM Tris-HCl buffer (pH 8.8, 20° C.). Gel was prepared by using a 2/4 gel cast (AE-7344, ATTO). An electrode buffer was composed of 0.1% SDS, 129 mM Glycine, and 25 mM Tris (pH 8.3, 20° C.). A sample for loading (SB) was composed of 1% SDS, 20% Glycerol, 0.3% BPB, and 12.5 mM Tris-HCl Buffer (pH 6.8, 20° C.). As a marker, pre-stained SDS-PAGE standard (Broad) marker (BIO-RAD) or SDS-PAGE standard (Broad) marker (BIO-RAD) was used. Electrophoresis was conducted for 30 minutes in a Tris-Gly/PAGE High mode, and then changed into a Tris-Gly/PAGE Low mode, and stopped when the lower ion interface migrates to the position of 1 to 2 mm above the lower end of the gel. For the gel after end of SDS-PAGE, a silver staining method according to an Oakley method was conducted. Concretely, the gel was immobilized in a solution of 30% ethanol and 10% acetic acid, and then washed, and dipped twice in 20% ethanol for 5 minutes. After removal of 20% ethanol, the gel was reacted with a 5% glutaraldehyde solution for 4 minutes, washed with pure water, and then dipped twice in 20% ethanol for 4 minutes. Thereafter, the gel was washed with pure water, reacted with an ammonical silver nitrate solution for 5 minutes, washed with pure water, and then caused to color by a solution of 0.005% citric acid and 0.019% formaldehyde. The gel for which coloring was confirmed was immobilized in a solution of 20% ethanol and 10% acetic acid for 5 minutes, and dipped twice in 20% ethanol for 5 minutes, and then photographed. The silver staining method was conducted entirely in a light-shielded condition.

(10) Expression Induction and Isolation of GST Fusion Protein

E. coli in which expression of GST fusion protein was confirmed was applied on a LB agar medium supplemented with ampicillin, and a colony was picked up and added into 3 mL of a LB liquid medium supplemented with ampicillin and shake-cultured at 37° C. overnight. Sequentially, 3 mL of the culture liquid was added into 250 mL of a LB liquid medium supplemented with ampicillin, and shake-cultured at 37° C. for about 150 minutes, and then added with 2.5 mL of 0.1 mM IPTG, and shake-cultured at 37° C. for about 2 hours, and protein composition after protein expression of the GST fusion protein was analyzed. A culture liquid after expression induction of GST fusion protein was centrifuged at 6000×g for 15 minutes, and the resultant sediment was suspended in 20 mL of 50 mM Tris-HCl (pH 8.0) supplemented with 0.5 mM EDTA, 0.4 M NaCl, 5 mM $MgCl_2$, 5% glycerol, 0.5 mM phenylmethylsulfonyl fluoride (PMSF), 1 mM dithiothreitol (DTT) and 1 mg/mL lysozyme, and left still at 4° C. for 1 hour, and freeze-thawed twice. Sequentially, 0.5% of Nonidet P-40 was added, and the mixture was crushed for 20 seconds 5 times by an ultrasonic crusher, and then centrifuged at 9300×g for 20 minutes, and the supernatant was removed to obtain a sediment. The obtained sediment was suspended again in 10 mL of Phosphate buffer saline (PBS: 140 mM NaCl, 2.7 mM KCl, 10 mM $Na_2PO_4$, 1.8 mM $KH_2PO_4$, pH 7.3) supplemented with 8 M Urea and 0.5 mM DTT and left still at 4° C. for 1 hour, and centrifuged at 9000×g for 20 minutes, to obtain a supernatant. This supernatant was regarded as a GST fusion protein solution.

Figure 24:
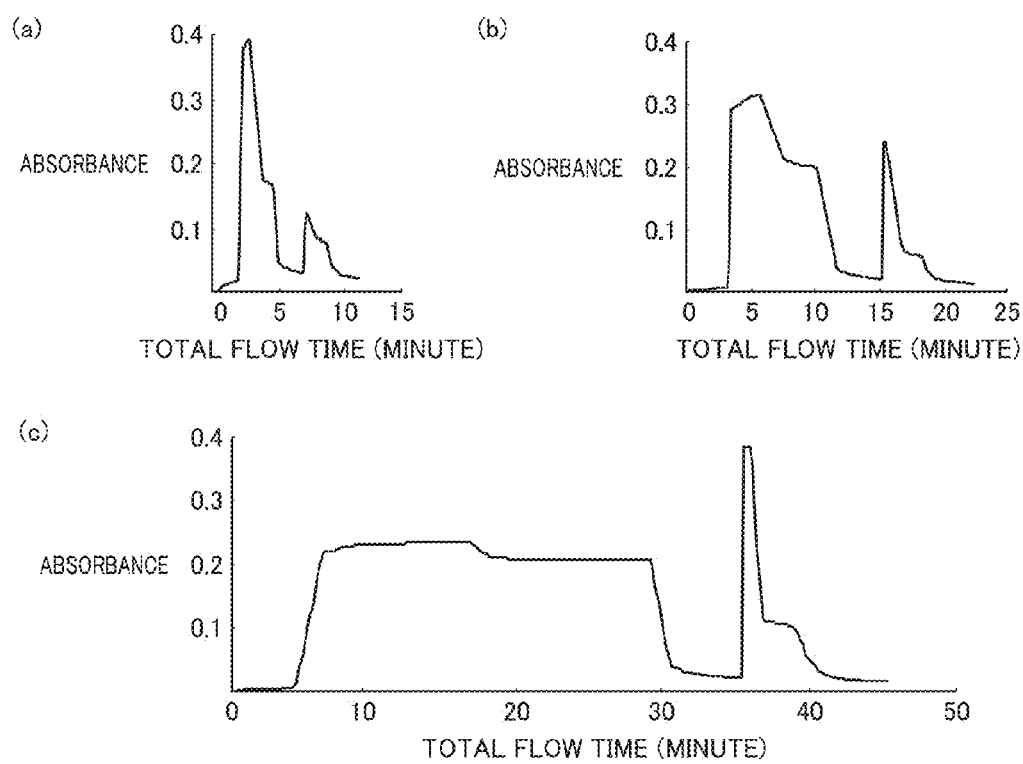
FIG. 24 is an illustration schematically showing a chromatogram for each urea concentration of GST fusion protein solution in Experimental Example 5.
Figure 25:
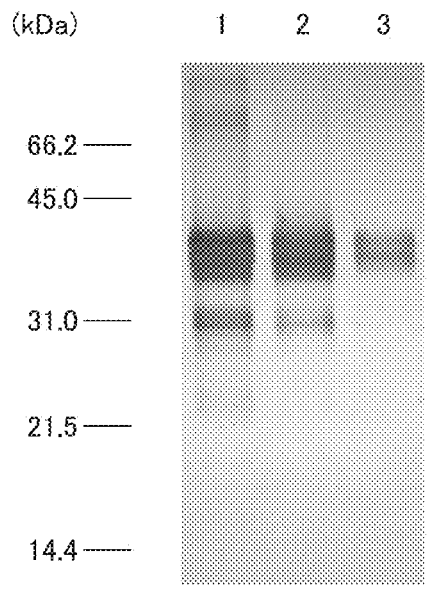
FIG. 25 is a photograph showing a comparative result by SDS-PAGE of ligand binding fractions of respective urea concentrations in Experimental Example 5.

(11) Affinity Chromatography Method 20 mL of the GST fusion protein solution was added to a GSTrap HP column (GE Healthcare Bio Science) equilibrated with a PBS supplemented with 0.5 M Urea by means of a peristaltic pump (SJ-1211L, ATTO) at a flow rate of 0.3 mL/min. For the GST fusion protein solution added to the column, adsorption amounts of GST fusion protein were compared among different urea concentrations. After washing the column with PBS supplemented with 0.5 M Urea, elution was caused with 50 mM Tris-HCl (pH 8.0) supplemented with 10 mM reduced glutathione and 1 M Urea. Absorbance of the GST fusion protein eluate was monitored at an absorption wavelength of 220 nm using a UV region absorbance monitor (AC-5100L, ATTO), and recorded by a recorder (R-01A, RIKADENKI). 2 mL of the obtained GST fusion protein eluate was added with DTT so that the concentration thereof became 1 mM, and mingled, and put into a dialysis membrane for cutting at a molecular weight of 13 kDa (UC30-32-100, Sanko Junyaku Co., Ltd.) and dialyzed against 2 L of 50 mM Tris-HCl (pH 7.5) supplemented with 150 mM NaCl and 1 mM EDTA for about 6 hours. Binding amount of the GST fusion protein to the HiTrap affinity column was compared among different urea concentrations (2 M, 1 M and 0.5 M). Chromatograms of GST fusion protein solutions having different urea concentrations are shown in FIGS. 24(a), (b) and (c). FIGS. 24(a), (b) and (c) respectively show chromatograms using protein samples having a urea concentration of 2 M, 1 M and 0.5 M. In each chromatogram, absorbance change due to addition of the sample was observed in the former half part, and absorbance decreased due to addition of a washing buffer. Thereafter, a sharp peak was observed by addition of the elution buffer, however, increase in absorbance was observed as the urea concentration decreases, and the sharpest fraction was observed at a urea concentration of 0.5 M. For a ligand binding fraction of each urea concentration, comparison was made by SDS-PAGE and the result is shown in FIG. 25. In FIG. 25, lane 1 shows a result of a ligand binding fraction obtained in FIG. 24(c), lane 2 shows a result of a ligand binding fraction obtained in FIG. 24(b), and lane 3 shows a result of a ligand binding fraction obtained in FIG. 24(a). As shown in FIG. 25, as the urea concentration increases, reduction in binding amount of GST fusion protein was observed, and a ligand binding fraction of affinity chromatography conducted at a urea concentration of 0.5 M (obtained in FIG. 24(c)) (hereinafter, referred to as "C4 fraction") was used in the following experiment.

(12) Protease Treatment

Figure 26:
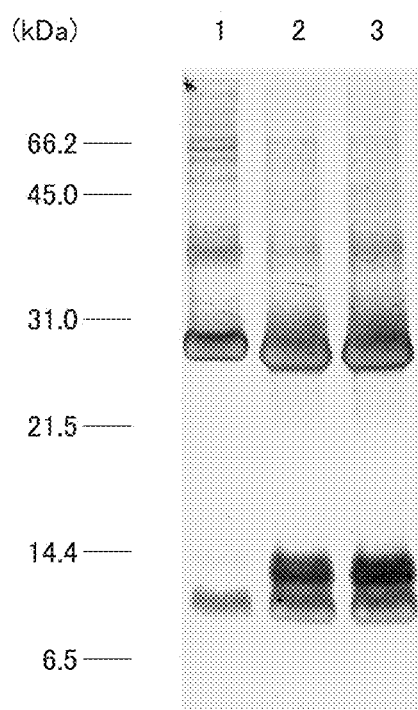
FIG. 26 is a photograph showing a result when various concentrations of DTT was added to a ligand binding fraction and dialysis was performed, and then PreScission Protease was reacted in Experimental Example 5.

For the GST fusion protein eluate after dialysis, protein quantification was conducted using DC Protein Assay (Bio-Rad), and 1 μL of PreScission Protease (GE Healthcare Bio Science) was added per 200 μg of protein and mingled, and then allowed to react at 4° C. for 6 hours or more, to give a sample for high performance liquid chromatography (HPLC). Effects of dialysis and DTT on PreScission Protease reaction were examined. Also using C4 fraction, influence of DTT concentration on PreScission Protease activity was examined. DTT was added to C4 fraction so that the final concentration was 1 mM, 2.5 mM and 5 mM, and following dialysis, PreScission Protease was reacted, and the result is shown in FIG. 26. In FIG. 26, lane 1 shows the case where 1 mM DTT was added, lane 2 shows the case where 2.5 mM DTT was added, and lane 3 shows the case where 5 mM DTT was added. While a band of $β_2$-m of about 11 kDa was observed in every case where DTT was added regardless of the concentration, disappearance of a band of about 15 kDa was observed in the case of addition of 1 mM DTT, and a band of about 13 kDa was observed besides the band of $β_2$-m when DTT was added in concentrations of 2.5 mM and 5 mM. From these results, a sample obtained by treating C4 fraction added with 1 mM DTT with PreScission Protease after dialysis was used in the high performance liquid chromatography method (HPLC) which is the subsequent purification step.

(13) HPLC Method

Figure 27:
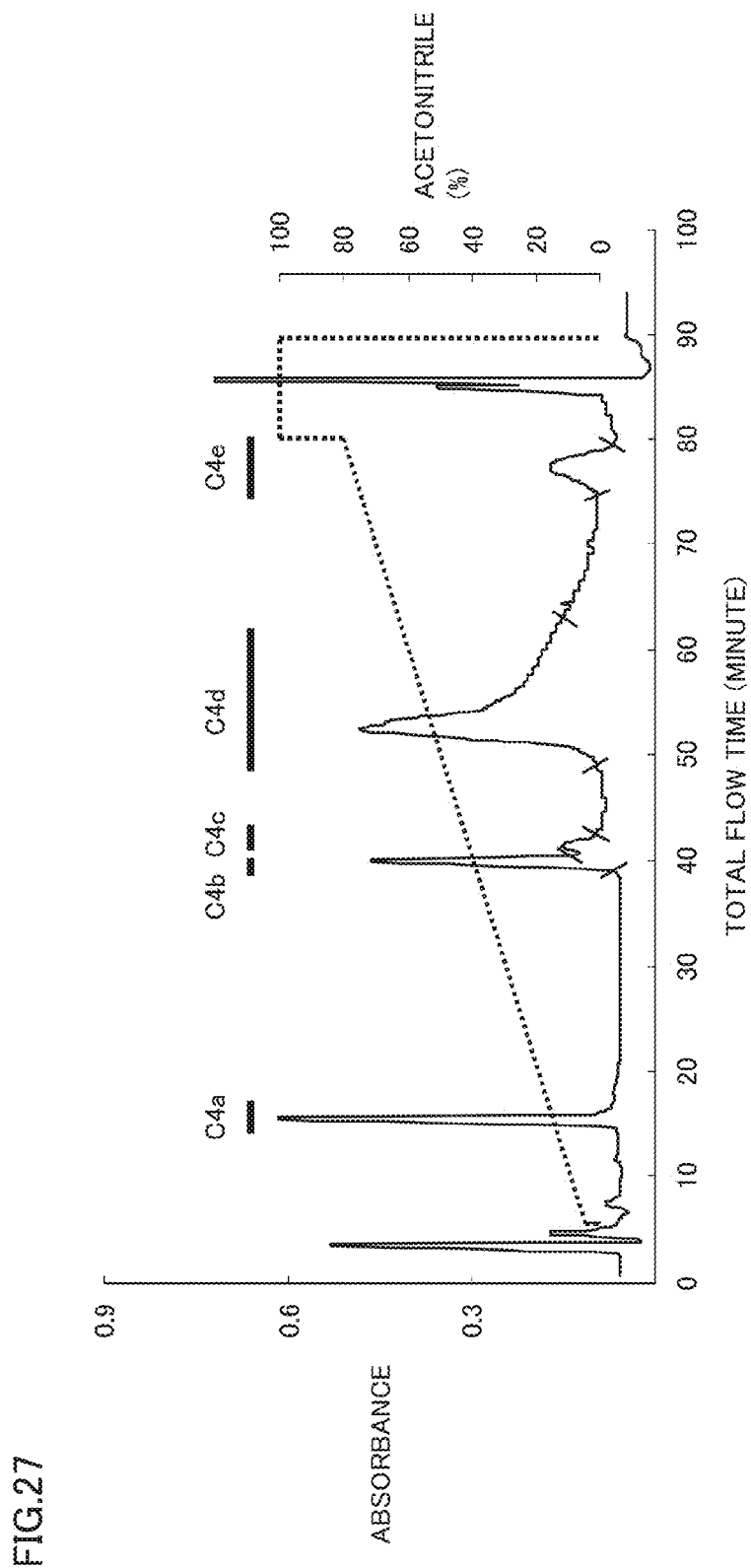
FIG. 27 is an illustration schematically showing a chromatogram of HPLC in Experimental Example 5.
Figure 28:
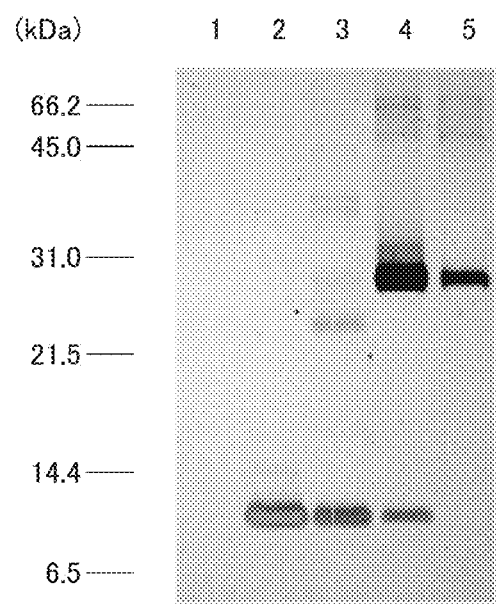
FIG. 28 is a photograph showing a result of SDS-PAGE for each fraction after HPLC.

An HPLC system consists of a system controller (SCL-10A VP, Shimadzu), a liquid sending unit (LC-10AD VP, Shimadzu), a UV region spectrophotometer (SPD-10A VP, Shimadzu), a column oven (CTO-10A VP, Shimadzu) and a deaeration unit (DGU-14A, Shimadzu), and as a column, MightysilRP-18 GP250-4.6 (Cat. No. 25415-96, KANTO CHEMICAL) was used. As a separation condition of HPLC, a flow rate of mobile phase of 1 mL/min, and a sample addition amount of 400 μL were used, and for a column equilibrated with a 0.1% trifluoroacetic acid (TFA) solution, a liner gradient of 0 to 80% of acetonitrile concentration was applied using an acetonitrile solution supplemented with 0.1% TFA. The eluate was monitored by its absorbance at an absorption wavelength of 220 nm, and a detected peak was fractionated and centrifuged by a centrifugal concentrator (CC-181, TOMY) for 1 hour, and then dried in a lyophilizer (FDU-540, EYELA) and then stored at −20° C. Also, protein of each eluted fraction was analyzed by an SDS-PAGE method. FIG. 27 is an illustration schematically showing a chromatogram of HPLC. C4 fraction after a protease treatment was eluted mainly into five fractions. These five fractions were named C4a, C4b, C4c, C4d and C4e in the order of being eluted, and analyzed by SDS-PAGE. FIG. 28 is a photograph showing a result of SDS-PAGE for each fraction after HPLC. As shown in FIG. 28, no band was observed in C4a fraction, a band of about 11 kDa was observed in C4b fraction, bands of about 11 kDa, about 25 kDa, and about 27 kDa were observed in C4c fraction, and bands of about 11 kDa and about 27 kDa were observed in C4d, and a band of about 27 kDa was observed in C4e fraction. A protein estimated as target $β_2$-m was detected as a single band in C4b fraction. Acetonitrile concentration at the time of elution of C4b fraction was 39.5%. This eluate was regarded as recombinant feline $β_2$-m and concentrated by centrifugation, and lyophilized, and then stored at −80° C.

Experimental Example 6

Preparation of Antibody-Producing Hybridoma, and Anti-rFeβ$_2$-m Antibody

For preparing a monoclonal antibody against the protein synthesized in Experimental Example 5 as an antigen of recombinant feline β$_2$-m (rFeβ$_2$-m), first, an antibody-producing hybridoma was prepared.

(1) Preparation of Antibody-Producing Hybridoma (1-1) Immunological Method

An immunological method was conducted by subcutaneous injection of purified rFeβ$_2$-m as an antigen on a hindlimb footpad of Balb/c mouse. Immunization was conducted 4 times every 5 days, and first to third immunizations were conducted using 200 μL (50 μg/foot) of an antigen liquid that was prepared by mixing equivalent amounts of 100 μL (1 mg/mL) of an antigen solution and an adjuvant, and emulsifying the same, and the last immunization was conducted using only 20 μL (10 μg/foot) of an antigen solution. As the adjuvant, Adjuvant Complete Freund (Wako Pure Chemical Industries, Ltd.) was used in the first immunization, and Adjuvant Incomplete Freund (Wako Pure Chemical Industries, Ltd.) was used in the second to third immunizations.

(1-2) Cell Fusion

After 3 days from the last immunization, a popliteal lymph node was extracted, and after collection of lymphocytes, cell fusion was conducted using GenomONE-CF (ISHIHARA SANGYO KAISHA, LTD.). As a myeloma cell, P3X63-Ag8.653 (Dainippon Sumitomo Pharma Co., Ltd.) was used. A fusion method was conducted according to an attached protocol. Concretely, first, lymphocytes and myeloma cells were mixed at a cell number ratio of 5:1, and centrifuged at 1000 rpm and 4° C. for 5 minutes, and then the supernatant was removed. Then an ice-cooled buffer for fusion was added in an amount of 1 mL per $10^8$ cells of lymphocytes, and suspended uniformly, and then an ice-cooled HVJ-Envelope suspension was added in an amount of 25 μL per 1 mL of the cell mixture. After leaving the cell suspension on ice for 5 minutes, centrifugation at 1000 rpm and 4° C. was conducted for 5 minutes, and the resultant was incubated at 37° C. for 15 minutes in the condition that the supernatant was not removed and the cells were pelletized.

After end of the incubation, a growth medium warmed at 37° C. was added in an amount of 50 mL per $10^8$ cells of lymphocytes, and after suspending, a 96-well plate (96 Well Cell Culture Plate: Greiner bio-one) was seeded with the same in an amount of 100 μL/well. As the growth medium, RPMI1640 (Invitrogen) supplemented with 100,000 IU/mL of penicillin G (PG; Meiji Seika Pharma Co., Ltd.), 100 mg/mL of streptomycin (SM; Meiji Seika Pharma Co., Ltd.), 7.5% Briclone (IL-6, human, BriClone; Cat. No. BR-001, Dainippon Sumitomo Pharma Co., Ltd.), and 10% inactivated fetal bovine serum (FBS; NICHIREI CORPORATION) was used, and operations at the time of addition and suspending were conducted gently. After culturing for 24 hours, the culture medium was replaced with a HAT medium prepared by adding 2% HAT (Invitrogen) to the growth medium as described above.

(2) Screening of Antibody-Producing Hybridoma

For the obtained hybridoma, primary screening using an ELISA method was conducted after 1 week from the cell fusion, and only hybridoma in the well determined as reaction positive as a result of the screening was confirmed by secondary screening using a Western blotting method.

(2-1) Primary Screening

By the ELISA method using rFeβ$_2$-m as an antigen, primary screening of an antibody-producing hybridoma was conducted. As an ELISA plate, a 96 Well ELISA Microplate (Greiner bio-one) was used. For washing of the plate, an automated washing machine (Auto Mini Washer AMW-8, BIOTEC Co., Ltd.) was used, and as a washing liquid, PBS (1.37 M NaCl, 27 mM KCl, 100 mM Na$_2$HPO$_4$, 18 mM KH$_2$PO$_4$, pH 7.4, 25° C.) was used. As a solid phase, rFeβ$_2$-m that was adjusted to be 3 μg/mL by PBS was added to a plate in an amount of 50 μL/well, and allowed to react at 4° C. overnight. After end of the solid phase reaction, the antigen liquid on the plate was removed, and PBS supplemented with 0.5% Bovine Serum Albumin (BSA; Wako Pure Chemical Industries, Ltd.) was added as a blocking liquid in an amount of 150 μL/well, and allowed to react at 37° C. for 60 minutes. After end of the blocking reaction, the plate was washed once, and a culture supernatant of each hybridoma culture was added as a primary antigen in an amount of 50 μL/well, and allowed to react at 37° C. for 60 minutes. After end of the primary antigen reaction, the plate was washed once, and as a secondary antibody, a peroxidase-labeled anti-mouse IgG antibody (SIGMA-ALDRICH) diluted 1000 times with PBS supplemented with 0.1% BSA was added in an amount of 50 μL/well, and allowed to react at 37° C. for 60 minutes. After end of the secondary antibody reaction, the plate was washed 3 times, and as a substrate liquid, PBS supplemented with 0.04% o-phenylenediamine and 0.04% H$_2$O$_2$ was added in an amount of 150 μL/well, and allowed to react at room temperature under light shielding for 30 to 60 minutes. After end of the substrate reaction, 3 M H$_2$SO$_4$ was added as a reaction stopper in an amount of 50 μL/well, and the mixture was shaken for 1 minute, and then absorbance at a wavelength of 490 nm was measured by Microplate Reader (Model 550, BIO-RAD). A cell in a positive well showing high absorbance was transferred to a 24-well plate (24 Well Cell Culture Plate; Greiner bio-one) and cultured.

(2-2) Secondary Screening

Secondary screening of an antibody-producing hybridoma was conducted by confirmation by the Western blotting method using rFeβ$_2$-m as an antigen. According to the method of Lowry, and using DC Protein Assay Kit (BIO-RAD), absorbance at a wavelength of 655 nm was measured by a Microplate Reader, and protein was quantified. A calibration curve was prepared using BSA. The Western blotting method was conducted in the following manner according to a method of Towbin et al. As a transfer membrane, a polyvinylidene difluoride (PVDF) membrane (BIO-RAD) was used. The PVDF membrane was infiltrated with 100% methanol for 10 seconds, followed by an electrode buffer for transferring (25 mM Tris-HCl (pH 8.3, 20° C.), 192 mM glycine, 5% methanol) for 30 minutes, and then subjected to electrophoresis. A transfer device was assembled by laminating on a positive electrode plate, filter paper (BIO-RAD), a PVDF membrane, gel after end of SDS-PAGE, and filter paper in this order from bottom, and fixing a negative electrode plate thereon. Filter paper was dipped in advance in an electrode buffer for 2 to 3 minutes. The transfer condition was 60 minutes at a constant current of 1.9 mA/cm$^2$. The PVDF membrane after end of the transfer was added with 10 mM Tris-HCl (pH 7.5, 20° C.), 140 mM NaCl, 0.01% Tween 20 (TBST) and 0.5% BSA, and shaken at room temperature for 60 minutes, to effect a blocking operation. After end of the blocking, the membrane was washed with TBST for 5 minutes twice under shaking, and a culture supernatant of cell was used as a primary antibody, and allowed to react at room temperature for 90 minutes under shaking. After end of the primary antibody reaction, the membrane was washed with TBST for 5 minutes twice under shaking, and a peroxidase-labeled anti-mouse IgG antibody diluted 1000 times with TBST was reacted at room temperature for 60 minutes under shaking. After end of the secondary antibody reaction, the membrane was washed with TBST for 5 minutes twice under shaking, and allowed to react for 1 to 5 minutes using 0.06% 3,3-diaminobenzidine tetra-hydrochloride, 0.03% $H_2O_2$, and 50 mM Tris-HCl (pH 7.6, 20° C.) as a substrate reaction liquid. After end of the substrate reaction, the reaction was stopped by washing with water, and then the resultant was dried and stored. For a hybridoma showing reaction positivity, cloning was conducted by a limiting dilution method as will be described later.

(3) Cloning

For cloning of hybridoma, a limiting dilution method was used. Concretely, a hybridoma after screening was diluted in a HAT medium so that 2 cells/100 μL was achieved, and seeded in a 96-well plate so that 100 μL/well was achieved. The hybridoma was expansion-cultured on a 24-well plate when semi-confluence was achieved, and again cultured until semi-confluence was achieved, and then confirmed by the Western blotting method using $rFe\beta_2$-m as an antigen similarly to the secondary screening. This cloning operation was conducted twice. Also, for preventing the antibody producibility from decreasing due to subculture of the hybridoma for a long period of time, the hybridoma was stored for every cloning using a cell cryopreservation liquid (Cell Banker (BLC-1), JUJI FIELD INC.).

(4) Large Scale Culture of Antibody-Producing Hybridoma and Collection and Purification of Anti-$rFe\beta_2$-m•mAb A hybridoma having completed cloning was large-scale cultured using a floating cell culture flask (Filter Top SC flask 250 mL 75 $cm^2$; Greiner bio-one). Culture was conducted at 37° C., 5% $CO_2$, for 5 days in a $CO_2$ incubator (JUJI FIELD INC.), and as a medium, a HAT medium was used. The large-scale cultured hybridoma was suspended in serum-free RPMI, and intraperitoneally administered to a nude mouse (Balb/c-nu) in an amount of $2\times10^7$ cells/head. After 10 to 20 days from the administration, a peritoneal fluid was collected. The peritoneal fluid collected from the nude mouse was left still at room temperature for 1 hour or at 4° C. overnight, and then centrifuged at 3000 rpm and 4° C. for 5 minutes, to remove fibrin, hybridoma, erythrocytes and the like in the peritoneal fluid. The separated supernatant was salted out with 50% ammonium sulfate. Concretely, a saturated ammonium sulfate solution in an equivalent amount as the supernatant was gradually dropped under stirring on ice, and stirred for another 1 hour after the dropping. The resultant solution was centrifuged at 10000 rpm and 4° C. for 10 minutes, and the precipitate was dissolved in 20 mM sodium phosphate buffer (pH 7.0). The globulin solution after the salting-out was demineralized using a Sephadex G-25 Fine (GE Healthcare Bio Science) column (inner diameter 1.5 cm, length 30 cm) equilibrated with 20 mM sodium phosphate buffer (pH 7.0). Flow rate of the chromatography was adjusted to 0.5 mL/min by a peristaltic pump (SJ-1211L, ATTO). The globulin solution after demineralization was purified by an affinity chromatography method using Protein G Sepharose 4 Fast Flow (GE Healthcare Bio Science) charged in Eco column (inner diameter 2.5 cm, length 10.0 cm: BIO-RAD). Concretely, the globulin solution after demineralization was added to a column equilibrated with 20 in M sodium phosphate buffer (pH 7.0) at a flow rate of 0.5 mL/min, and then the column was eluted with 100 mM glycine (pH 3.0). The eluate was immediately neutralized with one-tenth amount of 1 M Tris-HCl (pH 9.0). The eluate after purification was demineralized by a Sephadex G-25 Fine column (inner diameter 2 cm, length 30 cm) equilibrated with 50 mM ammonium acetate (pH 7.0), and then lyophilized by using Freeze Dryer (FDU540, EYELA TOKYO RIKAKIKAI CO., LTD.), and stored at –20° C.

(5) Determination of Isotype

Using a Mouse Monoclonal Isotyping Kit (COSMO BIO co., ltd.), isotype of the obtained anti-$rFe\beta_2$-m•mAb was determined according to an attached protocol. Concretely, 150 μL an anti-$rFe\beta_2$-m•mAb sample was added to a development tube, and incubated at room temperature for 30 seconds, and then stirred. To this, an isotyping strip was introduced, and the sample was further incubated at room temperature for 10 to 15 minutes, and then a class and a subclass were read out. As the anti-$rFe\beta_2$-m•mAb sample, the one prepared by diluting a culture supernatant of hybridoma having completed the second cloning 10 times with PBS supplemented with 1% BSA was used. Two kinds of monoclonal antibodies were obtained, and isotype of one antibody E was κ chain of IgG1, and isotype of the other antibody F was κ chain of IgG2b.

(6) Specificity to Feline Native $\beta_2$-m

For antibodies E and F, specificity to feline native $\beta_2$-m was confirmed by using a Western blotting method using urinary protein of cat suffering from chronic kidney disease (CKD) as an antigen. For comparison, a similar experiment was conducted using $rFe\beta_2$-m purified as described above as an antigen. The Western blotting method was executed in a similar manner as described above. As a urinary protein sample for loading in SDS-PAGE, the one prepared by cutting SS bonds in feline urinary protein with 2-Mercaptoethanol was used. FIG. 13 is a photograph showing an experimental result of specificity of antibodies E and F to feline native $\beta_2$-m, and lane 1 represents $rFe\beta_2$-m, and lane 2 represents urinary protein of CKD cat. As shown in FIG. 13, both antibodies E and F were confirmed to specifically react with native $\beta_2$-m. It is conceivable that $\beta_2$-m in urine of CKD cat has a higher molecular weight than the purified $rFe\beta_2$-m because $\beta_2$-m in urine of CKD cat binds to sugar.

(7) Examination of Feline Nephropathy Diagnosis

By a sandwich method using the aforementioned antibodies E and F, $\beta_2$-m in urine was quantified for one healthy cat and three cats suffering from chronic kidney disease. Concretely, antibody E was solid-phased at 0.5 mg/well, and blocked, and then reacted with urine of one healthy cat and three cats suffering from chronic kidney disease respectively for 2 hours. After washing, antibody F labeled with biotin was reacted for 2 hours, and then avidin peroxidase was reacted for 1 hour, and a substrate reaction was conducted using tetramethylbenzidine, and absorbance at 450 nm was measured. FIG. 14 is a graph showing the result, and the vertical axis represents $\beta_2$-m concentration in urine (ng/mL). As is apparent from FIG. 14, antibodies E and F of the present invention little reacted with urine of the healthy cat, but reacted with all of the three cats suffering from chronic kidney disease. This result suggests that urine of a cat suffering from chronic kidney disease contains plenty of $\beta_2$-m, and that the antibody of the present invention can be utilized for diagnosis of feline nephropathy.

Experimental Example 7

Identification of $\alpha_1$-m Gene (1) Subject Animal

In the present experimental example, one 10-year-old male Japanese cat showing no abnormality in a blood biochemical test and a urine biochemical test, kept in an experimental animal facility was used. This cat was bred in a condition of 12 hours of day and 12 hours of night in a cage for cat, and allowed for free eating and free drinking by feeding once a day.

(2) Extraction of Total RNA from Feline Liver

After introduction by intravenous injection of propofol, the animal was anesthetized with isoflurane, and feline liver was collected by biopsy under ultrasonic guidance. Extraction of total RNA was conducted using ISOGEN(NIPPON GENE) and TAKARA FastPure RNA Kit (TAKARA BIO INC.), according to an attached protocol. Liver tissue was homogenized in ISOGEN, added with 200 μL of chloroform, and inversion-mingled for 15 seconds and centrifuged at 12000×g for 15 minutes. After transferring 300 μL of the supernatant to another tube, 3 μL of ethachinmate (NIPPON GENE), and 9.9 μL of 3 M sodium acetate were added, and mingled, and then added with 750 μL of isopropyl alcohol and mingled well, and then centrifuged at 12000×g for 15 minutes. A pellet obtained by removing the supernatant was washed by centrifugation at 12000×g for 10 minutes with 1 mL of 70% ethanol. Then, using the pellet after washing as a material, total RNA was purified using TAKARA FastPure RNA Kit. The obtained pellet was dissolved in 500 μL of Lysis Buffer supplemented with 2-metrcaptoethanol, centrifuged at 16000×g for 7 minutes, and then 350 μL of the supernatant was transferred to a new tube. Then, 175 μL of Solubilization Buffer was added to this and mingled, and then Wash Buffer (WB) of 175 μL of special grade ethanol was added, and centrifuged at 8000×g for 1 minute. This washing process was conducted 3 times, and the column was transferred to a tube for collection, added with 100 μL of Elution Buffer in the center of the column, then incubated at room temperature for 2 minutes, and eluted at 8000×g for 1 minute, and the obtained solution was named total RNA.

mRNA was separated and purified from total RNA using Oligotex™-dT30 Super mRNA Purification Kit (TAKARA BIO INC.) according to an attached protocol. 60 μL of total RNA was mingled with 70 μL of 2× Binding Buffer and 14 μL of Oligotex™-dT30, and then warmed at 70° C. for 3 minutes by a thermal cycler (PC801, ASTEC). After warming, hybridization between mRNA and Oligotex™-dT30 Super was allowed by leaving still at room temperature for 10 minutes. A column containing the reaction solution was centrifuged at 15700×g for 5 minutes, suspended in 350 μL of Wash Buffer, then transferred to a cup of an attached spin column set, centrifuged at 15700×g for 30 seconds, again suspended in 350 μL of Wash Buffer, and then centrifuged at 15700×g for 30 seconds. Oligotex™-dT30 in the column was suspended in 30 μL of RNase free $H_2O$ warmed in advance to 70° C., and mRNA was eluted by using an attached new centrifugal tube for spin column. This operation was repeated twice, and the obtained solution was regarded as a mRNA solution.

Then, using the obtained mRNA solution and first-strand cDNA Synthesis Kit (GE Healthcare Bio Science), first-strand cDNA was prepared according to an attached protocol. 30 μL of mRNA was warmed at 65° C. for 10 minutes by a thermal cycler, subsequently rapidly cooled on ice for 2 minutes, and then 11 μL of a Bulk first-strand reaction-mix, 1 μL of a DTT Solution and 1 μL of random hexamer were added. The resultant solution was warmed at 37° C. for 1 hour by a thermal cycler, and the obtained solution was regarded as first-strand cDNA.

(3) Determination of Nucleotide Sequence of Intermediate Region of Feline-Derived $α_1$-m Gene In a region where homology is high among revealed nucleotide sequences of animal species, specific primers to feline-derived $α_1$-m gene having the following nucleotide sequences were designed using Genetyx-Win version 7.1 (Software Development Co., Ltd.).

```
Upstream primer 1:
                                    (SEQ ID NO: 34)
5'-CCARGTGCAGGARAACT-3'

Downstream primer 1:
                                    (SEQ ID NO: 35)
5'-CTTCTCHGAGTAGAAYTKGTTVCC-3'
```

In the aforementioned nucleotide sequences, R represents A or G, H represents A or T or C, Y represents C or T, K represents G or T, and V represents G or A or C.

Figure 32:
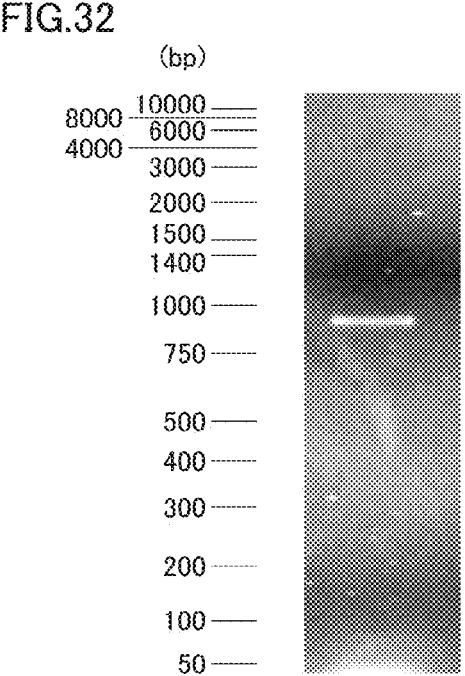
FIG. 32 is an electrophoretic photograph showing a result of PCR of first-strand cDNA in Experimental Example 7.

Using Upstream primer 1 and Downstream primer 1 designed in this manner, the first-strand cDNA was amplified by PCR. Here, FIG. 32 is an electrophoretic photograph of a result of PCR of the first-strand cDNA. After confirming a band appeared near the theoretical length of the PCR product by agarose electrophoresis, the annealing temperature was adjusted to 60° C. which is an ideal condition, and a single band as shown in FIG. 32 was obtained. The single band obtained by electrophoresis was cut out from the agarose gel, and DNA was extracted. DNA extraction was conducted using QIAquick Gel Extraction Kit (QIAGEN) according to an attached protocol. For the cutout DNA band, weight of gel was measured, and 3-times amount of QG buffer was added, and the resultant was warmed in a thermostat (TR-2A, ASONE) of 50° C. for 10 minutes, to completely dissolve the gel, and then isopropanol of an equivalent amount to the gel was added and mingled well. The DNA solution was added to a 2 mL collection tube equipped with a column attached to the kit, and centrifuged at room temperature at 13400×g for 1 minute. Then, after removing the filtrate in the collection tube, the column was again added with 0.75 mL of PE buffer, and washed at room temperature by centrifugation at 15700×g for 1 minute, and then the filtrate was removed, and further centrifuged for 1 minute. Then, the column was set in a new 1.5 mL microtube, added with 50 μL of EB buffer, left still at room temperature for 1 minute, and an extraction liquid was collected by centrifugation at 15700×g for 1 minute.

Then, the obtained DNA was treated using TOPO TA Cloning Kit (Invitrogen) and pGEM-T Easy Vector System (Promega) according to an attached protocol. Concretely, first, 3 μL of the stored PCR product, 1 μL of pGEM-T Easy Vector, 1 μL of T4 DNA Ligase (3 Weiss units/μL), and 2× Rapid Ligation Buffer, 5 μL of T4 DNA Ligase were mingled in a 500 μL Eppendorf tube, and incubated at 4° C. overnight to cause ligation. The obtained reaction liquid was further transformed into E. coli. 2.5 μL of the ligation reaction liquid was added to E. coli JM109 Competent cells (TAKARA BIO INC.), left still on ice, and then subjected to Heat Shock in a thermostat of 42° C. for 45 seconds, and then rapidly cooled for 2 minutes. Further, the reaction liquid was gently added with 450 μL of a SOC medium (2% Tryptone, 0.5% Yeast Extract, 10 mM NaCl, 2.5 mM KCl, 10 mM $MgCl_2$, 10 mM $MgSO_4$, 20 mM glucose), and shake-cultured at 37° C. for 90 minutes at a rate of 150 rpm in a shake incubator (PERSONA-11, TAITEC). Each 100 μL of E. coli suspension after culture was uniformly spread by a bacteria spreader on a LB agar plate medium (TAKARA BIO INC.) applied with 20 μL of 20 mg/mL X-gal (TAKARA BIO INC.) dissolved in DMSO and 100 μL of 100 mM Isopropyl-β-D-thigalactopyranoside (IPTG), and cultured at 37° C. using an incubator (IS62, TAITEC). After 18 hours, only a white colony was picked up with a sterilized toothpick, and inoculated in 3 mL of a LB liquid medium supplemented with 5 mg/mL of ampicillin, and cultured at 37° C. for 24 hours. After culture, plasmid of E. coli was extracted by using QIAPrep Spin Mini Kit 50 (QIAGEN) according to an attached protocol. The obtained plasmid was treated with a restriction enzyme (EcoRI), and then whether ligation occurred was determined by an agarose gel electrophoresis method. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 36) of about 900 bases.

Figure 33:
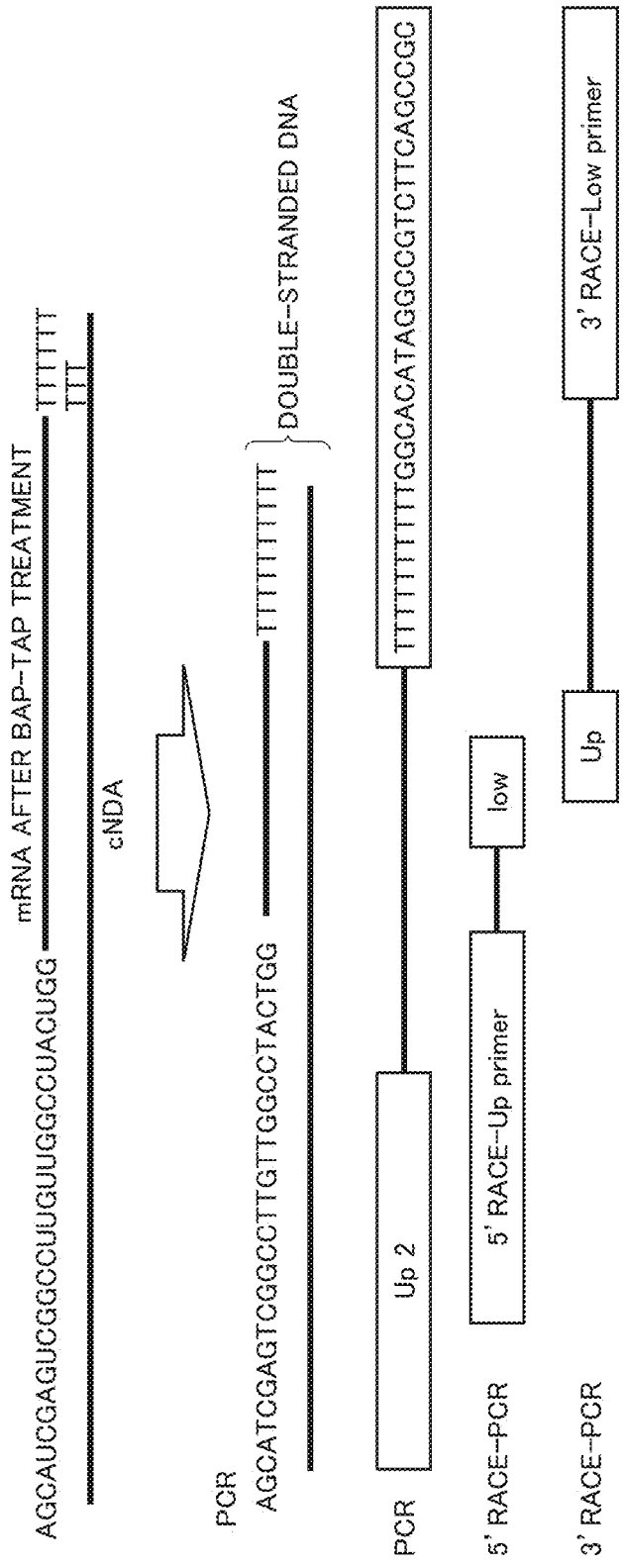
FIG. 33 is an illustration schematically showing a positional relationship between cDNA synthesizable by a kit used in Experimental Example 7 and primers.

(4) Preparation of Full-Length mRNA Using Oligo-Capping Method 1 to 5 µg of mRNA separated from feline liver by the aforementioned method was mingled in BAP buffer containing 40 U of RNasin Ribonuclease Inhibitor (Promega) and 0.5 U of Bacterial Alkarine Phosphatase (BAP: TAKARA BIO INC.), and allowed to react at 37° C. for 60 minutes. After enzyme reaction, the BAP-treated mRNA solution was subjected to phenol/chloroform extraction, and caused to precipitate by using Ethachinmate (WAKO). The BAP-treated mRNA was further mingled with 60 U of RNasin, 8.0 U of Tobacco Acid Pyrophosphatase (TAP: WAKO) and a TAP buffer, and allowed to react at 37° C. for 60 minutes. After end of the enzyme reaction, the BAP-TAP-treated mRNA solution was subjected to phenol/chloroform extraction, and concentrated by using Ethachinmate. The BAP-TAP-treated mRNA was added with 100 ng of synthesized Oligo-RNA (5'-AGCAUCGAGUCGGCCUUGUUGGCCUACUGG-3': SEQ ID NO: 37), allowed to react at 65° C. for 5 minutes, and then mingled with a ligation buffer containing 40 U of RNasin and 50 U of T4 RNA ligase (TAKARA BIO INC.), and allowed to react at 20° C. for 3 hours. After end of the enzyme reaction, the mRNA solution treated with RNA ligation was subjected to phenol/chloroform extraction, and concentrated by using Ethachinmate (WAKO), and then using Universal RiboClone cDNA Synthesis System (Promega, Wis.) and according to an attached protocol, Random Hexameric primer, AMV Reverse transcriptase, and first-strand buffer were added, and first-strand was synthesized at 42° C. for 60 minutes, and then RNaseH, DNA polymerase I, and Second-strand buffer were added and synthesized at 14° C. for 2 hours, and then the reaction liquid was added with T4 DNA Polymerase and dNTP to arrange the terminal (FIG. 33). The obtained double-stranded DNA was added with the sequence of 5'-GCGGCTGAAGACGGCCTATGTGCCT$_{17}$-3' at its 3' end by PCR by using Upstream primer 2 and Downstream primer 2 having the following nucleotide sequences. PCR was conducted in the condition of 1 cycle of 2 minutes at 95° C., 30 cycles of 1 minute at 95° C., 1 minute at 55° C., 1 minute at and 30 seconds at 72° C., and 1 cycle of 10 minutes at 72° C.

```
Upstream primer 2:
                                        (SEQ ID NO: 38)
5'-AGCATCGAGTCGGCCTTGTTG-3'

Downstream primer 2:
                                        (SEQ ID NO: 39)
5'-GCGGCTGAAGACGGCCTATGTGCCT-3'
```

(5) 5'RACE-PCR Method

The dsDNA prepared in the manner as described above was amplified by a 5'RACE-PCR method. The primers used in 5'RACE-PCR method were designed to respectively have the following nucleotide sequences based on the sequence of the added RNA adaptor for the upstream primer, and based on the nucleotide sequence of the intermediate region already determined for the downstream primer.

```
5'RACE-upstream primer:
                                        (SEQ ID NO: 40)
5'-TCGGCCTTGTTGGCCTACTG-3'

5'RACE-downstream primer:
                                        (SEQ ID NO: 41)
5'-TGGTCATGCTGATCTCCTTGTC-3'
```

Figure 34:
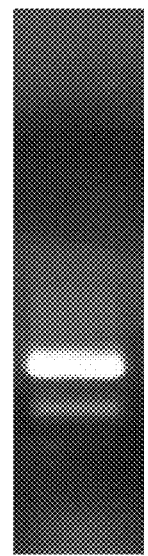
FIG. 34 is an electrophoretic photograph showing a result of 5'RACE-PCR in Experimental Example 7.

Using the primers designed in this manner, PCR was conducted in the condition of 1 cycle of 2 minutes at 95° C., 30 cycles of 1 minute at 95° C., 1 minute at 65° C. and 1 minute at 72° C., and 1 cycle of 10 minutes at 72° C. FIG. 34 is an electrophoretic photograph showing a result of 5'RACE-PCR, and as shown in FIG. 34, the obtained PCR product was confirmed as a substantially single band. Ligation and transformation were conducted using TOPO TA Cloning Kit (Invitrogen), pGEM-T Easy Vector System (Promega) and E. coli JM109 Competent cells (TAKARA BIO INC.). From E. coli JM109 after culture, plasmid was extracted using QIAPrep Spin Mini Kit 50 (QIAGEN), and the obtained plasmid was treated with a restriction enzyme (EcoRI), and then insertion of DNA fragment was confirmed by an agarose gel electrophoresis method. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 42) of about 360 bases.

(6) 3'RACE-PCR Method

The dsDNA prepared in the manner as described above was amplified by a 3'RACE-PCR method. The primers used in the 3'RACE-PCR method were designed to respectively have the following nucleotide sequences based on the nucleotide sequence of the intermediate region already determined for the upstream primer and based on the sequence of the DNA adaptor added to 3' end for the downstream primer.

```
3'RACE-upstream primer:
                                        (SEQ ID NO: 43)
5'-TACAACCAGCTCTGGGCATTC-3'

3'RACE-downstream primer:
                                        (SEQ ID NO: 44)
5'-GCGGCTGAAGACGGCCTATGT-3'
```

Figure 35:
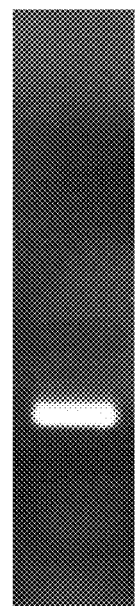
FIG. 35 is an electrophoretic photograph showing a result of 3'RACE-PCR in Experimental Example 7.

Using the primer designed in this manner, PCR was conducted in the condition of 1 cycle of 2 minutes at 95° C., 30 cycles of 1 minute at 95° C., 1 minute at 55° C. and 1 minute at 72° C., and 1 cycle of 10 minutes at 72° C. FIG. 35 is an electrophoretic photograph showing a result of 3'RACE-PCR, and the obtained PCR product was confirmed as a completely single band as shown in FIG. 35. For the obtained PCR product, ligation and transformation were conducted using TOPO TA Cloning Kit (Invitrogen), pGEM-T Easy Vector System (Promega) and E. coli JM109 Competent cells (TAKARA BIO INC.). From E. coli JM109 after culture, plasmid was extracted using QIAPrep Spin Mini Kit 50 (QIAGEN), and the obtained plasmid was treated with a restriction enzyme (EcoRI), and then insertion of DNA fragment was confirmed by agarose gel electrophoresis. Also, using T7 primer, and further using Dye Deoxy Terminator Cycle Sequencing Kit (Applied Biosystems) and Applied Biosystems 3130xl Genetic Analyzer (Applied Biosystems), nucleotide sequence analysis was conducted to reveal a nucleotide sequence (SEQ ID NO: 45) of about 380 bases.

(7) Analysis of Nucleotide Sequence in the Entirety of Obtained cDNA

Based on the nucleotide sequences obtained in the above, an entire sequence (SEQ ID NO: 46) was constructed. The sequence of nucleic acid of the full length represented by SEQ ID NO: 46 had 1284 bases, and encoded $\alpha_1$-m therein. In the nucleotide sequence represented by SEQ ID NO: 46, it was revealed that the 92nd to 694th bases constitute a structural gene encoding $\alpha_1$-m ($\alpha_1$-m gene: SEQ ID NO: 33).

FIG. 30 is a chart showing the obtained nucleotide sequence of cDNA of feline $\alpha_1$-m gene, in comparison with known nucleotide sequences of $\alpha_1$-m genes of human, cow, pig and rat. In the chart, the part of the nucleotide sequence that is common is indicated by a surrounding square. The full-length cDNA was 1284 bp, and encoded $\alpha_1$-m and bikunin therein. Homology of full-length cDNA was compared. While homologies with other animal species distributed from 75.74 to 84.12%, homology between feline full-length cDNA and those of other animal species was 82.20% on average, revealing that this sequence was full-length cDNA encoding $\alpha_1$-m (Table 7). In comparison of cDNA of the part encoding $\alpha_1$-m, length of feline cDNA obtained herein was 603 bases while nucleic acid length was 603 bases in human and cow, and 602 bases in rat. While homologies of nucleotide sequences of $\alpha_1$-m cDNA with those of other animal species (human, cow, pig and rat) distributed in the range of 74.30 to 80.30%, homology of the sequence obtained herein with that of other animal species was 80.48% on average, revealing that the obtained nucleotide sequence was feline $\alpha_1$-m gene (Table 8).

TABLE 7

|  | Rat | Pig | Cow | Human | Average |
|---|---|---|---|---|---|
| Cat | 77.20% | 85.60% | 81.87% | 84.14% | 82.20% |
| Human | 79.29% | 84.12% | 81.21% |  |  |
| Cow | 75.74% | 85.60% |  |  |  |
| Pig | 78.76% |  |  |  |  |

TABLE 8

|  | Rat | Pig | Cow | Human | Average |
|---|---|---|---|---|---|
| Cat | 76.12% | 80.10% | 82.12% | 83.61% | 80.48% |
| Human | 78.44% | 77.45% | 80.30% |  |  |
| Cow | 75.70% | 79.77% |  |  |  |
| Pig | 74.30% |  |  |  |  |

Experimental Example 8

Synthesis of Feline-Derived $\alpha_1$-m (1) Analysis of Amino Acid Sequence of Feline-Derived $\alpha_1$-m The nucleotide sequence (SEQ ID NO: 33) of feline-derived $\alpha_1$-m gene obtained in Experimental Example 7 was translated into an amino acid sequence, and the amino acid sequence (SEQ ID NO: 32) of feline-derived $\alpha_1$-m was analyzed. FIG. 29 is a chart showing the obtained amino acid sequence of feline $\alpha_1$-m, in comparison with the known amino acid sequences of $\alpha_1$-m of human, cow, pig and rat. In the chart, the part of the amino acid sequence that is common is indicated by a surrounding square. As a result, the number of amino acids in feline-derived $\alpha_1$-m was 201 in the entire length, which is completely the same with the number of amino acids of 201 in human and cow, and is approximate to the number of amino acids of 200 in rat. The position and number of structural amino acid cysteine conserved among other animal species were also similar. As shown in Table 9, regarding homology, while homologies of amino acid sequences of $\alpha_1$-m among other animal species (human, cow, pig and rat) distributed in the range of 68.32 to 78.71%, average homology between the amino acid sequence of the feline $\alpha_1$-m obtained herein and those of other animal species was 76.39%. Therefore, it was revealed that the obtained amino acid sequence was feline $\alpha_1$-m.

TABLE 9

|  | Rat | Pig | Cow | Human | Average |
|---|---|---|---|---|---|
| Cat | 71.14% | 75.74% | 76.62% | 82.09% | 76.39% |
| Human | 74.63% | 72.77% | 74.13% |  |  |
| Cow | 71.64% | 78.71% |  |  |  |
| Pig | 68.32% |  |  |  |  |

(2) Expression and Purification of Recombinant Protein Using GST Fusion Protein

In order to amplify nucleic acids for the feline-derived $\alpha_1$-m protein region excluding the part of putative signal peptide region and bikunin which is composite protein, PCR was conducted. Primers were designed to respectively have the following nucleotide sequences by adding a restriction enzyme site of EcoRI to 5' end for an upstream primer and adding a restriction enzyme site of XhoI and His-Tag to 3' end for a downstream primer.

Upstream primer:
(SEQ ID NO: 47)
5'-CACGGATCCAGCCCCGTGCTGACGCCGCCCGATGACATCCAAGTG
CAAGAGAACTT-3'

Downstream primer:
(SEQ ID NO: 48)
5'-CACCTCGAGTTAGTGGTGGTGGTGGTGATGCGTGAGTGGAGAGGG
CTCTGGTTCC-3'

Using the upstream primer and the downstream primer as described above, PCR was conducted in the condition of 1 cycle of 2 minutes at 95° C., 30 cycles of 1 minute at 95° C., 1 minute at 75° C. and 1 minute at 72° C., and 1 cycle of 10 minutes at 72° C. After subjecting the PCR product to agarose gel electrophoresis, DNA was extracted from the agarose gel. After mixing equivalent amounts of the DNA extraction solution and phenol, centrifugation at 15700×g was conducted for 5 minutes, and then an aqueous layer containing nucleic acids was separated. The separated aqueous layer was mixed with the equivalent amount of chloroform, and centrifuged at 15700×g for 5 minutes, and then the supernatant was separated. Then, the solution after separation was added with 2.5-times amount of 100% ethanol, left still at −80° C. for 30 minutes, and then centrifuged at 15700×g for 5 minutes, and then the supernatant was removed, to obtain a sediment. The sediment was added with 70% ethanol, centrifuged at 15700×g for 5 minutes, and then the supernatant was removed, to obtain a concentrated sample of the PCR product. The concentrated sample of the PCR product was mingled with 5 μL of EcoRI (TAKARA BIO INC.), 5 μL of XhoI (TAKARA BIO INC.), 5 μL of H. Buffer (500 mM Tris-HCl, pH 7.5, 100 mM MgCl$_2$, 10 mM Dithiothreitol, 1000 mM NaCl) and 35 μL of RNase free H$_2$O. Also, 5 μL (2.5 μg) of pGEX6P-1 (GE Healthcare Bio Science) was mingled with 5 µL of EcoRI, 5 µL of XhoI, 5 µL of H. Buffer and 30 µL of RNase free H$_2$O. After treating each solution with the restriction enzymes by incubation at 37° C. overnight, agarose gel electrophoresis was conducted, and each DNA band was extracted by using QIAquick Gel Extraction Kit (QIAGEN). Ligation was conducted using DNA Ligation Kit (TAKARA BIO INC.). To be more specific, 5 µL of Ligation Mix, 1 µL of cDNA solution of $\alpha_1$-m treated with restriction enzymes and 4 µL of pGEX6P-1 were mingled, and left still at 16° C. overnight, and thus, a plasmid vector (pGEX-$\alpha_1$-m) ligated with cDNA of $\alpha_1$-m was created. Further, 2.5 µL of this pGEX-$\alpha_1$-m solution was added to 25 µL of E. coli JM109 Competent Cells (TAKARA BIO INC.), left still on ice for 30 minutes, and subjected to Heat shock in a thermostat of 42° C. for 45 seconds, and immediately cooled on ice for 2 minutes, and then gently added with 250 µL of a SOC medium (2% Tryptone, 0.5% Yeast extract, 10 mM NaCl, 2.5 mM KCl, 10 mM MgSO$_4$, 10 mM MgCl$_2$, 20 mM Glucose) and kept at 37° C. for 1 hour. 100 µL of E. coli solution transfected with pGEX-$\alpha_1$-m was applied on a LB medium supplemented with ampicillin, and left still at 37° C. overnight, and then a colony was picked up, and mingled with 1.2 mL of a LB liquid medium supplemented with ampicillin and cultured at 37° C. overnight. The liquid medium after culture was centrifuged at 13400×g for 1 minute, and then the supernatant was completely removed, and from the obtained sediment, pGEX-$\alpha_1$-m was extracted using QIAPrep Spin Mini Kit 50 (QIAGEN). This pGEX-$\alpha_1$-m was confirmed by an agarose gel electrophoresis method. Whether subcloning of the pGEX-$\alpha_1$-m was succeeded or not was determined by using Dye Deoxy Terminator Cycle Sequencing Kit (Applied Biosystems) using T7 primer and nucleotide sequence analysis using Applied Biosystems 3130xl Genetic Analyzer (Applied Biosystems).

(3) Confirmation of Expression of GST Fusion Protein with His-Tag

E. coli transfected with pGEX-$\alpha_1$-m was cultured at 37° C. overnight in a LB medium, and then 100 µL of the culture was mingled with 20 µL of Isopropyl-β-D-thiogalactopyranoside (IPTG: 0.1 mM), and shake-cultured (BR40-LF, TAITEC) at 30° C. for about 2 hours. The E. coli solution after the shake culture was centrifuged at 15700×g for 1 minute, and then the supernatant was removed, and the sediment was added with 30 µL of a solubilizing agent (50 µL of 50 mM Tris-HCl, 100 µL of 1×RIPA Lysis Buffer (Up State), 140 µL of Protease Inhibitor, 710 µL of H$_2$O) to be solubilized, and then centrifugation at 15700×g for 5 minutes was conducted to separate the mixture into a supernatant and a sediment. 30 µL of the supernatant was added with 30 µL of 2×SB solution (2% SDS, 40% Glycerol, 0.6% BPB, 25 mM Tris-HCl Buffer (pH 6.8, 20° C.)) and 1 µL of 2ME, and the mixture was warmed at 95° C. for 3 minutes. The sediment was added with 20 µL of SB solution, and crushed for 5 seconds by an ultrasonic crusher (UR-20P, TOMY SEIKO CO, LTD), and then warmed at 95° C. for 3 minutes. Then, for the supernatant and the sediment, expression of GST fusion protein with His-Tag and solubility of GST fusion protein with His-Tag in E. coli were confirmed by SDS-PAGE.

(4) SDS-PAGE Method

SDS-PAGE was conducted using a compact PAGE (AE-7300, ATTO) according to a method of Laemmli with modification as shown below. To be more specific, a separation gel was composed of 15% Acrylamide, 0.2% N,N-Methylene-bis-Acrylamide, 0.1% SDS, and 375 mM Tris-HCl buffer (pH 8.8, 20° C.). Gel was prepared by using a 2/4 gel cast (AE-7344, ATTO). An electrode buffer was composed of 0.1% SDS, 129 mM Glycine, and 25 mM Tris (pH 8.3, 20° C.). A sample for loading (SB) was composed of 1% SDS, 20% Glycerol, 0.3% BPB, and 12.5 mM Tris-HCl Buffer (pH 6.8, 20° C.). As a marker, pre-stained SDS-PAGE standard (Broad) marker (BIO-RAD) or SDS-PAGE standard (Broad) marker (BIO-RAD) was used. Electrophoresis was conducted for 30 minutes in a Tris-Gly/PAGE High mode, and then changed into a Tris-Gly/PAGE Low mode, and stopped when the lower ion interface migrates to the position of 1 to 2 mm above the lower end of the gel. For the gel after end of SDS-PAGE, a silver staining method according to an Oakley method was conducted. Concretely, the gel was immobilized in a solution of 30% ethanol and 10% acetic acid, and then washed, and dipped twice in 20% ethanol for 5 minutes. After removal of 20% ethanol, the gel was reacted with a 5% glutaraldehyde solution for 4 minutes, washed with pure water, and then dipped twice in 20% ethanol for 4 minutes. Thereafter, the gel was washed with pure water, reacted with an ammonical silver nitrate solution for 5 minutes, washed with pure water, and then caused to color by a solution of 0.005% citric acid and 0.019% formaldehyde. The gel for which coloring was confirmed was immobilized in a solution of 20% ethanol and 10% acetic acid for 5 minutes, and dipped twice in 20% ethanol for 5 minutes, and then photographed. The silver staining method was conducted entirely in a light-shielded condition.

(5) Expression Induction and Isolation of GST Fusion Protein with His-Tag

Figure 36:
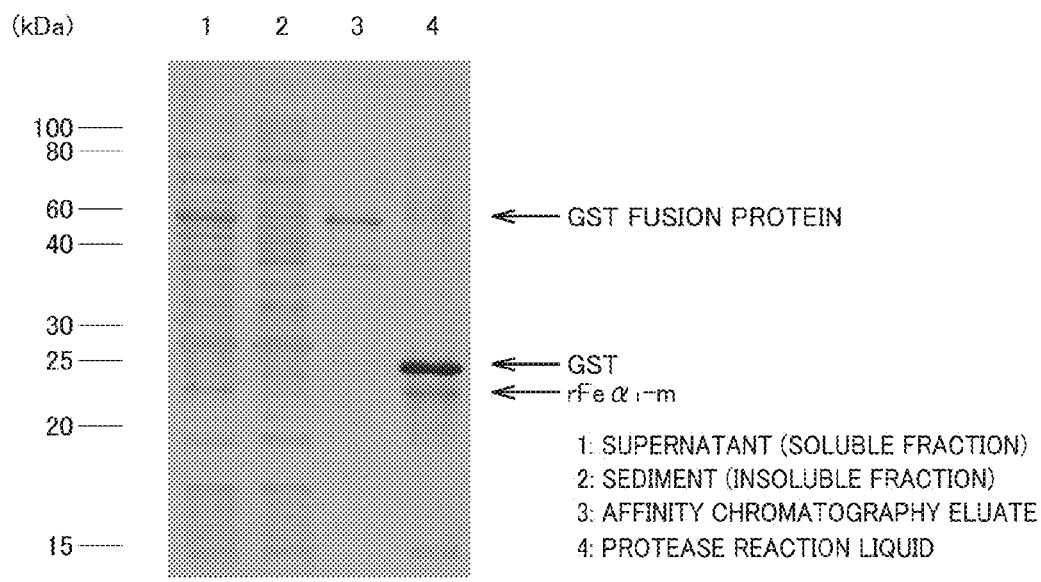
FIG. 36 is a photograph showing a result of SDS-PAGE after expression of GST fusion protein in Experimental Example 8.

E. coli in which expression of GST fusion protein with His-Tag was confirmed was applied on a LB agar medium supplemented with ampicillin, and a colony was picked up and added into 3 mL of a LB liquid medium supplemented with ampicillin and shake-cultured at 37° C. overnight. Sequentially, 3 mL of the culture liquid was added into 250 mL of a LB liquid medium supplemented with ampicillin, and shake-cultured at 37° C. for about 150 minutes, and then added with 2.5 mL of 0.1 mM IPTG, and shake-cultured at 25° C. for about 2 hours. A culture liquid after expression induction of GST fusion protein with His-Tag was centrifuged at 6000×g for 15 minutes, and the resultant sediment was suspended in 20 mL of 50 mM Tris-HCl (pH 8.0) supplemented with 0.5 mM EDTA, 0.4 M NaCl, 5 mM MgCl$_2$, 5% glycerol, 0.5 mM phenylmethylsulfonyl fluoride (PMSF), 1 mM dithiothreitol (DTT) and 1 mg/mL lysozyme, and left still at 4° C. for 1 hour, and freeze-thawed twice. Sequentially, 0.5% of Nonidet P-40 was added, and the mixture was crushed for 20 seconds 5 times by an ultrasonic crusher, and then centrifuged at 9300×g for 20 minutes, and the supernatant and the sediment were analyzed by SDS-PAGE. As a result of electrophoresis, it was revealed that GST fusion protein with His-Tag was contained in the supernatant (FIG. 36).

(6) Affinity Chromatography Method

After dialyzing the supernatant obtained in the above against a binding buffer (20 mM sodium phosphate, 0.5 M NaCl, 10 mM imidazole, pH 7.4) of nickel affinity column (Bio-Scale Mini IMAC Profinity, Bio Rad), the supernatant was applied to the column and washed well with the binding buffer, and eluted with an elution buffer (20 mM sodium phosphate, 0.5 M NaCl, 300 mM imidazole, pH 7.4). Elution was conducted by using a peristaltic pump (SJ-1211L, ATTO) at a flow rate of 0.5 mL/min. Absorbance of the eluate was monitored at an absorption wavelength of 220 nm by using a UV region absorbance monitor (AC-5100L, ATTO), and recorded by a recorder (R-01A, RIKADENKI). In an SDS-PAGE image of the eluate, a plurality of bands including GST fusion protein with His-Tag as a main band were confirmed as shown in FIG. 36. 2 mL of the obtained GST fusion protein with His-Tag eluate was added with DTT in a concentration of 1 mM and mingled, and then put into a dialysis membrane for cutting at a molecular weight of 13 kDa (UC30-32-100, Sanko Junyaku Co., Ltd.) and dialyzed against 2 L of 50 mM Tris-HCl (pH 7.5) supplemented with 150 mM NaCl and 1 mM EDTA for about 6 hours. For the GST fusion protein with His-Tag eluate after dialysis, after protein quantification using DC Protein Assay (Bio-Rad), 1 μL of PreScission Protease (GE Healthcare Bio Science) was added per 200 μg of protein quantity and mingled, and the mixture was reacted at 4° C. for 6 hours or longer. In an SDS-PAGE image after enzymatic cleavage, cleaved GST and feline recombinant $\alpha_1$-m were confirmed. Further, this solution was used as a sample for high performance liquid chromatography (HPLC).

(7) HPLC Method

Figure 37:
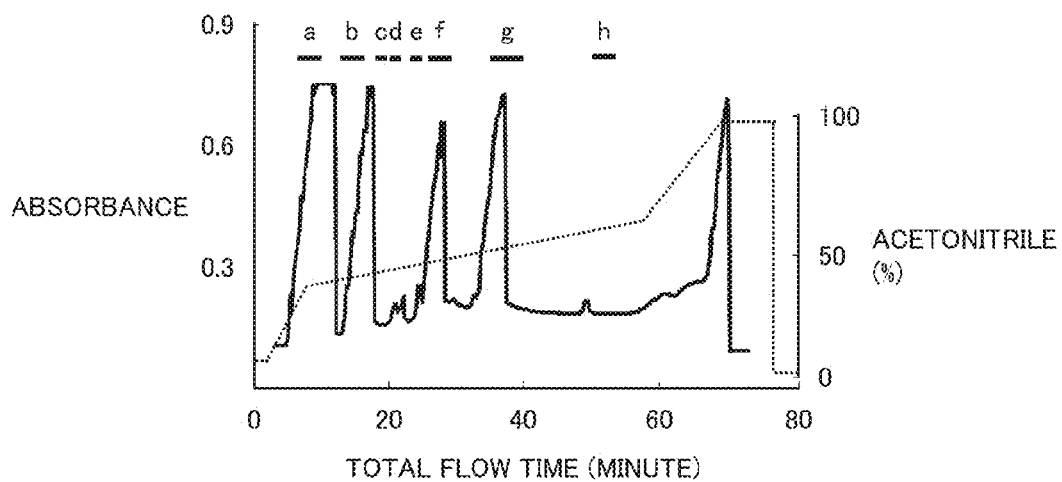
FIG. 37 is a graph showing a chromatographic pattern obtained as a result of HPLC in Experimental Example 8, wherein the left vertical axis represents absorbance at a wavelength of 220 nm, the right vertical axis represents acetonitrile concentration (%), and the horizontal axis represents time (minute).
Figure 38:
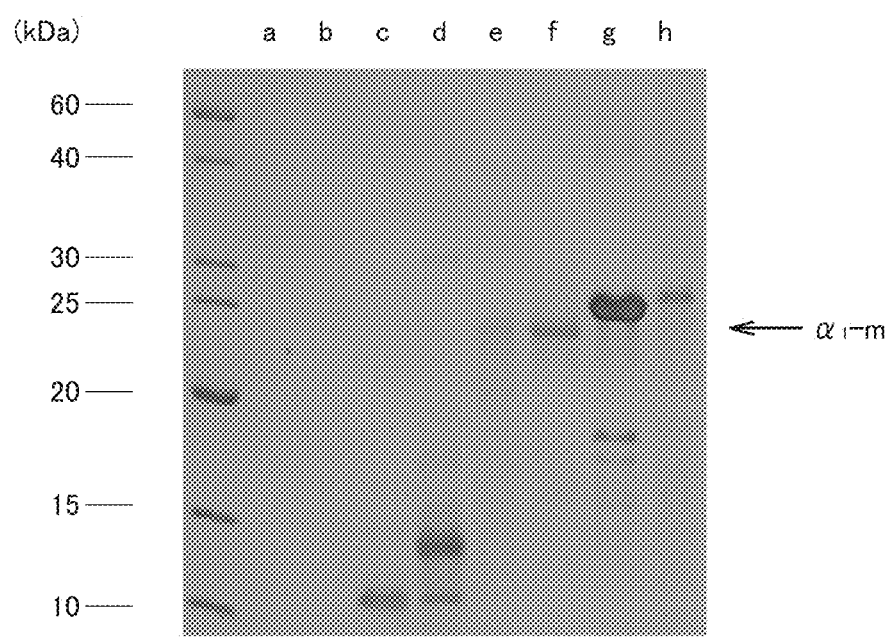
FIG. 38 is a photograph showing a result of SDS-PAGE for major fractions a, b, c, d and e of HPLC in Experimental Example 8.

An HPLC system consists of a system controller (SCL-10A VP, Shimadzu), a liquid sending unit (LC-10AD VP, Shimadzu), a UV region spectrophotometer (SPD-10A VP, Shimadzu), a column oven (CTO-10A VP, Shimadzu) and a deaeration unit (DGU-14A, Shimadzu), and as a column, MightysilRP-18 GP250-4.6 (KANTO CHEMICAL CO., INC) was used. As a separation condition of HPLC, a flow rate of mobile phase of 1 mL/min, and a sample addition amount of 400 μL were used, and for a column equilibrated with a 0.1% trifluoroacetic acid (TFA) solution, a liner gradient of 0 to 80% of acetonitrile concentration was applied using an acetonitrile solution supplemented with 0.1% TFA. The eluate was monitored by its absorbance at an absorption wavelength of 220 nm, and a detected peak was fractionated and centrifuged by a centrifugal concentrator (CC-181, TOMY) for 1 hour, and then dried in a lyophilizer (FDU-540, EYELA) and then stored at −20° C. The chromatography pattern is as shown in FIG. 37, and is generally separated into eight peaks, and protein compositions of respective eluted fractions were analyzed by an SDS-PAGE method. FIG. 38 is a photograph showing a result of SDS-PAGE for major fractions a, b, c, d and e of HPLC. As a result of analysis, as shown in FIG. 38, the target protein was eluted singly in the fraction f. A monoclonal antibody was prepared using this protein as an antigen of recombinant feline $\alpha_1$-m (rFe$\alpha_1$-m).

Experimental Example 9

Preparation of Antibody-Producing Hybridoma, and Anti-rFe$\alpha_1$-m Antibody

For preparing a monoclonal antibody against the protein synthesized in Experimental Example 8 as an antigen of recombinant feline $\alpha_1$-m (rFe$\alpha_1$-m), first, an antibody-producing hybridoma was prepared.

(1) Preparation of Antibody-Producing Hybridoma (1-1) Immunological Method

An immunological method was conducted by subcutaneous injection of purified rFe$\alpha_1$-m as an antigen on a hindlimb footpad of Balb/c mouse. Immunization was conducted 4 times every 5 days, and first to third immunizations were conducted using 200 μL (50 μg/foot) of an antigen liquid that was prepared by mixing equivalent amounts of 100 μL (1 mg/mL) of an antigen solution and an adjuvant, and emulsifying the same, and the last immunization was conducted using only 20 μL (10 μg/foot) of an antigen solution. As the adjuvant, Adjuvant Complete Freund (Wako Pure Chemical Industries, Ltd.) was used in the first immunization, and Adjuvant Incomplete Freund (Wako Pure Chemical Industries, Ltd.) was used in the second to third immunizations.

(1-2) Cell Fusion

After 3 days from the last immunization, a popliteal lymph node was extracted, and after collection of lymphocytes, cell fusion was conducted using GenomONE-CF (ISHIHARA SANGYO KAISHA, LTD.). As a myeloma cell, P3X63-Ag8.653 (Dainippon Sumitomo Pharma Co., Ltd.) was used. A fusion method was conducted according to an attached protocol. Concretely, first, lymphocytes and myeloma cells were mixed at a cell number ratio of 5:1, and centrifuged at 1000 rpm and 4° C. for 5 minutes, and then the supernatant was removed. Then an ice-cooled buffer for fusion was added in an amount of 1 mL per $10^8$ cells of lymphocytes, and suspended uniformly, and then an ice-cooled HVJ-Envelope suspension was added in an amount of 25 μL per 1 mL of the cell mixture. After leaving the cell suspension on ice for 5 minutes, centrifugation at 1000 rpm and 4° C. was conducted for 5 minutes, and the resultant was incubated at 37° C. for 15 minutes in the condition that the supernatant was not removed and the cells were pelletized.

After end of the incubation, a growth medium warmed at 37° C. was added in an amount of 50 mL per $10^8$ cells of lymphocytes, and after suspending, a 96-well plate (96 Well Cell Culture Plate: Greiner bio-one) was seeded with the same in an amount of 100 μL/well. As the growth medium, RPMI1640 (Invitrogen) supplemented with 100,000 IU/mL of penicillin G (PG; Meiji Seika Pharma Co., Ltd.), 100 mg/mL of streptomycin (SM; Meiji Seika Pharma Co., Ltd.), 7.5% Briclone (IL-6, human, BriClone; Cat. No. BR-001, Dainippon Sumitomo Pharma Co., Ltd.), and 10% inactivated fetal bovine serum (FBS; NICHIREI CORPORATION) was used, and operations at the time of addition and suspending were conducted gently. After culturing for 24 hours, the culture medium was replaced with a HAT medium prepared by adding 2% HAT (Invitrogen) to the growth medium as described above.

(2) Screening of Antibody-Producing Hybridoma

For the obtained hybridoma, primary screening using an ELISA method was conducted after 1 week from the cell fusion, and only hybridoma in the well determined as reaction positive as a result of the screening was confirmed by secondary screening using a Western blotting method.

(2-1) Primary Screening

By the ELISA method using rFe$\alpha_1$-m as an antigen, primary screening of an antibody-producing hybridoma was conducted. As an ELISA plate, a 96 Well ELISA Microplate (Greiner bio-one) was used. For washing of the plate, an automated washing machine (Auto Mini Washer AMW-8, BIOTEC Co., Ltd.) was used, and as a washing liquid, PBS (1.37 M NaCl, 27 mM KCl, 100 mM $Na_2HPO_4$, 18 mM $KH_2PO_4$, pH 7.4, 25° C.) was used. As a solid phase, rFe$\alpha_1$-m that was adjusted to be 3 μg/mL by PBS was added to a plate in an amount of 50 μL/well, and allowed to react at 4° C. overnight. After end of the solid phase reaction, the antigen liquid on the plate was removed, and PBS supplemented with 0.5% Bovine Serum Albumin (BSA; Wako Pure Chemical Industries, Ltd.) was added as a blocking liquid in an amount of 150 μL/well, and allowed to react at 37° C. for 60 minutes. After end of the blocking reaction, the plate was washed once, and a culture supernatant of each hybridoma culture was added as a primary antigen in an amount of 50 μL/well, and allowed to react at 37° C. for 60 minutes. After end of the primary antigen reaction, the plate was washed once, and as a secondary antibody, a peroxidase-labeled anti-mouse IgG antibody (SIGMA-ALDRICH) diluted 1000 times with PBS supplemented with 0.1% BSA was added in an amount of 50 μL/well, and allowed to react at 37° C. for 60 minutes. After end of the secondary antibody reaction, the plate was washed 3 times, and as a substrate liquid, PBS supplemented with 0.04% o-phenylenediamine and 0.04% $H_2O_2$ was added in an amount of 150 µL/well, and allowed to react at room temperature under light shielding for 30 to 60 minutes. After end of the substrate reaction, 3 M $H_2SO_4$ was added as a reaction stopper in an amount of 50 µL/well, and the mixture was shaken for 1 minute, and then absorbance at a wavelength of 490 nm was measured by Microplate Reader (Model 550, BIO-RAD). A cell in a positive well showing high absorbance was transferred to a 24-well plate (24 Well Cell Culture Plate; Greiner bio-one) and cultured.

(2-2) Secondary Screening

Secondary screening of an antibody-producing hybridoma was conducted by confirmation by the Western blotting method using $rFe\alpha_1$-m as an antigen. According to the method of Lowry, and using DC Protein Assay Kit (BIO-RAD), absorbance at a wavelength of 655 nm was measured by a Microplate Reader, and protein was quantified. A calibration curve was prepared using BSA. The Western blotting method was conducted in the following manner according to a method of Towbin et al. As a transfer membrane, a polyvinylidene difluoride (PVDF) membrane (BIO-RAD) was used. The PVDF membrane was infiltrated with 100% methanol for 10 seconds, followed by an electrode buffer for transferring (25 mM Tris-HCl (pH 8.3, 20° C.), 192 mM glycine, 5% methanol) for 30 minutes, and then subjected to electrophoresis. A transfer device was assembled by laminating on a positive electrode plate, filter paper (BIO-RAD), a PVDF membrane, gel after end of SDS-PAGE, and filter paper in this order from bottom, and fixing a negative electrode plate thereon. Filter paper was dipped in advance in an electrode buffer for 2 to 3 minutes. The transfer condition was 60 minutes at a constant current of 1.9 mA/cm². The PVDF membrane after end of the transfer was added with 10 mM Tris-HCl (pH 7.5, 20° C.), 140 mM NaCl, 0.01% Tween 20 (TBST) and 0.5% BSA, and shaken at room temperature for 60 minutes, to effect a blocking operation. After end of the blocking, the membrane was washed with TBST for 5 minutes twice under shaking, and a culture supernatant of cell was used as a primary antibody, and allowed to react at room temperature for 90 minutes under shaking. After end of the primary antibody reaction, the membrane was washed with TBST for 5 minutes twice under shaking, and a peroxidase-labeled anti-mouse IgG antibody diluted 1000 times with TBST was reacted at room temperature for 60 minutes under shaking. After end of the secondary antibody reaction, the membrane was washed with TBST for 5 minutes twice under shaking, and allowed to react for 1 to 5 minutes using 0.06% 3,3-diaminobenzidine tetra-hydrochloride, 0.03% $H_2O_2$, and 50 mM Tris-HCl (pH 7.6, 20° C.) as a substrate reaction liquid. After end of the substrate reaction, the reaction was stopped by washing with water, and then the resultant was dried and stored. For a hybridoma showing reaction positivity, cloning was conducted by a limiting dilution method as will be described later.

(3) Cloning

For cloning of hybridoma, a limiting dilution method was used. Concretely, a hybridoma after screening was diluted in a HAT medium so that 2 cells/100 µL was achieved, and seeded in a 96-well plate so that 100 µL/well was achieved. When semi-confluence was achieved, the hybridoma was expansion-cultured on a 24-well plate, and again cultured until semi-confluence was achieved, and then confirmed by the Western blotting method using $rFe\alpha_1$-m as an antigen similarly to the secondary screening. This cloning operation was conducted twice. Also, for preventing the antibody producibility from decreasing due to subculture of the hybridoma for a long period of time, the hybridoma was stored for every cloning using a cell cryopreservation liquid (Cell Banker (BLC-1), JUJI FIELD INC.).

(4) Large Scale Culture of Antibody-Producing Hybridoma and Collection and Purification of Anti-$rFe\alpha_1$-m•mAb A hybridoma having completed cloning was large-scale cultured using a floating cell culture flask (Filter Top SC flask 250 mL 75 cm²; Greiner bio-one). Culture was conducted at 37° C., 5% $CO_2$, for 5 days in a $CO_2$ incubator (JUJI FIELD INC.), and as a medium, a HAT medium was used. The large-scale cultured hybridoma was suspended in serum-free RPMI, and intraperitoneally administered to a nude mouse (Balb/c-nu) in an amount of $2\times10^7$ cells/head. After 10 to 20 days from the administration, a peritoneal fluid was collected. The peritoneal fluid collected from the nude mouse was left still at room temperature for 1 hour or at 4° C. overnight, and then centrifuged at 3000 rpm and 4° C. for 5 minutes, to remove fibrin, hybridoma, erythrocytes and the like in the peritoneal fluid. The separated supernatant was salted out with 50% ammonium sulfate. Concretely, a saturated ammonium sulfate solution in an equivalent amount as the supernatant was gradually dropped under stirring on ice, and stirred for another 1 hour after the dropping. The resultant solution was centrifuged at 10000 rpm and 4° C. for 10 minutes, and the precipitate was dissolved in 20 mM sodium phosphate buffer (pH 7.0). The globulin solution after the salting-out was demineralized using a Sephadex G-25 Fine (GE Healthcare Bio Science) column (inner diameter 1.5 cm, length 30 cm) equilibrated with 20 mM sodium phosphate buffer (pH 7.0). Flow rate of the chromatography was adjusted to 0.5 mL/min by a peristaltic pump (SJ-1211L, ATTO). The globulin solution after demineralization was purified by an affinity chromatography method using Protein G Sepharose 4 Fast Flow (GE Healthcare Bio Science) charged in Eco column (inner diameter 2.5 cm, length 10.0 cm: BIO-RAD). Concretely, the globulin solution after demineralization was added to a column equilibrated with 20 mM sodium phosphate buffer (pH 7.0) at a flow rate of 0.5 mL/min, and then the column was eluted with 100 mM glycine (pH 3.0). The eluate was immediately neutralized with one-tenth amount of 1 M Tris-HCl (pH 9.0). The eluate after purification was demineralized by a Sephadex G-25 Fine column (inner diameter 2 cm, length 30 cm) equilibrated with 50 mM ammonium acetate (pH 7.0), and then lyophilized by using Freeze Dryer (FDU540, EYELA TOKYO RIKAKIKAI CO., LTD.), and stored at −20° C.

(5) Determination of Isotype

Using a Mouse Monoclonal Isotyping Kit (COSMO BIO co., ltd.), isotype of the obtained anti-$rFe\alpha_1$-m•mAb was determined according to an attached protocol. Concretely, 150 µL an anti-$rFe\alpha_1$-m•mAb sample was added to a development tube, and incubated at room temperature for 30 seconds, and then stirred. To this, an isotyping strip was introduced, and the sample was further incubated at room temperature for 10 to 15 minutes, and then a class and a subclass were read out. As the anti-$rFe\alpha_1$-m•mAb sample, the one prepared by diluting a culture supernatant of hybridoma having completed the second cloning 10 times with PBS supplemented with 1% BSA was used. Two kinds of monoclonal antibodies were obtained, and isotype of one antibody E was κ chain of IgG1, and isotype of the other antibody F was κ chain of IgG2b.

(6) Specificity to Feline Native α₁-m

For antibodies E and F, specificity to feline native α₁-m was confirmed by using a Western blotting method using urinary protein of cat suffering from chronic kidney disease (CKD) as an antigen. The Western blotting method was executed in a similar manner as described above. As a urinary protein sample for loading in SDS-PAGE, the one prepared by cutting SS bonds in feline urinary protein with 2-Mercaptoethanol was used. FIG. 31 is a photograph showing an experimental result of specificity of antibodies E and F to feline native α₁-m, and lane 1 represents rFeα₁-m, and lane 2 represents urinary protein of CKD cat. As shown in FIG. 31, both antibodies E and F were confirmed to specifically react with native α₁-m.

It is to be noted that embodiments and examples disclosed herein are given for exemplification in every respect, and not for restriction. It is intended that the scope of the present invention is indicated by claims rather than by the foregoing description, and involves every modification within the equivalent meaning and range of claims.

The invention claimed is:

1. An isolated antibody specifically binding to SEQ ID No: 1 of feline-derived cystatin C, wherein said antibody is produced by a cell line Mouse-Mouse hybridoma CysC mAb1, Accession No.: FERM P-21877.

2. The antibody of claim 1, wherein said feline-derived cystatin C consists of the amino acid of SEQ ID NO: 1.

3. An isolated antibody specifically binding to SEQ ID No: 1 of feline-derived cystatin C, wherein said antibody is produced by a cell line Mouse-Mouse hybridoma CysC mAb2, Accession No.: FERM P-21878.

4. The antibody of claim 3, wherein said feline-derived cystatin C consists of the amino acid of SEQ ID NO: 1.

5. A cell line Mouse-Mouse hybridoma CysC mAb1, Accession No.: FERM P-21877.

6. A cell line Mouse-Mouse hybridoma CysC mAb2, Accession No.: FERM P-21878.

* * * * *

```
                        SEQUENCE LISTING

<160> NUMBER OF SEQ ID NOS: 88

<210> SEQ ID NO 1
<211> LENGTH: 147
<212> TYPE: PRT
<213> ORGANISM: Felis silvestris catus

<400> SEQUENCE: 1

Met Ala Gly Ser Leu Arg Thr Pro Leu Leu Leu Leu Ala Ala Val Ala
1               5                   10                  15

Leu Thr Leu Ala Leu Ala Met Ser Pro Gly Thr Gly Arg Arg Asn Asn
                20                  25                  30

Lys Ser Ala Leu Val Gly Ala Pro Leu Asp Ala Asp Val Asn Glu Glu
            35                  40                  45

Gly Val Gln Gln Ala Leu Asn Phe Ala Leu Ser Glu Tyr Asn Lys Ala
        50                  55                  60

Ser Asn Asp Ala Tyr His Ser Arg Ala Met Arg Val Val Arg Ala Arg
65                  70                  75                  80

Lys Gln Val Val Ala Gly Met Asn Tyr Phe Leu Asp Val Glu Ile Gly
                85                  90                  95

Arg Thr Arg Cys Thr Lys Ser Gln Pro Asn Leu Asp Thr Cys Pro Phe
                100                 105                 110

His Asp Gln Pro His Leu Met Arg Lys Thr Leu Cys Ser Phe Gln Ile
            115                 120                 125

Tyr Thr Val Pro Trp Met Gly Lys Thr Ser Leu Val Lys Ser Ser Cys
        130                 135                 140

Gln Asp Ala
145

<210> SEQ ID NO 2
<211> LENGTH: 444
<212> TYPE: DNA
<213> ORGANISM: Felis silvestris catus
<220> FEATURE:
<221> NAME/KEY: CDS
<222> LOCATION: (1)..(444)

<400> SEQUENCE: 2 atg gcc ggg tcc ttg cgc acc ccg ctg ctc ctg cta gcc gct gtg gcc        48
Met Ala Gly Ser Leu Arg Thr Pro Leu Leu Leu Leu Ala Ala Val Ala
1               5                   10                  15 ctg act ctg gcc ctg gct atg agt ccc ggg acc ggc agg aga aac aac        96
Leu Thr Leu Ala Leu Ala Met Ser Pro Gly Thr Gly Arg Arg Asn Asn
                20                  25                  30 aag tct gcg ctg gtg ggc gcc ccg ttg gat gcc gac gtc aac gag gag       144
Lys Ser Ala Leu Val Gly Ala Pro Leu Asp Ala Asp Val Asn Glu Glu
            35                  40                  45 ggc gtg cag cag gcg ctg aac ttc gcc ctc agc gag tac aac aag gcg       192
Gly Val Gln Gln Ala Leu Asn Phe Ala Leu Ser Glu Tyr Asn Lys Ala
```

```
agc aac gac gcg tac cac agc cgt gcg atg cgg gta gtg cgt gcc cga    240
Ser Asn Asp Ala Tyr His Ser Arg Ala Met Arg Val Val Arg Ala Arg
 65              70                  75                  80 aag cag gtc gtg gct ggg atg aac tac ttc ttg gac gtg gag att gga    288
Lys Gln Val Val Ala Gly Met Asn Tyr Phe Leu Asp Val Glu Ile Gly
                 85                  90                  95 cga acc aga tgt acc aag tcc cag ccc aac ttg gac acc tgt ccc ttt    336
Arg Thr Arg Cys Thr Lys Ser Gln Pro Asn Leu Asp Thr Cys Pro Phe
            100                 105                 110 cat gac cag ccg cac ctg atg agg aaa acg ctc tgc tct ttc cag ata    384
His Asp Gln Pro His Leu Met Arg Lys Thr Leu Cys Ser Phe Gln Ile
                115                 120                 125 tac act gta ccc tgg atg ggc aag aca tcc ctg gtg aag tcc agc tgc    432
Tyr Thr Val Pro Trp Met Gly Lys Thr Ser Leu Val Lys Ser Ser Cys
130                 135                 140 cag gat gca tag                                                    444
Gln Asp Ala
145
```

<210> SEQ ID NO 3
<211> LENGTH: 18
<212> TYPE: DNA
<213> ORGANISM: Artificial Sequence
<220> FEATURE:
<223> OTHER INFORMATION: Synthetic Upper Primer 1
<220> FEATURE:
<221> NAME/KEY: misc_feature
<222> LOCATION: (1)..(1)
<223> OTHER INFORMATION: s is g or c
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (4)..(4)
<223> OTHER INFORMATION: s is g or c
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (11)..(11)
<223> OTHER INFORMATION: w is a or t
<220> FEATURE:
<221> NAME/KEY: misc_feature
<222> LOCATION: (18)..(18)
<223> OTHER INFORMATION: r is a or g

<400> SEQUENCE: 3
sgwsrgcgat wcaacaar                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic Lower Primer 1
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (8)..(8)
<223> OTHER INFORMATION: s is g or c
<220> FEATURE:
<221> NAME/KEY: misc_feature
<222> LOCATION: (13)..(13)

```
<223> OTHER INFORMATION: y is c or t
<220> FEATURE:
<221> NAME/KEY: misc_feature
<222> LOCATION: (17)..(17)
<223> OTHER INFORMATION: r is a or g
<220> FEATURE:
<221> NAME/KEY: misc_feature
<222> LOCATION: (18)..(18)
<223> OTHER INFORMATION: m is a or c

<400> SEQUENCE: 4
ctgrcagstg gayttcrm                                                   18

<210> SEQ ID NO 5
<211> LENGTH: 265
<212> TYPE: DNA
<213> ORGANISM: Artificial Sequence
<220> FEATURE:
<223> OTHER INFORMATION: Synthetic Nucleotide sequence of amplified
      products by PCR using Upper Primer 1 and Lower Primer 1

<400> SEQUENCE: 5
cctcagcgag tacaacaagg cgagcaacga cgcgtaccac agccgtgcga tgcgggtagt     60
gcgtgcccga aagcaggtcg tggctgggat gaactacttc ttggacgtgg agattggacg   120
aaccagatgt accaagtccc agcccaactt ggacacctgt ccctttcatg accagccgca   180
cctgatgagg aaaacgctct gctctttcca gatatacact gtaccctgga tgggcaagac   240
atccctggtg aagtccagct gccag                                        265

<210> SEQ ID NO 6
<211> LENGTH: 30
<212> TYPE: RNA
<213> ORGANISM: Artificial Sequence
<220> FEATURE:
<223> OTHER INFORMATION: Synthetic Oligo-RNA

<400> SEQUENCE: 6
agcaucgagu cggccuuguu ggccuacugg                                     30

<210> SEQ ID NO 7
<211> LENGTH: 28
<212> TYPE: DNA
<213> ORGANISM: Artificial Sequence
<220> FEATURE:
<223> OTHER INFORMATION: Synthetic Primer

<400> SEQUENCE: 7
aactggaaga attcgcggcc gcaggaat                                       28

<210> SEQ ID NO 8
<211> LENGTH: 21
<212> TYPE: DNA
<213> ORGANISM: Artificial Sequence
<220> FEATURE:
<223> OTHER INFORMATION: Synthetic 5'RACE-Upper Primer

<400> SEQUENCE: 8
agcatcgagt cggccttgtt g                                              21

<210> SEQ ID NO 9
<211> LENGTH: 25
<212> TYPE: DNA
<213> ORGANISM: Artificial Sequence
<220> FEATURE:
<223> OTHER INFORMATION: Synthetic 5'RACE-Lower Primer

<400> SEQUENCE: 9
```
ttcatcccag ccacgacctg ctttc                                          25

<210> SEQ ID NO 10
<211> LENGTH: 351
<212> TYPE: DNA
<213> ORGANISM: Artificial Sequence
<220> FEATURE:
<223> OTHER INFORMATION: Synthetic Nucleotide sequence of amplified
      products by 5'RACE-PCR

<400> SEQUENCE: 10
agcatcgagt cggccttgtt ggcctactgg ttatctacgt tggatcactt cctacggtaa    60
cctgtgcgct gtcgatcgcg aacacaccat ggccgggtcc ttgcgcaccc cgctgctcct   120
gctagccgct gtggccctga ctctggccct ggctatgagt cccggaccg gcaggagaaa    180 caacaagtct gcgctggtgg gcgccccgtt ggatgccgac gtcaacgagg agggcgtgca   240
gcaggcgctg aacttcgccc tcagcgagta caacaaggcg agcaacgacg cgtaccacag   300
ccgtgcgatg cgggtagtgc gtgcccgaaa gcaggtcgtg gctgggatga a             351

<210> SEQ ID NO 11
<211> LENGTH: 27
<212> TYPE: DNA
<213> ORGANISM: Artificial Sequence
<220> FEATURE:
<223> OTHER INFORMATION: Synthetic 3'RACE-Upper Primer

<400> SEQUENCE: 11
gctctttcca gatatacact gtaccct                                        27

<210> SEQ ID NO 12
<211> LENGTH: 22
<212> TYPE: DNA
<213> ORGANISM: Artificial Sequence
<220> FEATURE:
<223> OTHER INFORMATION: Synthetic 3'RACE-Lower Primer

<400> SEQUENCE: 12
agaattcgcg gccgcaggaa tt                                             22

<210> SEQ ID NO 13
<211> LENGTH: 388
<212> TYPE: DNA
<213> ORGANISM: Artificial Sequence
<220> FEATURE:
<223> OTHER INFORMATION: Synthetic Nucleotide sequence of amplified
      products by 3'RACE-PCR

<400> SEQUENCE: 13
gctctttcca gatatacact gtaccctgga tgggcaagac atccctggtg aagtccagct    60
gccaggatgc atagaggacc ctgtgacagg ctgggttgct ctggccccct tctcccaccc   120
cactctcccc ttgtagaact cctaatcctt ggaagggtgg ccctgtccag gtgatgtccc   180
ctcagtgtgc tggtcccagg aggcaaatag aaaagggttc tggggcattt tctgaacagc   240
taagtgactg tagctccttt cttttaattg tttttccaaa tgtaccagta tgtagtgcac   300
ttgttctgct ctatcttcat caataaaaag taagatcagc taaaaaaaaa aaaaaaaaa    360 aaaaaaatt cctgcggccg cgaattct                                       388

<210> SEQ ID NO 14
<211> LENGTH: 796
<212> TYPE: DNA
<213> ORGANISM: Artificial Sequence -continued

```
<220> FEATURE:
<223> OTHER INFORMATION: Synthetic Full length FeCysC nucleotide
      sequence

<400> SEQUENCE: 14
ttatctacgt tggatcactt cctacggtaa cctgtgcgct gtcgatcgcg aacacaccat      60
ggccgggtcc ttgcgcaccc cgctgctcct gctagccgct gtggccctga ctctggccct     120
ggctatgagt cccgggaccg gcaggagaaa caacaagtct cgctggtgg gcgcccgtt      180 ggatgccgac gtcaacgagg agggcgtgca gcaggcgctg aacttcgccc tcagcgagta     240
caacaaggcg agcaacgacg cgtaccacag ccgtgcgatg cgggtagtgc gtgcccgaaa     300
gcaggtcgtg gctgggatga actacttctt ggacgtggag attggacgaa ccagatgtac     360
caagtcccag cccaacttgg acacctgtcc ctttcatgac cagccgcacc tgatgaggaa     420
aacgctctgc tctttccaga tatacactgt accctggatg ggcaagacat ccctggtgaa     480
gtccagctgc caggatgcat agaggaccct gtgacaggct gggttgctct ggccccttc      540 tcccacccca ctctccccct tgtagaactc taatccttgg aagggtggcc ctgtccaggt     600
gatgtcccct cagtgtgctg gtcccaggag gcaaatagaa aagggttctg ggcatttc      660 tgaacagcta agtgactgta gctcctttct tttaattgtt tttccaaatg taccagtatg     720
tagtgcactt gttctgctct atcttcatca ataaaaagta agatcagcta aaaaaaaaa      780 aaaaaaaaaa aaaaaa                                                     796

<210> SEQ ID NO 15
<211> LENGTH: 30
<212> TYPE: DNA
<213> ORGANISM: Artificial Sequence
<220> FEATURE:
<223> OTHER INFORMATION: Synthetic Upper Primer

<400> SEQUENCE: 15
cacgaattca ccggcaggag aaacaacaag                                       30

<210> SEQ ID NO 16
<211> LENGTH: 39
<212> TYPE: DNA
<213> ORGANISM: Artificial Sequence
<220> FEATURE:
<223> OTHER INFORMATION: Synthetic Lower Primer

<400> SEQUENCE: 16
cacctcgagt tatgcatcct ggcagctgga cttcaccag                             39

<210> SEQ ID NO 17
<211> LENGTH: 118
<212> TYPE: PRT
<213> ORGANISM: Felis silvestris catus

<400> SEQUENCE: 17

Met Ala Arg Phe Val Val Leu Val Leu Leu Gly Leu Leu Tyr Leu Ser
1               5                   10                  15

His Leu Asp Ala Val Gln His Ser Pro Lys Val Gln Val Tyr Ser Arg
            20                  25                  30

His Pro Ala Glu Asn Gly Lys Pro Asn Phe Leu Asn Cys Tyr Val Ser
        35                  40                  45

Gly Phe His Pro Pro Gln Ile Asp Ile Thr Leu Met Lys Asn Gly Lys
    50                  55                  60

Lys Met Glu Ala Glu Gln Thr Asp Leu Ser Phe Asn Arg Asp Trp Thr
65                  70                  75                  80
```

```
Phe Tyr Leu Leu Val His Thr Glu Phe Thr Pro Thr Val Glu Asp Glu
                85                  90                  95

Tyr Ser Cys Gln Val Asn His Thr Thr Leu Ser Glu Pro Lys Val Val
            100                 105                 110

Met Trp Glu Arg Asp Thr
        115

<210> SEQ ID NO 18
<211> LENGTH: 357
<212> TYPE: DNA
<213> ORGANISM: Felis silvestris catus
<220> FEATURE:
<221> NAME/KEY: CDS
<222> LOCATION: (1)..(357)

<400> SEQUENCE: 18 atg gcg cgt ttt gtg gtc ttg gtc ctg ctc gga ctg ctc tat ctg tcc      48
Met Ala Arg Phe Val Val Leu Val Leu Leu Gly Leu Leu Tyr Leu Ser
1               5                   10                  15 cac ctg gat gcc gtc cag cat tct cca aag gtt cag gtt tac tcc cgt      96
His Leu Asp Ala Val Gln His Ser Pro Lys Val Gln Val Tyr Ser Arg
            20                  25                  30 cac cca gca gag aat gga aag cca aat ttt ctg aac tgc tac gtt tcg     144
His Pro Ala Glu Asn Gly Lys Pro Asn Phe Leu Asn Cys Tyr Val Ser
        35                  40                  45 ggg ttc cac cca cca caa att gat atc acc ttg atg aag aat gga aag     192
Gly Phe His Pro Pro Gln Ile Asp Ile Thr Leu Met Lys Asn Gly Lys
    50                  55                  60 aag atg gaa gcg gag cag aca gat ctg tcc ttc aac agg gac tgg act     240
Lys Met Glu Ala Glu Gln Thr Asp Leu Ser Phe Asn Arg Asp Trp Thr
65                  70                  75                  80 ttc tat ctt ctg gtc cac acc gaa ttt act ccc act gtc gaa gat gag     288
Phe Tyr Leu Leu Val His Thr Glu Phe Thr Pro Thr Val Glu Asp Glu
                85                  90                  95 tat agc tgc cag gtg aat cat act act ctc agt gag ccc aag gtc gtt     336
Tyr Ser Cys Gln Val Asn His Thr Thr Leu Ser Glu Pro Lys Val Val
            100                 105                 110 atg tgg gag cga gat acg taa                                         357
Met Trp Glu Arg Asp Thr
        115

<210> SEQ ID NO 19
<211> LENGTH: 20
<212> TYPE: DNA
<213> ORGANISM: Artificial Sequence
<220> FEATURE:
<223> OTHER INFORMATION: Synthetic Upper Primer 1

<400> SEQUENCE: 19
ggaaagtcaa ataacctgaa                                                20

<210> SEQ ID NO 20
<211> LENGTH: 21
<212> TYPE: DNA
<213> ORGANISM: Artificial Sequence
<220> FEATURE:
<223> OTHER INFORMATION: Synthetic Lower Primer 1

<400> SEQUENCE: 20
tctcgatccc acttaactat c                                              21

<210> SEQ ID NO 21
<211> LENGTH: 239
```

```
<212> TYPE: DNA
<213> ORGANISM: Artificial Sequence
<220> FEATURE:
<223> OTHER INFORMATION: Synthetic Nucleotide sequence of amplified
      products by PCR using Upper Primer 1 and Lower Primer 1

<400> SEQUENCE: 21
ggaaagccaa atttcctgaa ctgctacgtt tcggggttcc acccaccaca aattgatatc      60
accttgatga agaatggaaa gaagatggaa gcggaacaga cagatctgtc cttcaacagg    120
gactggactt tctatcttct ggtccacacc gaatttactc ccactgtcga agatgagtat    180
agctgccaag tgaatcatac tactctcagt gagcccaaga tagttaagtg ggatcgaga    239

<210> SEQ ID NO 22
<211> LENGTH: 26
<212> TYPE: DNA
<213> ORGANISM: Artificial Sequence
<220> FEATURE:
<223> OTHER INFORMATION: Synthetic Upper Primer 2

<400> SEQUENCE: 22
gggttccacc caccaacaat tcaaat                                          26

<210> SEQ ID NO 23
<211> LENGTH: 14
<212> TYPE: DNA
<213> ORGANISM: Artificial Sequence
<220> FEATURE:
<223> OTHER INFORMATION: Synthetic Upper Primer 3

<400> SEQUENCE: 23
tggtccacac cgaa                                                       14

<210> SEQ ID NO 24
<211> LENGTH: 22
<212> TYPE: DNA
<213> ORGANISM: Artificial Sequence
<220> FEATURE:
<223> OTHER INFORMATION: Synthetic Lower Primer 3

<400> SEQUENCE: 24
gaaaatatga aatacgtgta tt                                              22

<210> SEQ ID NO 25
<211> LENGTH: 23
<212> TYPE: DNA
<213> ORGANISM: Artificial Sequence
<220> FEATURE:
<223> OTHER INFORMATION: Synthetic Universal Primer A Mix

<400> SEQUENCE: 25
aagcagtggt atcaacgcag agg                                             23

<210> SEQ ID NO 26
<211> LENGTH: 160
<212> TYPE: DNA
<213> ORGANISM: Artificial Sequence
<220> FEATURE:
<223> OTHER INFORMATION: Synthetic Nucleotide sequence of amplified
      products by PCR using Upper Primer 3 and Lower Primer 3

<400> SEQUENCE: 26
tggtccacac cgaatttact cccacgttga agatgagtat aggctgccag gtgaatcata     60
ctactctcag tgagcccaag gtcgttatgt gggagcgaga tacgtaacca gcatcatgga   120
ggtttgaaga tggtgcattt aaattggact attcccaaat                          160
```

<210> SEQ ID NO 27
<211> LENGTH: 25
<212> TYPE: DNA
<213> ORGANISM: Artificial Sequence
<220> FEATURE:
<223> OTHER INFORMATION: Synthetic Lower Primer 4

<400> SEQUENCE: 27
gtgtggacca gaagatagaa agtcc                                          25

<210> SEQ ID NO 28
<211> LENGTH: 22
<212> TYPE: DNA
<213> ORGANISM: Artificial Sequence
<220> FEATURE:
<223> OTHER INFORMATION: Synthetic 5' RACE Primer

<400> SEQUENCE: 28
gtctaccagg cattcgcttc at                                             22

<210> SEQ ID NO 29
<211> LENGTH: 260
<212> TYPE: DNA
<213> ORGANISM: Artificial Sequence
<220> FEATURE:
<223> OTHER INFORMATION: Synthetic Nucleotide sequence of amplified
      products by PCR using 5'RACE Primer 1 and Lower Primer 4

<400> SEQUENCE: 29
atggcgcgtt ttgtggtctt ggtcctgctc ggactgctct atctgtccca cctggatgcc     60
gtccagcatt ctccaaaggt tcaggtttac tcccgtcacc cagcagagaa tggaaagcca    120
aattttctga actgctacgt ttcggggttc caccaccac aaattgatat caccttgatg     180
aagaatggaa agaagatgga agcggagcag acagatctgt ccttcaacag ggactggact    240
ttctatcttc tggtccacac                                               260

<210> SEQ ID NO 30
<211> LENGTH: 33
<212> TYPE: DNA
<213> ORGANISM: Artificial Sequence
<220> FEATURE:
<223> OTHER INFORMATION: Synthetic Upper Primer
<220> FEATURE:
<221> NAME/KEY: misc_feature
<222> LOCATION: (1)..(1)
<223> OTHER INFORMATION: n is t or a or c or g
<220> FEATURE:
<221> NAME/KEY: misc_feature
<222> LOCATION: (2)..(2)
<223> OTHER INFORMATION: n is t or a or c or g
<220> FEATURE:
<221> NAME/KEY: misc_feature
<222> LOCATION: (3)..(3)
<223> OTHER INFORMATION: n is t or a or c or g

<400> SEQUENCE: 30
nnnggatccg tccagcattc caaaggttca ggt                                 33

<210> SEQ ID NO 31
<211> LENGTH: 39
<212> TYPE: DNA
<213> ORGANISM: Artificial Sequence
<220> FEATURE:
<223> OTHER INFORMATION: Synthetic Lower Primer
<220> FEATURE:
<221> NAME/KEY: misc_feature
<222> LOCATION: (1)..(1)

```
<223> OTHER INFORMATION: n is t or a or c or g
<220> FEATURE:
<221> NAME/KEY: misc_feature
<222> LOCATION: (2)..(2)
<223> OTHER INFORMATION: n is t or a or c or g
<220> FEATURE:
<221> NAME/KEY: misc_feature
<222> LOCATION: (3)..(3)
<223> OTHER INFORMATION: n is t or a or c or g

<400> SEQUENCE: 31
nnngtcgact tacatgtctc gatcccactt aacgacctt                          39

<210> SEQ ID NO 32
<211> LENGTH: 201
<212> TYPE: PRT
<213> ORGANISM: Felis silvestris catus

<400> SEQUENCE: 32

Met Arg Ser Leu Arg Ala Leu Phe Leu Leu Val Thr Ala Cys Leu Ala
1               5                   10                  15

Val Ser Ala Ser Pro Val Leu Thr Pro Pro Asp Asp Ile Gln Val Gln
            20                  25                  30

Glu Asn Phe Asp Ile Ser Arg Ile Tyr Gly Lys Trp Phe His Val Ala
        35                  40                  45

Met Gly Ser Thr Cys Pro Trp Leu Lys Lys Phe Met Asp Arg Met Ser
    50                  55                  60

Met Ser Thr Leu Val Leu Gly Glu Gly Ala Lys Asp Lys Glu Ile Ser
65                  70                  75                  80

Met Thr Ser Thr Arg Trp Arg Arg Gly Thr Cys Glu Glu Ile Ser Gly
                85                  90                  95

Ala Tyr Glu Lys Thr Asp Thr Asp Gly Lys Phe Leu Tyr His Lys Pro
            100                 105                 110

Arg Trp Asn Ile Thr Met Glu Ser Tyr Val Val His Thr Asn Tyr Asp
        115                 120                 125

Glu Tyr Ala Ile Leu Leu Thr Lys Lys Phe Ser His His His Gly Pro
    130                 135                 140

Thr Ile Thr Ala Lys Leu Tyr Gly Arg Gln Pro Gln Leu Arg Glu Ser
145                 150                 155                 160

Leu Leu Glu Glu Phe Arg Glu Val Ala Leu Gly Val Gly Ile Pro Glu
                165                 170                 175

Asp Ser Ile Phe Thr Met Ala Asp Lys Gly Glu Cys Val Pro Gly Glu
            180                 185                 190

Gln Glu Pro Glu Pro Ser Pro Leu Thr
        195                 200

<210> SEQ ID NO 33
<211> LENGTH: 603
<212> TYPE: DNA
<213> ORGANISM: Felis silvestris catus
<220> FEATURE:
<221> NAME/KEY: CDS
<222> LOCATION: (1)..(603)

<400> SEQUENCE: 33 atg agg agc ctc agg gct ctg ttt ctg ctg gtg act gcc tgc ctg gcg   48
Met Arg Ser Leu Arg Ala Leu Phe Leu Leu Val Thr Ala Cys Leu Ala
1               5                   10                  15 gtg agt gcc agc ccc gtg ctg acg ccg ccc gat gac atc caa gtg caa   96
Val Ser Ala Ser Pro Val Leu Thr Pro Pro Asp Asp Ile Gln Val Gln
            20                  25                  30
```

```
gag aac ttc gac atc tct agg atc tac ggg aag tgg ttc cac gtg gcc      144
Glu Asn Phe Asp Ile Ser Arg Ile Tyr Gly Lys Trp Phe His Val Ala
         35                  40                  45 atg ggc tcc acc tgc ccg tgg ctg aag aag ttc atg gac agg atg tcc      192
Met Gly Ser Thr Cys Pro Trp Leu Lys Lys Phe Met Asp Arg Met Ser
 50                  55                  60 atg agc acg ctg gtg ctg ggc gag ggg gcg aag gac aag gag atc agc      240
Met Ser Thr Leu Val Leu Gly Glu Gly Ala Lys Asp Lys Glu Ile Ser
 65                  70                  75                  80 atg acc agc act cgt tgg cgg aga ggc acc tgc gag gag atc tcc ggg      288
Met Thr Ser Thr Arg Trp Arg Arg Gly Thr Cys Glu Glu Ile Ser Gly
                 85                  90                  95 gct tat gag aaa aca gac act gac gga aag ttc ctc tat cat aag cct      336
Ala Tyr Glu Lys Thr Asp Thr Asp Gly Lys Phe Leu Tyr His Lys Pro
            100                 105                 110 aga tgg aac atc acc atg gag tcc tat gtg gtc cac acc aac tat gac      384
Arg Trp Asn Ile Thr Met Glu Ser Tyr Val Val His Thr Asn Tyr Asp
        115                 120                 125 gag tac gcc atc ctt ctg acc aag aaa ttc agc cac cac cac ggg ccc      432
Glu Tyr Ala Ile Leu Leu Thr Lys Lys Phe Ser His His His Gly Pro
    130                 135                 140 acc att acc gcc aag ctc tat ggg cga cag cca cag ctt cga gaa agc      480
Thr Ile Thr Ala Lys Leu Tyr Gly Arg Gln Pro Gln Leu Arg Glu Ser
145                 150                 155                 160 ctg ctg gag gag ttc agg gag gtc gcc ttg ggc gtg ggc atc ccc gag      528
Leu Leu Glu Glu Phe Arg Glu Val Ala Leu Gly Val Gly Ile Pro Glu
                165                 170                 175 gac tcc atc ttc acg atg gcc gac aaa ggt gag tgt gtc cct ggg gag      576
Asp Ser Ile Phe Thr Met Ala Asp Lys Gly Glu Cys Val Pro Gly Glu
            180                 185                 190 cag gaa cca gag ccc tct cca ctc acg                                  603
Gln Glu Pro Glu Pro Ser Pro Leu Thr
        195                 200
```

<210> SEQ ID NO 34
<211> LENGTH: 17
<212> TYPE: DNA
<213> ORGANISM: Artificial Sequence
<220> FEATURE:
<223> OTHER INFORMATION: Synthetic Upper Primer 1
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (13)..(13)
<223> OTHER INFORMATION: r is a or g

<400> SEQUENCE: 34
ccargtgcag garaact                                                    17

<210> SEQ ID NO 35
<211> LENGTH: 24
<212> TYPE: DNA
<213> ORGANISM: Artificial Sequence
<220> FEATURE:
<223> OTHER INFORMATION: Synthetic Lower Primer 1
<220> FEATURE:
<221> NAME/KEY: misc_feature
<222> LOCATION: (16)..(16)
<223> OTHER INFORMATION: y is c or t
<220> FEATURE:
<221> NAME/KEY: misc_feature
<222> LOCATION: (18)..(18)
<223> OTHER INFORMATION: k is g or t
<220> FEATURE:

```
<221> NAME/KEY: misc_feature
<222> LOCATION: (22)..(22)
<223> OTHER INFORMATION: v is g or a or c

<400> SEQUENCE: 35
cttctchgag tagaaytkgt tvcc                                            24

<210> SEQ ID NO 36
<211> LENGTH: 912
<212> TYPE: DNA
<213> ORGANISM: Artificial Sequence
<220> FEATURE:
<223> OTHER INFORMATION: Synthetic Nucleotide sequence of amplified
      products by PCR using Upper Primer 1 and Lower Primer 1

<400> SEQUENCE: 36
ccaagtgcaa gagaacttcg acatctctag gatctacggg aagtggttcc acgtggccat     60
gggctccacc tgcccgtggc tgaagaagtt catggacagg atgtcctga gcacgctggt    120 gctgggcgag ggggcgaagg acaaggagat cagcatgacc agcactcgtt ggcggagagg    180
cacctgcgag gagatctccg gggcttatga gaaaacagac actgacggaa agttcctcta    240
tcataagcct agatggaaca tcaccatgga gtcctatgtg gtccacacca actatgacga    300
gtacgccatc cttctgacca agaaattcag ccaccaccac gggcccacca ttaccgccaa    360
gctctatggg cgacagccac agcttcgaga aagcctgctg gaggagttca gggaggtcgc    420
cttgggcgtg ggcatccccg aggactccat cttcacgatg gccgacaaag gtgagtgtgt    480
ccctggggag caggaaccag agccctctcc actcacgaga gccggcgggc tgtgctgcc     540 ccaggaagag gaaggatcag gggccaggct gctagcaact gatttcagca agaaggaaga    600
tgcctgccag ctgggccacg cagaaggccc ttgcctgggg atggtcacga ggtatttcta    660
taatggctca tccatggcct gtgagacctt ccaatatggc ggctgcctgg caacggcaa     720 caacttcgcc tcagagaagg ggtgtctgca gacctgccga accgtggcgg cctgcaacct    780
ccccatagtg accggccct gccgaggcta caaccagctc tgggcattcg atgccgtcca    840
ggggaaatgc gtcctcttca cctacggcgg ctgccaaggc aacggcagca agttctactc    900
agagaaggag tg                                                         912

<210> SEQ ID NO 37
<211> LENGTH: 30
<212> TYPE: RNA
<213> ORGANISM: Artificial Sequence
<220> FEATURE:
<223> OTHER INFORMATION: Synthetic Oligo RNA

<400> SEQUENCE: 37
agcaucgagu cggccuuguu ggccuacugg                                      30

<210> SEQ ID NO 38
<211> LENGTH: 21
<212> TYPE: DNA
<213> ORGANISM: Artificial Sequence
<220> FEATURE:
<223> OTHER INFORMATION: Synthetic Upper Primer 2

<400> SEQUENCE: 38
agcatcgagt cggccttgtt g                                               21

<210> SEQ ID NO 39
<211> LENGTH: 25
<212> TYPE: DNA
<213> ORGANISM: Artificial Sequence
```

```
<220> FEATURE:
<223> OTHER INFORMATION: Synthetic Lower Primer 2

<400> SEQUENCE: 39
gcggctgaag acggcctatg tgcct                                            25

<210> SEQ ID NO 40
<211> LENGTH: 20
<212> TYPE: DNA
<213> ORGANISM: Artificial Sequence
<220> FEATURE:
<223> OTHER INFORMATION: 5'RACE Upper Primer

<400> SEQUENCE: 40
tcggccttgt tggcctactg                                                  20

<210> SEQ ID NO 41
<211> LENGTH: 22
<212> TYPE: DNA
<213> ORGANISM: Artificial Sequence
<220> FEATURE:
<223> OTHER INFORMATION: Synthetic 5'RACE Lower Primer

<400> SEQUENCE: 41
tggtcatgct gatctccttg tc                                               22

<210> SEQ ID NO 42
<211> LENGTH: 359
<212> TYPE: DNA
<213> ORGANISM: Artificial Sequence
<220> FEATURE:
<223> OTHER INFORMATION: Synthetic Nucleotide sequence of amplified
      products by PCR using 5'RACE Upper Primer 1 and 5'RACE Lower
      Primer 1

<400> SEQUENCE: 42
tcggccttgt tggcctactg gcagttcaca gctgctgcag gcagagagac ggtggcctct      60
ctgtccccag actgagcttg tgagtgacac cgaggcagaa gagcccagaa ccatgaggag     120
cctcagggct ctgtttctgc tggtgactgc ctgcctggcg gtgagtgcca gccccgtgct     180
gacgccgccc gatgacatcc aagtgcaaga gaacttcgac atctctagga tctacgggaa     240
gtggttccac gtggccatgg gctccacctg cccgtggctg aagaagttca tggacaggat     300
gtccatgagc acgctggtgc tgggcgaggg gacgacggac aaggagatca gcatgacca      359

<210> SEQ ID NO 43
<211> LENGTH: 21
<212> TYPE: DNA
<213> ORGANISM: Artificial Sequence
<220> FEATURE:
<223> OTHER INFORMATION: Synthetic 3'RACE Upper Primer

<400> SEQUENCE: 43
tacaaccagc tctgggcatt c                                                21

<210> SEQ ID NO 44
<211> LENGTH: 21
<212> TYPE: DNA
<213> ORGANISM: Artificial Sequence
<220> FEATURE:
<223> OTHER INFORMATION: Synthetic 3'RACE Lower Primer

<400> SEQUENCE: 44
gcggctgaag acggcctatg t                                                21
```

```
<210> SEQ ID NO 45
<211> LENGTH: 325
<212> TYPE: DNA
<213> ORGANISM: Artificial Sequence
<220> FEATURE:
<223> OTHER INFORMATION: Synthetic Nucleotide sequence of amplified
      products by PCR using 3'RACE Upper Primer 1 and 3'RACE Lower
      Primer 1

<400> SEQUENCE: 45
tacaaccagc tctgggcatt cgatgccgtc caggggaaat gcgtcctctt caccetacggc      60 ggctgccaag gcaacggcag caagttctac tcagagaagg agtgcaggga gtactgcggt    120
gtccctggca acggtgacga ggagctgctg cccatcgcca gctgatcggc ccgcaggcca    180
cacggtggcg gggagggtgc gggccgtgtc tgttccggtg ccccacgtca ggccgggccg    240
ggtgacccgg gttcaaataa aaatgaaatt gtggactcct gaaaaaaaaa aaaaaaaaaa    300
ggccacatag gccgtcttca gccgc                                          325

<210> SEQ ID NO 46
<211> LENGTH: 1284
<212> TYPE: DNA
<213> ORGANISM: Artificial Sequence
<220> FEATURE:
<223> OTHER INFORMATION: Synthetic Full Length Fe alfa 1-m/bikunin
      Nucleotide Sequence

<400> SEQUENCE: 46
cagttcacag ctgctgcagg cagagagacg gtggcctctc tgtccccaga ctgagcttgt      60
gagtgacacc gaggcagaag agcccagaac catgaggagc ctcagggctc tgtttctgct    120
ggtgactgcc tgcctggcgg tgagtgccag ccccgtgctg acgccgcccg atgacatcca    180
agtgcaagag aacttcgaca tctctaggat ctacgggaag tggttccacg tggccatggg    240
ctccacctgc ccgtggctga gaagttcat ggacaggatg tccatgagca cgctggtgct    300
gggcgagggg gcgaaggaca aggagatcag catgaccagc actcgttggc ggagaggcac    360
ctgcgaggag atctccgggg cttatgagaa aacagacact gacggaaagt tcctctatca    420
taagcctaga tggaacatca ccatggagtc ctatgtggtc cacaccaact atgacgagta    480
cgccatcctt ctgaccaaga aattcagcca ccaccacggg cccaccatta ccgccaagct    540
ctatgggcga cagccacagc ttcgagaaag cctgctggag gagttcaggg aggtcgcctt    600
gggcgtgggc atccccgagg actccatctt cacgatggcc gacaaggtg agtgtgtccc    660 tggggagcag gaaccagagc cctctccact cacgagagcc cggcgggctg tgctgccccca    720 ggaagaggaa ggatcagggg ccaggctgct agcaactgat ttcagcaaga aggaagatgc    780
ctgccagctg ggccacgcag aaggcccttg cctggggatg gtcacgaggt atttctataa    840
tggctcatcc atggcctgtg agaccttcca atatggcggc tgcctgggca cggcaacaa    900 cttcgcctca gagaagggt gtctgcagac ctgccgaacc gtggcggcct gcaacctccc    960
catagtgacc ggcccctgcc gaggctacaa ccagctctgg gcattcgatg ccgtccaggg   1020
gaaatgcgtc ctcttcacct acggcggctg ccaaggcaac ggcagcaagt tctactcaga   1080
gaaggagtgc agggagtact gcggtgtccc tggcaacggt gacgaggagc tgctgcccat   1140
cgccagctga tcggcccgca ggccacacgg tggcggggag ggtgcgggcc gtgtctgttc   1200
cggtgcccca cgtcaggccg ggccgggtga cccgggttca aataaaaatg aaattgtgga   1260
ctcctgaaaa aaaaaaaaa aaaa                                           1284

<210> SEQ ID NO 47
```

```
<211> LENGTH: 56
<212> TYPE: DNA
<213> ORGANISM: Artificial Sequence
<220> FEATURE:
<223> OTHER INFORMATION: Synthetic Upper Primer

<400> SEQUENCE: 47
cacggatcca gccccgtgct gacgccgccc gatgacatcc aagtgcaaga gaactt         56

<210> SEQ ID NO 48
<211> LENGTH: 55
<212> TYPE: DNA
<213> ORGANISM: Artificial Sequence
<220> FEATURE:
<223> OTHER INFORMATION: Synthetic Lower Primer

<400> SEQUENCE: 48
cacctcgagt tagtggtggt ggtggtgatg cgtgagtgga gagggctctg gttcc          55

<210> SEQ ID NO 49
<211> LENGTH: 441
<212> TYPE: DNA
<213> ORGANISM: Homo sapiens
<220> FEATURE:
<221> NAME/KEY: CDS
<222> LOCATION: (1)..(441)

<400> SEQUENCE: 49 atg gcc ggg ccc ctg cgc gcc ccg ctg ctc ctg ctg gcc atc ctg gcc        48
Met Ala Gly Pro Leu Arg Ala Pro Leu Leu Leu Leu Ala Ile Leu Ala
1               5                   10                  15 gtg gcc ctg gcc gtg agc ccc gcg gcc ggc tcc agt ccc ggc aag ccg        96
Val Ala Leu Ala Val Ser Pro Ala Ala Gly Ser Ser Pro Gly Lys Pro
            20                  25                  30 ccg cgc ctg gtg gga ggc ccc atg gac gcc agc gtg gag gag gag ggt       144
Pro Arg Leu Val Gly Gly Pro Met Asp Ala Ser Val Glu Glu Glu Gly
        35                  40                  45 gtg cgg cgt gca ctg gac ttt gcc gtc ggc gag tac aac aaa gcc agc       192
Val Arg Arg Ala Leu Asp Phe Ala Val Gly Glu Tyr Asn Lys Ala Ser
    50                  55                  60 aac gac atg tac cac agc cgc gcg ctg cag gtg gtg cgc gcc cgc aag       240
Asn Asp Met Tyr His Ser Arg Ala Leu Gln Val Val Arg Ala Arg Lys
65                  70                  75                  80 cag atc gta gct ggg gtg aac tac ttc ttg gac gtg gag ctg ggc cga       288
Gln Ile Val Ala Gly Val Asn Tyr Phe Leu Asp Val Glu Leu Gly Arg
                85                  90                  95 acc acg tgt acc aag acc cag ccc aac ttg gac aac tgc ccc ttc cat       336
Thr Thr Cys Thr Lys Thr Gln Pro Asn Leu Asp Asn Cys Pro Phe His
            100                 105                 110 gac cag cca cat ctg aaa agg aaa gca ttc tgc tct ttc cag atc tac       384
Asp Gln Pro His Leu Lys Arg Lys Ala Phe Cys Ser Phe Gln Ile Tyr
        115                 120                 125 gct gtg cct tgg cag gga aca atg acc ttg tcg aaa tcc acc tgt cag       432
Ala Val Pro Trp Gln Gly Thr Met Thr Leu Ser Lys Ser Thr Cys Gln
    130                 135                 140 gac gcc tag                                                           441
Asp Ala
145

<210> SEQ ID NO 50
<211> LENGTH: 146
<212> TYPE: PRT
<213> ORGANISM: Homo sapiens

<400> SEQUENCE: 50
```

```
Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145

<210> SEQ ID NO 51
<211> LENGTH: 441
<212> TYPE: DNA
<213> ORGANISM: Macaca fuscata
<220> FEATURE:
<221> NAME/KEY: CDS
<222> LOCATION: (1)..(441)

<400> SEQUENCE: 51 atg gcc ggg ccc ctg cgc gcc ccg ctg ctc ctg ctg gcc atc ctg gcc      48
Met Ala Gly Pro Leu Arg Ala Pro Leu Leu Leu Ala Ile Leu Ala
1               5                   10                  15 gtg gct ctg gca gtg agc ccc gcg gcc gga gcg agt ccc ggg aag ccg      96
Val Ala Leu Ala Val Ser Pro Ala Ala Gly Ala Ser Pro Gly Lys Pro
            20                  25                  30 ccg cgc cta gtg ggc ggc ccc atg gac gcc agc gtg gag gag gag ggt     144
Pro Arg Leu Val Gly Gly Pro Met Asp Ala Ser Val Glu Glu Glu Gly
        35                  40                  45 gtg cgg cgt gcc ctg gac ttt gcc gtc agc gag tac aac aaa gcc agc     192
Val Arg Arg Ala Leu Asp Phe Ala Val Ser Glu Tyr Asn Lys Ala Ser
50                  55                  60 aac gac atg tac cac agc cgc gcg ctg cag gtg gtg cgc gcc cgc aag     240
Asn Asp Met Tyr His Ser Arg Ala Leu Gln Val Val Arg Ala Arg Lys
65                  70                  75                  80 cag atc gta gct ggg gtg aac tac ttc ttg gac gtg gag ttg ggc cga     288
Gln Ile Val Ala Gly Val Asn Tyr Phe Leu Asp Val Glu Leu Gly Arg
                85                  90                  95 acc aca tgt acc aag acc cag ccc aac ttg gac aac tgc ccc ttc cat     336
Thr Thr Cys Thr Lys Thr Gln Pro Asn Leu Asp Asn Cys Pro Phe His
            100                 105                 110 gaa cag cca cat ctg aag agg aaa gca ttc tgc tct ttc cag atc tac     384
Glu Gln Pro His Leu Lys Arg Lys Ala Phe Cys Ser Phe Gln Ile Tyr
        115                 120                 125 act gtg cct tgg cag ggc aca atg acc ttg tcg aaa tcc acc tgt cag     432
Thr Val Pro Trp Gln Gly Thr Met Thr Leu Ser Lys Ser Thr Cys Gln
    130                 135                 140 gac gcc tag                                                         441
Asp Ala
```

<210> SEQ ID NO 52
<211> LENGTH: 146
<212> TYPE: PRT
<213> ORGANISM: Macaca fuscata

<400> SEQUENCE: 52

```
Met Ala Gly Pro Leu Arg Ala Pro Leu Leu Leu Ala Ile Leu Ala
1               5                   10                  15

Val Ala Leu Ala Val Ser Pro Ala Ala Gly Ala Ser Pro Gly Lys Pro
            20                  25                  30

Pro Arg Leu Val Gly Gly Pro Met Asp Ala Ser Val Glu Glu Gly
        35                  40                  45

Val Arg Arg Ala Leu Asp Phe Ala Val Ser Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Glu Gln Pro His Leu Lys Arg Lys Ala Phe Cys Ser Phe Gln Ile Tyr
        115                 120                 125

Thr Val Pro Trp Gln Gly Thr Met Thr Leu Ser Lys Ser Thr Cys Gln
    130                 135                 140

Asp Ala
145
```

<210> SEQ ID NO 53
<211> LENGTH: 447
<212> TYPE: DNA
<213> ORGANISM: Bos taurus
<220> FEATURE:
<221> NAME/KEY: CDS
<222> LOCATION: (1)..(447)

<400> SEQUENCE: 53

```
atg gtg ggc tcc ccg cgc gcc cca ctg ctc ctg ctg gca tcc ctg atc      48
Met Val Gly Ser Pro Arg Ala Pro Leu Leu Leu Leu Ala Ser Leu Ile
1               5                   10                  15 gtc gcc ctg gcc ctg gcc ctg gcc gtg agc ccc gcg gca gcg cag ggc      96
Val Ala Leu Ala Leu Ala Leu Ala Val Ser Pro Ala Ala Ala Gln Gly
            20                  25                  30 cct agg aag ggt cgc ctg ctg ggc ggc ctg atg gag gcg gac gtc aat     144
Pro Arg Lys Gly Arg Leu Leu Gly Gly Leu Met Glu Ala Asp Val Asn
        35                  40                  45 gag gag ggc gtg cag gag gcg ctg tcc ttt gcg gtc agc gag ttc aac     192
Glu Glu Gly Val Gln Glu Ala Leu Ser Phe Ala Val Ser Glu Phe Asn
    50                  55                  60 aag cgg agc aac gac gct tac cag agc cgc gtg gtg cgc gtg gtg cgc     240
Lys Arg Ser Asn Asp Ala Tyr Gln Ser Arg Val Val Arg Val Val Arg
65                  70                  75                  80 gcc cgc aag cag gtc gtg tca ggg atg aac tat ttc ttg gac gtg gag     288
Ala Arg Lys Gln Val Val Ser Gly Met Asn Tyr Phe Leu Asp Val Glu
                85                  90                  95 ctt ggc cgg act aca tgt acc aag tcc cag gcc aac tta gac agc tgt     336
Leu Gly Arg Thr Thr Cys Thr Lys Ser Gln Ala Asn Leu Asp Ser Cys
            100                 105                 110 ccc ttc cat aac cag ccg cac ctg aag agg gaa aag ctg tgc tcc ttc     384
```

```
Pro Phe His Asn Gln Pro His Leu Lys Arg Glu Lys Leu Cys Ser Phe
        115                 120                 125 cag gtt tac gtc gtc cca tgg atg aac acc atc aac ctg gtg aag ttt      432
Gln Val Tyr Val Val Pro Trp Met Asn Thr Ile Asn Leu Val Lys Phe
        130                 135                 140 agc tgc cag gat taa                                                   447
Ser Cys Gln Asp
145

<210> SEQ ID NO 54
<211> LENGTH: 148
<212> TYPE: PRT
<213> ORGANISM: Bos taurus

<400> SEQUENCE: 54

Met Val Gly Ser Pro Arg Ala Pro Leu Leu Leu Ala Ser Leu Ile
1               5                   10                  15

Val Ala Leu Ala Leu Ala Leu Ala Val Ser Pro Ala Ala Gln Gly
            20                  25                  30

Pro Arg Lys Gly Arg Leu Leu Gly Gly Leu Met Glu Ala Asp Val Asn
        35                  40                  45

Glu Glu Gly Val Gln Glu Ala Leu Ser Phe Ala Val Ser Glu Phe Asn
    50                  55                  60

Lys Arg Ser Asn Asp Ala Tyr Gln Ser Arg Val Val Arg Val Val
65                  70                  75                  80

Ala Arg Lys Gln Val Val Ser Gly Met Asn Tyr Phe Leu Asp Val Glu
                85                  90                  95

Leu Gly Arg Thr Thr Cys Thr Lys Ser Gln Ala Asn Leu Asp Ser Cys
            100                 105                 110

Pro Phe His Asn Gln Pro His Leu Lys Arg Glu Lys Leu Cys Ser Phe
        115                 120                 125

Gln Val Tyr Val Val Pro Trp Met Asn Thr Ile Asn Leu Val Lys Phe
        130                 135                 140

Ser Cys Gln Asp
145

<210> SEQ ID NO 55
<211> LENGTH: 441
<212> TYPE: DNA
<213> ORGANISM: Sus scrofa domesticus
<220> FEATURE:
<221> NAME/KEY: CDS
<222> LOCATION: (1)..(441)

<400> SEQUENCE: 55 atg gcc ggc tcc ccg cgc tcc ccg ctg ctc ctg ctg gcc gcc ctg gcc      48
Met Ala Gly Ser Pro Arg Ser Pro Leu Leu Leu Leu Ala Ala Leu Ala
1               5                   10                  15 ctg gcc ctc gcc ctg gcc gtg agc ccc gcg gcc gga cag ggc cac aag      96
Leu Ala Leu Ala Leu Ala Val Ser Pro Ala Ala Gly Gln Gly His Lys
            20                  25                  30 ggc cgc ctg gtg ggc ggc cta ata gac gcg gat gtc aac gag gag ggc      144
Gly Arg Leu Val Gly Gly Leu Ile Asp Ala Asp Val Asn Glu Glu Gly
        35                  40                  45 gtg cag cag gcg ctg tcc ttt gcc ctc agc gag tac aac aaa gcg agc      192
Val Gln Gln Ala Leu Ser Phe Ala Leu Ser Glu Tyr Asn Lys Ala Ser
    50                  55                  60 aat gac gcc tac cac ggc cgc gtg ctg cgc gtg ctg cgc gtc cgc aag      240
Asn Asp Ala Tyr His Gly Arg Val Leu Arg Val Leu Arg Val Arg Lys
65                  70                  75                  80
```

```
cag gtc gtg gcg ggg atg aac tac ttc ttg gaa gtg gag att ggc cga      288
Gln Val Val Ala Gly Met Asn Tyr Phe Leu Glu Val Glu Ile Gly Arg
                 85                  90                  95 acc acg tgc acc aag tcc cag gcc aac ctg gac aac tgt ccc ttc ccc      336
Thr Thr Cys Thr Lys Ser Gln Ala Asn Leu Asp Asn Cys Pro Phe Pro
            100                 105                 110 aac cag ccg gac ctg cag aag aaa acg ctg tgc tcc ttc caa gtt tac      384
Asn Gln Pro Asp Leu Gln Lys Lys Thr Leu Cys Ser Phe Gln Val Tyr
        115                 120                 125 acc gtc ccc tgg aag ggc acc acc tcc ctg gtg aag tcc agc tgt cgc      432
Thr Val Pro Trp Lys Gly Thr Thr Ser Leu Val Lys Ser Ser Cys Arg
    130                 135                 140 gat gaa tag                                                          441
Asp Glu
145

<210> SEQ ID NO 56
<211> LENGTH: 146
<212> TYPE: PRT
<213> ORGANISM: Sus scrofa domesticus

<400> SEQUENCE: 56

Met Ala Gly Ser Pro Arg Ser Pro Leu Leu Leu Ala Ala Leu Ala
1               5                   10                  15

Leu Ala Leu Ala Val Ser Pro Ala Ala Gly Gln Gly His Lys
            20                  25                  30

Gly Arg Leu Val Gly Gly Leu Ile Asp Ala Asp Val Asn Glu Glu Gly
        35                  40                  45

Val Gln Gln Ala Leu Ser Phe Ala Leu Ser Glu Tyr Asn Lys Ala Ser
    50                  55                  60

Asn Asp Ala Tyr His Gly Arg Val Leu Arg Val Leu Arg Val Arg Lys
65                  70                  75                  80

Gln Val Val Ala Gly Met Asn Tyr Phe Leu Glu Val Glu Ile Gly Arg
                85                  90                  95

Thr Thr Cys Thr Lys Ser Gln Ala Asn Leu Asp Asn Cys Pro Phe Pro
            100                 105                 110

Asn Gln Pro Asp Leu Gln Lys Lys Thr Leu Cys Ser Phe Gln Val Tyr
        115                 120                 125

Thr Val Pro Trp Lys Gly Thr Thr Ser Leu Val Lys Ser Ser Cys Arg
    130                 135                 140

Asp Glu
145

<210> SEQ ID NO 57
<211> LENGTH: 423
<212> TYPE: DNA
<213> ORGANISM: Rattus norvegicus
<220> FEATURE:
<221> NAME/KEY: CDS
<222> LOCATION: (1)..(423)

<400> SEQUENCE: 57 atg gcc agc ccg ctg cgc tcc ttg atg cta ctg ctg gcc gtc ctg gcc      48
Met Ala Ser Pro Leu Arg Ser Leu Met Leu Leu Leu Ala Val Leu Ala
1               5                   10                  15 gtg gcc tgg gcc gga acc tcc agg cca ccc cga ttg ttg gga gct        96
Val Ala Trp Ala Gly Thr Ser Arg Pro Pro Arg Leu Leu Gly Ala
            20                  25                  30 ccg cag gag gca gat gcc agc gag gag ggc gtg cag cga gcg ttg gac    144
Pro Gln Glu Ala Asp Ala Ser Glu Glu Gly Val Gln Arg Ala Leu Asp
        35                  40                  45
```

```
ttc gcc gta agc gag tac aac aag ggc agc aac gat gcg tac cac agc      192
Phe Ala Val Ser Glu Tyr Asn Lys Gly Ser Asn Asp Ala Tyr His Ser
         50                  55                  60 cgc gcc ata cag gtg gtg aga gct cgt aag cag ctt gtg gct gga ata      240
Arg Ala Ile Gln Val Val Arg Ala Arg Lys Gln Leu Val Ala Gly Ile
 65                  70                  75                  80 aac tat tat ttg gat gtg gag atg ggc cga act aca tgt acc aag tcc      288
Asn Tyr Tyr Leu Asp Val Glu Met Gly Arg Thr Thr Cys Thr Lys Ser
                 85                  90                  95 cag aca aat ttg act aac tgt cct ttc cac gac cag ccc cat ctg atg      336
Gln Thr Asn Leu Thr Asn Cys Pro Phe His Asp Gln Pro His Leu Met
            100                 105                 110 agg aag gca ctc tgc tcc ttc cag atc tac agc gtg ccc tgg aaa ggc      384
Arg Lys Ala Leu Cys Ser Phe Gln Ile Tyr Ser Val Pro Trp Lys Gly
        115                 120                 125 aca cac acc ctg aca aaa tcc agc tgc aaa aat gcc taa                  423
Thr His Thr Leu Thr Lys Ser Ser Cys Lys Asn Ala
    130                 135                 140
```

<210> SEQ ID NO 58
<211> LENGTH: 140
<212> TYPE: PRT
<213> ORGANISM: Rattus norvegicus

<400> SEQUENCE: 58

```
Met Ala Ser Pro Leu Arg Ser Leu Met Leu Leu Ala Val Leu Ala
 1               5                  10                  15

Val Ala Trp Ala Gly Thr Ser Arg Pro Pro Arg Leu Leu Gly Ala
             20                  25                  30

Pro Gln Glu Ala Asp Ala Ser Glu Glu Gly Val Gln Arg Ala Leu Asp
         35                  40                  45

Phe Ala Val Ser Glu Tyr Asn Lys Gly Ser Asn Asp Ala Tyr His Ser
     50                  55                  60

Arg Ala Ile Gln Val Val Arg Ala Arg Lys Gln Leu Val Ala Gly Ile
 65                  70                  75                  80

Asn Tyr Tyr Leu Asp Val Glu Met Gly Arg Thr Thr Cys Thr Lys Ser
                 85                  90                  95

Gln Thr Asn Leu Thr Asn Cys Pro Phe His Asp Gln Pro His Leu Met
            100                 105                 110

Arg Lys Ala Leu Cys Ser Phe Gln Ile Tyr Ser Val Pro Trp Lys Gly
        115                 120                 125

Thr His Thr Leu Thr Lys Ser Ser Cys Lys Asn Ala
    130                 135                 140
```

<210> SEQ ID NO 59
<211> LENGTH: 30
<212> TYPE: DNA
<213> ORGANISM: Artificial Sequence
<220> FEATURE:
<223> OTHER INFORMATION: Synthetic 5' end of First Strand cDNA

<400> SEQUENCE: 59
tcgtagctca gccggaacaa ccggatgacc                                      30

<210> SEQ ID NO 60
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 60

```
atg tct cgc tcc gtg gcc tta gct gtg ctc gcg cta ctc tct ctt tct      48
Met Ser Arg Ser Val Ala Leu Ala Val Leu Ala Leu Leu Ser Leu Ser
1               5                   10                  15 ggc ctg gag gct atc cag cgt act cca aag att cag gtt tac tca cgt      96
Gly Leu Glu Ala Ile Gln Arg Thr Pro Lys Ile Gln Val Tyr Ser Arg
            20                  25                  30 cat cca gca gag aat gga aag tca aat ttc ctg aat tgc tat gtg tct     144
His Pro Ala Glu Asn Gly Lys Ser Asn Phe Leu Asn Cys Tyr Val Ser
        35                  40                  45 ggg ttt cat cca tcc gac att gaa gtt gac tta ctg aag aat gga gag     192
Gly Phe His Pro Ser Asp Ile Glu Val Asp Leu Leu Lys Asn Gly Glu
    50                  55                  60 aga att gaa aaa gtg gag cat tca gac ttg tct ttc agc aag gac tgg     240
Arg Ile Glu Lys Val Glu His Ser Asp Leu Ser Phe Ser Lys Asp Trp
65                  70                  75                  80 tct ttc tat ctc ttg tac tac act gaa ttc acc ccc act gaa aaa gat     288
Ser Phe Tyr Leu Leu Tyr Tyr Thr Glu Phe Thr Pro Thr Glu Lys Asp
                85                  90                  95 gag tat gcc tgc cgt gtg aac cat gtg act ttg tca cag ccc aag ata     336
Glu Tyr Ala Cys Arg Val Asn His Val Thr Leu Ser Gln Pro Lys Ile
            100                 105                 110 gtt aag tgg gat cga gac atg taa                                     360
Val Lys Trp Asp Arg Asp Met
            115
```

<210> SEQ ID NO 61
<211> LENGTH: 119
<212> TYPE: PRT
<213> ORGANISM: Homo sapiens

<400> SEQUENCE: 61

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115
```

<210> SEQ ID NO 62
<211> LENGTH: 357
<212> TYPE: DNA
<213> ORGANISM: Equus caballus
<220> FEATURE:
<221> NAME/KEY: CDS
<222> LOCATION: (1)..(357)

<400> SEQUENCE: 62

```
atg gct cgc gtc gtg gcg ctc gtc ctg ctc ggg cta ctc tcc ctg act      48
Met Ala Arg Val Val Ala Leu Val Leu Leu Gly Leu Leu Ser Leu Thr
```

```
                1               5               10              15
ggc ctg gag gcc gtc ccg cgt gtt ccg aag gtt cag gtt tac tca cgt       96
Gly Leu Glu Ala Val Pro Arg Val Pro Lys Val Gln Val Tyr Ser Arg
                20              25              30 cac cca gca gag aat gga aag cca aat ttc ctg aac tgc tat gtc tct      144
His Pro Ala Glu Asn Gly Lys Pro Asn Phe Leu Asn Cys Tyr Val Ser
                35              40              45 ggg ttc cat ccg cct gag att gaa att gat ttg cta aag aat gga gag      192
Gly Phe His Pro Pro Glu Ile Glu Ile Asp Leu Leu Lys Asn Gly Glu
        50              55              60 aag atg aaa gtc gac cgg tca gac ctg tct ttc agc aag gac tgg tct      240
Lys Met Lys Val Asp Arg Ser Asp Leu Ser Phe Ser Lys Asp Trp Ser
65              70              75              80 ttc tat ctt ctg gtc cat act gac ttt act ccc aat ggt gtg gat gag      288
Phe Tyr Leu Leu Val His Thr Asp Phe Thr Pro Asn Gly Val Asp Glu
                85              90              95 tat agt tgc cgt gta cag cac tct act ctc aaa gac ccc ctg ata gtt      336
Tyr Ser Cys Arg Val Gln His Ser Thr Leu Lys Asp Pro Leu Ile Val
                100             105             110 aag tgg gat cga gac ctc taa                                          357
Lys Trp Asp Arg Asp Leu
        115

<210> SEQ ID NO 63
<211> LENGTH: 118
<212> TYPE: PRT
<213> ORGANISM: Equus caballus

<400> SEQUENCE: 63

Met Ala Arg Val Val Ala Leu Val Leu Leu Gly Leu Leu Ser Leu Thr
1               5                   10                  15

Gly Leu Glu Ala Val Pro Arg Val Pro Lys Val Gln Val Tyr Ser Arg
                20                  25                  30

His Pro Ala Glu Asn Gly Lys Pro Asn Phe Leu Asn Cys Tyr Val Ser
            35                  40                  45

Gly Phe His Pro Pro Glu Ile Glu Ile Asp Leu Leu Lys Asn Gly Glu
        50                  55                  60

Lys Met Lys Val Asp Arg Ser Asp Leu Ser Phe Ser Lys Asp Trp Ser
65                  70                  75                  80

Phe Tyr Leu Leu Val His Thr Asp Phe Thr Pro Asn Gly Val Asp Glu
                85                  90                  95

Tyr Ser Cys Arg Val Gln His Ser Thr Leu Lys Asp Pro Leu Ile Val
            100                 105                 110

Lys Trp Asp Arg Asp Leu
        115

<210> SEQ ID NO 64
<211> LENGTH: 357
<212> TYPE: DNA
<213> ORGANISM: Bos taurus
<220> FEATURE:
<221> NAME/KEY: CDS
<222> LOCATION: (1)..(351)

<400> SEQUENCE: 64 atg gct cgc ttc gtg gcc ttg gtc ctt ctc ggg ctg ctg tcg ctg tct       48
Met Ala Arg Phe Val Ala Leu Val Leu Leu Gly Leu Leu Ser Leu Ser
1               5               10              15 gga ctg gac gcc atc cag cgt cct cca aag att caa gtg tac tca aga       96
Gly Leu Asp Ala Ile Gln Arg Pro Pro Lys Ile Gln Val Tyr Ser Arg
                20              25              30
```

```
cac cca cca gaa gat gga aag cca aat tac ctg aac tgc tat gtg tat    144
His Pro Pro Glu Asp Gly Lys Pro Asn Tyr Leu Asn Cys Tyr Val Tyr
        35                  40                  45 ggg ttc cat cca ccc cag att gaa atc gat ttg ctg aag aat ggg gag    192
Gly Phe His Pro Pro Gln Ile Glu Ile Asp Leu Leu Lys Asn Gly Glu
 50                  55                  60 aag att aaa tcg gag cag tca gac ctg tct ttc agc aag gac tgg tct    240
Lys Ile Lys Ser Glu Gln Ser Asp Leu Ser Phe Ser Lys Asp Trp Ser
 65                  70                  75                   80 ttc tac ctg ctg tcc cac gct gag ttc act ccc aac agc aag gat cag    288
Phe Tyr Leu Leu Ser His Ala Glu Phe Thr Pro Asn Ser Lys Asp Gln
                 85                  90                  95 tac agc tgc cga gtg aaa cac gtt act ttg gaa caa ccc cgg ata gtt    336
Tyr Ser Cys Arg Val Lys His Val Thr Leu Glu Gln Pro Arg Ile Val
            100                 105                 110 aag tgg gat cga gac ctgtaa                                         357
Lys Trp Asp Arg Asp
        115

<210> SEQ ID NO 65
<211> LENGTH: 117
<212> TYPE: PRT
<213> ORGANISM: Bos taurus

<400> SEQUENCE: 65

Met Ala Arg Phe Val Ala Leu Val Leu Leu Gly Leu Ser Leu Ser
 1               5                  10                  15

Gly Leu Asp Ala Ile Gln Arg Pro Pro Lys Ile Gln Val Tyr Ser Arg
                 20                  25                  30

His Pro Pro Glu Asp Gly Lys Pro Asn Tyr Leu Asn Cys Tyr Val Tyr
            35                  40                  45

Gly Phe His Pro Pro Gln Ile Glu Ile Asp Leu Leu Lys Asn Gly Glu
 50                  55                  60

Lys Ile Lys Ser Glu Gln Ser Asp Leu Ser Phe Ser Lys Asp Trp Ser
 65                  70                  75                   80

Phe Tyr Leu Leu Ser His Ala Glu Phe Thr Pro Asn Ser Lys Asp Gln
                 85                  90                  95

Tyr Ser Cys Arg Val Lys His Val Thr Leu Glu Gln Pro Arg Ile Val
            100                 105                 110

Lys Trp Asp Arg Asp
        115

<210> SEQ ID NO 66
<211> LENGTH: 357
<212> TYPE: DNA
<213> ORGANISM: Sus scrofa domesticus
<220> FEATURE:
<221> NAME/KEY: CDS
<222> LOCATION: (1)..(357)

<400> SEQUENCE: 66 atg gct ccc ctc gtg gcc ttg gtc ctg ctc ggg ctg ctc tca ctg tct    48
Met Ala Pro Leu Val Ala Leu Val Leu Leu Gly Leu Leu Ser Leu Ser
 1               5                  10                  15 ggc ctg gat gcg gtc gcg cgt ccc ccg aag gtt cag gtt tac tca cgc    96
Gly Leu Asp Ala Val Ala Arg Pro Pro Lys Val Gln Val Tyr Ser Arg
                 20                  25                  30 cac cca gcg gaa aac gga aag cca aat tac ctg aac tgc tat gta tct   144
His Pro Ala Glu Asn Gly Lys Pro Asn Tyr Leu Asn Cys Tyr Val Ser
            35                  40                  45
```

```
ggg ttc cat ccg ccc cag att gaa att gat ttg ctg aaa aac ggg gag    192
Gly Phe His Pro Pro Gln Ile Glu Ile Asp Leu Leu Lys Asn Gly Glu
             50                  55                  60 aag atg aac gcg gag cag tca gac ctg tct ttc agc aag gac tgg tct    240
Lys Met Asn Ala Glu Gln Ser Asp Leu Ser Phe Ser Lys Asp Trp Ser
 65                  70                  75                  80 ttc tac ctt ctg gtc cac act gag ttc act cct aac gct gtg gat cag    288
Phe Tyr Leu Leu Val His Thr Glu Phe Thr Pro Asn Ala Val Asp Gln
                 85                  90                  95 tat agc tgc cgc gtg aag cac gtg act ctc gat aag ccc aag ata gtt    336
Tyr Ser Cys Arg Val Lys His Val Thr Leu Asp Lys Pro Lys Ile Val
            100                 105                 110 aag tgg gat cga gac cac taa                                        357
Lys Trp Asp Arg Asp His
            115

<210> SEQ ID NO 67
<211> LENGTH: 118
<212> TYPE: PRT
<213> ORGANISM: Sus scrofa domesticus

<400> SEQUENCE: 67

Met Ala Pro Leu Val Ala Leu Val Leu Leu Gly Leu Leu Ser Leu Ser
 1               5                  10                  15

Gly Leu Asp Ala Val Ala Arg Pro Pro Lys Val Gln Val Tyr Ser Arg
             20                  25                  30

His Pro Ala Glu Asn Gly Lys Pro Asn Tyr Leu Asn Cys Tyr Val Ser
         35                  40                  45

Gly Phe His Pro Pro Gln Ile Glu Ile Asp Leu Leu Lys Asn Gly Glu
     50                  55                  60

Lys Met Asn Ala Glu Gln Ser Asp Leu Ser Phe Ser Lys Asp Trp Ser
 65                  70                  75                  80

Phe Tyr Leu Leu Val His Thr Glu Phe Thr Pro Asn Ala Val Asp Gln
                 85                  90                  95

Tyr Ser Cys Arg Val Lys His Val Thr Leu Asp Lys Pro Lys Ile Val
            100                 105                 110

Lys Trp Asp Arg Asp His
            115

<210> SEQ ID NO 68
<211> LENGTH: 360
<212> TYPE: DNA
<213> ORGANISM: Mus musculus
<220> FEATURE:
<221> NAME/KEY: CDS
<222> LOCATION: (1)..(360)

<400> SEQUENCE: 68 atg gct cgc tcg gtg acc ctg gtc ttt ctg gtg ctt gtc tca ctg acc     48
Met Ala Arg Ser Val Thr Leu Val Phe Leu Val Leu Val Ser Leu Thr
 1               5                  10                  15 ggc ctg tat gct atc cag aaa acc cct caa att caa gta tac tca cgc     96
Gly Leu Tyr Ala Ile Gln Lys Thr Pro Gln Ile Gln Val Tyr Ser Arg
             20                  25                  30 cac cca ccg gag aat ggg aag ccg aac ata ctg aac tgc tac gta aca    144
His Pro Pro Glu Asn Gly Lys Pro Asn Ile Leu Asn Cys Tyr Val Thr
         35                  40                  45 cag ttc cac ccg cct cac att gaa atc caa atg ctg aag aac ggg aaa    192
Gln Phe His Pro Pro His Ile Glu Ile Gln Met Leu Lys Asn Gly Lys
     50                  55                  60 aaa att cct aaa gta gag atg tca gat atg tcc ttc agc aag gac tgg    240
Lys Ile Pro Lys Val Glu Met Ser Asp Met Ser Phe Ser Lys Asp Trp
```

```
                                                                                          -continued Lys Ile Pro Lys Val Glu Met Ser Asp Met Ser Phe Ser Lys Asp Trp
 65                  70                  75                  80 tct ttc tat atc ctg gct cac act gaa ttc acc ccc act gag act gat    288
Ser Phe Tyr Ile Leu Ala His Thr Glu Phe Thr Pro Thr Glu Thr Asp
                 85                  90                  95 aca tac gcc tgc aga gtt aag cat gcc agt atg gcc gag ccc aag acc    336
Thr Tyr Ala Cys Arg Val Lys His Ala Ser Met Ala Glu Pro Lys Thr
            100                 105                 110 gtc tac tgg gat cga gac atg tga                                    360
Val Tyr Trp Asp Arg Asp Met
        115

<210> SEQ ID NO 69
<211> LENGTH: 119
<212> TYPE: PRT
<213> ORGANISM: Mus musculus

<400> SEQUENCE: 69

Met Ala Arg Ser Val Thr Leu Val Phe Leu Val Leu Val Ser Leu Thr
  1               5                  10                  15

Gly Leu Tyr Ala Ile Gln Lys Thr Pro Gln Ile Gln Val Tyr Ser Arg
             20                  25                  30

His Pro Pro Glu Asn Gly Lys Pro Asn Ile Leu Asn Cys Tyr Val Thr
         35                  40                  45

Gln Phe His Pro Pro His Ile Glu Ile Gln Met Leu Lys Asn Gly Lys
     50                  55                  60

Lys Ile Pro Lys Val Glu Met Ser Asp Met Ser Phe Ser Lys Asp Trp
 65                  70                  75                  80

Ser Phe Tyr Ile Leu Ala His Thr Glu Phe Thr Pro Thr Glu Thr Asp
                 85                  90                  95

Thr Tyr Ala Cys Arg Val Lys His Ala Ser Met Ala Glu Pro Lys Thr
            100                 105                 110

Val Tyr Trp Asp Arg Asp Met
        115

<210> SEQ ID NO 70
<211> LENGTH: 360
<212> TYPE: DNA
<213> ORGANISM: Macaca fuscata
<220> FEATURE:
<221> NAME/KEY: CDS
<222> LOCATION: (1)..(360)

<400> SEQUENCE: 70 atg ttt cgc tca gtg gcc tta gca gtg ctg gcg cta ctc ttt ctt tct     48
Met Phe Arg Ser Val Ala Leu Ala Val Leu Ala Leu Leu Phe Leu Ser
  1               5                  10                  15 ggc ctg gag gct atc cag cgt gct cca aag att cag gtt tac tca cgc     96
Gly Leu Glu Ala Ile Gln Arg Ala Pro Lys Ile Gln Val Tyr Ser Arg
             20                  25                  30 cat cca cca gag aat gga aag tca aat ttc ctg aat tgc tat gtg tct    144
His Pro Pro Glu Asn Gly Lys Ser Asn Phe Leu Asn Cys Tyr Val Ser
         35                  40                  45 ggg ttt cat cca tct gat att gaa gtt gac tta ctg aag aat gga gag    192
Gly Phe His Pro Ser Asp Ile Glu Val Asp Leu Leu Lys Asn Gly Glu
     50                  55                  60 aaa atg ggg aaa gtg gag cat tca gac ttg tct ttc agc aaa gac tgg    240
Lys Met Gly Lys Val Glu His Ser Asp Leu Ser Phe Ser Lys Asp Trp
 65                  70                  75                  80 tct ttc tat ctc ttg tac tac act gaa ttc acc ccc aat gaa aaa gat    288
Ser Phe Tyr Leu Leu Tyr Tyr Thr Glu Phe Thr Pro Asn Glu Lys Asp
```

```
              85                  90                  95
gag tat gcc tgc cgt gtg aac cac gtg act ttg tca ggg ccc agg aca        336
Glu Tyr Ala Cys Arg Val Asn His Val Thr Leu Ser Gly Pro Arg Thr
            100                 105                 110 gtt aag tgg gat cga gac atg taa                                        360
Val Lys Trp Asp Arg Asp Met
        115

<210> SEQ ID NO 71
<211> LENGTH: 119
<212> TYPE: PRT
<213> ORGANISM: Macaca fuscata

<400> SEQUENCE: 71

Met Phe Arg Ser Val Ala Leu Ala Val Leu Ala Leu Leu Phe Leu Ser
1               5                   10                  15

Gly Leu Glu Ala Ile Gln Arg Ala Pro Lys Ile Gln Val Tyr Ser Arg
            20                  25                  30

His Pro Pro Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Lys Met Gly Lys Val Glu His Ser Asp Leu Ser Phe Ser Lys Asp Trp
65                  70                  75                  80

Ser Phe Tyr Leu Leu Tyr Tyr Thr Glu Phe Thr Pro Asn Glu Lys Asp
                85                  90                  95

Glu Tyr Ala Cys Arg Val Asn His Val Thr Leu Ser Gly Pro Arg Thr
            100                 105                 110

Val Lys Trp Asp Arg Asp Met
        115

<210> SEQ ID NO 72
<211> LENGTH: 360
<212> TYPE: DNA
<213> ORGANISM: Rattus norvegicus
<220> FEATURE:
<221> NAME/KEY: CDS
<222> LOCATION: (1)..(360)

<400> SEQUENCE: 72 atg gct cgc tcg gtg acc gtg atc ttt ctg gtg ctt gtc tct ctg gcc        48
Met Ala Arg Ser Val Thr Val Ile Phe Leu Val Leu Val Ser Leu Ala
1               5                   10                  15 gtc gtg ctt gcc att cag aaa act ccc caa att caa gtg tac tct cgc        96
Val Val Leu Ala Ile Gln Lys Thr Pro Gln Ile Gln Val Tyr Ser Arg
            20                  25                  30 cat cca ccg gag aat ggg aag ccc aac ttc ctc aac tgc tac gtg tct       144
His Pro Pro Glu Asn Gly Lys Pro Asn Phe Leu Asn Cys Tyr Val Ser
        35                  40                  45 cag ttc cac cca cct cag ata gaa att gag cta ctg aag aat gga aag       192
Gln Phe His Pro Pro Gln Ile Glu Ile Glu Leu Leu Lys Asn Gly Lys
    50                  55                  60 aag ata cca aat atc gag atg tca gat ctg tcc ttc agc aag gac tgg       240
Lys Ile Pro Asn Ile Glu Met Ser Asp Leu Ser Phe Ser Lys Asp Trp
65                  70                  75                  80 tct ttc tac atc ctg gct cac act gaa ttc aca ccc acc gag acc gat       288
Ser Phe Tyr Ile Leu Ala His Thr Glu Phe Thr Pro Thr Glu Thr Asp
                85                  90                  95 gta tat gct tgc aga gtt aaa cac gtc act ctg aag gag ccc aaa acc       336
Val Tyr Ala Cys Arg Val Lys His Val Thr Leu Lys Glu Pro Lys Thr
            100                 105                 110
```

```
gtc acc tgg gac cga gac atg taa                                           360
Val Thr Trp Asp Arg Asp Met
        115

<210> SEQ ID NO 73
<211> LENGTH: 119
<212> TYPE: PRT
<213> ORGANISM: Rattus norvegicus

<400> SEQUENCE: 73

Met Ala Arg Ser Val Thr Val Ile Phe Leu Val Leu Val Ser Leu Ala
1               5                   10                  15

Val Val Leu Ala Ile Gln Lys Thr Pro Gln Ile Gln Val Tyr Ser Arg
            20                  25                  30

His Pro Pro Glu Asn Gly Lys Pro Asn Phe Leu Asn Cys Tyr Val Ser
        35                  40                  45

Gln Phe His Pro Pro Gln Ile Glu Ile Glu Leu Leu Lys Asn Gly Lys
    50                  55                  60

Lys Ile Pro Asn Ile Glu Met Ser Asp Leu Ser Phe Ser Lys Asp Trp
65                  70                  75                  80

Ser Phe Tyr Ile Leu Ala His Thr Glu Phe Thr Pro Thr Glu Thr Asp
                85                  90                  95

Val Tyr Ala Cys Arg Val Lys His Val Thr Leu Lys Glu Pro Lys Thr
            100                 105                 110

Val Thr Trp Asp Arg Asp Met
        115

<210> SEQ ID NO 74
<211> LENGTH: 23
<212> TYPE: DNA
<213> ORGANISM: Artificial Sequence
<220> FEATURE:
<223> OTHER INFORMATION: Synthetic 3'end of First strand cDNA

<400> SEQUENCE: 74
ttcgtcacca tagttgcgtc tcc                                                  23

<210> SEQ ID NO 75
<211> LENGTH: 22
<212> TYPE: DNA
<213> ORGANISM: Artificial Sequence
<220> FEATURE:
<223> OTHER INFORMATION: Synthetic 5' end of First strand cDNA

<400> SEQUENCE: 75
gtctaccagg cattcgcttc at                                                   22

<210> SEQ ID NO 76
<211> LENGTH: 297
<212> TYPE: DNA
<213> ORGANISM: Artificial Sequence
<220> FEATURE:
<223> OTHER INFORMATION: Synthetic mcDNA

<400> SEQUENCE: 76
gtccagcatt ctccaaaggt tcaggtttac tcccgtcacc cagcagagaa tggaaagcca         60
aattttctga actgctacgt ttcggggttc caccccaccac aaattgatat cacccttgatg      120 aagaatggaa agaagatgga agaggaacag acagatctgt ccttcaacag ggactggact        180
ttctatcttc tggtccacac cgaatttact cccactgtcg aagatgagta tagctgccaa        240
gtgaatcata ctactctcag tgagcccaag gtcgttaagt gggatcgaga catgtaa           297
```

<210> SEQ ID NO 77
<211> LENGTH: 317
<212> TYPE: DNA
<213> ORGANISM: Artificial Sequence
<220> FEATURE:
<223> OTHER INFORMATION: Synthetic pcDNA

<400> SEQUENCE: 77

```
cctgggatcc gtccagcatt ctccaaaggt tcaggtttac tcccgtcacc cagcagagaa      60
tggaaagcca aatttctga actgctacgt ttcggggttc cacccaccac aaattgatat     120
caccttgatg aagaatggaa agaagatgga agcggaacag acagatctgt ccttcaacag     180
ggactggact ttctatcttc tggtccacac cgaatttact cccactgtcg aagatgagta     240
tagctgccaa gtgaatcata ctactctcag tgagcccaag gtcgttaagt gggatcgaga     300
catgtaagtc gactcga                                                    317
```

<210> SEQ ID NO 78
<211> LENGTH: 603
<212> TYPE: DNA
<213> ORGANISM: Homo sapiens
<220> FEATURE:
<221> NAME/KEY: CDS
<222> LOCATION: (1)..(603)

<400> SEQUENCE: 78

```
atg agg agc ctc ggg gcc ctg ctc ttg ctg ctg agc gcc tgc ctg gcg       48
Met Arg Ser Leu Gly Ala Leu Leu Leu Leu Leu Ser Ala Cys Leu Ala
1               5                   10                  15 gtg agc gct ggc cct gtg cca acg ccg ccc gac aac atc caa gtg cag       96
Val Ser Ala Gly Pro Val Pro Thr Pro Pro Asp Asn Ile Gln Val Gln
            20                  25                  30 gaa aac ttc aat atc tct cgg atc tat ggg aag tgg tac aac ctg gcc      144
Glu Asn Phe Asn Ile Ser Arg Ile Tyr Gly Lys Trp Tyr Asn Leu Ala
        35                  40                  45 atc ggt tcc acc tgc ccc tgg ctg aag aag atc atg gac agg atg aca      192
Ile Gly Ser Thr Cys Pro Trp Leu Lys Lys Ile Met Asp Arg Met Thr
    50                  55                  60 gtg agc acg ctg gtg ctg gga gag ggc gct aca gag gcg gag atc agc      240
Val Ser Thr Leu Val Leu Gly Glu Gly Ala Thr Glu Ala Glu Ile Ser
65                  70                  75                  80 atg acc agc act cgt tgg cgg aaa ggt gtc tgt gag gag acg tct gga      288
Met Thr Ser Thr Arg Trp Arg Lys Gly Val Cys Glu Glu Thr Ser Gly
                85                  90                  95 gct tat gag aaa aca gat act gat ggg aag ttt ctc tat cac aaa tcc      336
Ala Tyr Glu Lys Thr Asp Thr Asp Gly Lys Phe Leu Tyr His Lys Ser
            100                 105                 110 aaa tgg aac ata acc atg gag tcc tat gtg gtc cac acc aac tat gat      384
Lys Trp Asn Ile Thr Met Glu Ser Tyr Val Val His Thr Asn Tyr Asp
        115                 120                 125 gag tat gcc att ttc ctg acc aag aaa ttc agc cgc cat cat gga ccc      432
Glu Tyr Ala Ile Phe Leu Thr Lys Lys Phe Ser Arg His His Gly Pro
    130                 135                 140 acc att act gcc aag ctc tac ggg cgg gcg ccg cag ctg agg gaa act      480
Thr Ile Thr Ala Lys Leu Tyr Gly Arg Ala Pro Gln Leu Arg Glu Thr
145                 150                 155                 160 ctc ctg cag gac ttc aga gtg gtt gcc cag ggt gtg ggc atc cct gag      528
Leu Leu Gln Asp Phe Arg Val Val Ala Gln Gly Val Gly Ile Pro Glu
                165                 170                 175 gac tcc atc ttc acc atg gct gac cga ggt gaa tgt gtc cct ggg gag      576
Asp Ser Ile Phe Thr Met Ala Asp Arg Gly Glu Cys Val Pro Gly Glu
```

```
                      180               185               190
cag gaa cca gag ccc atc tta atc ccg                                    603
Gln Glu Pro Glu Pro Ile Leu Ile Pro
        195               200
```

<210> SEQ ID NO 79
<211> LENGTH: 201
<212> TYPE: PRT
<213> ORGANISM: Homo sapiens

<400> SEQUENCE: 79

```
Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
        130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro
        195                 200
```

<210> SEQ ID NO 80
<211> LENGTH: 603
<212> TYPE: DNA
<213> ORGANISM: Bos taurus
<220> FEATURE:
<221> NAME/KEY: CDS
<222> LOCATION: (1)..(603)

<400> SEQUENCE: 80

```
atg cgg agt ctc agc gga ctg ctg ttg tta ctg act gcc tgc ctg gca    48
Met Arg Ser Leu Ser Gly Leu Leu Leu Leu Leu Thr Ala Cys Leu Ala
1               5                   10                  15 gta aac gcc agc tcc gtg ccc aca ttg ccc gat gac att caa gtg cag    96
Val Asn Ala Ser Ser Val Pro Thr Leu Pro Asp Asp Ile Gln Val Gln
            20                  25                  30 gag aac ttc gac ctg tct agg atc tat ggg aag tgg ttc aat gtg gcc   144
Glu Asn Phe Asp Leu Ser Arg Ile Tyr Gly Lys Trp Phe Asn Val Ala
            35                  40                  45 gtg ggc tcc acc tgc cca tgg ctg aag agg ttc aag gag aag atg acc   192
Val Gly Ser Thr Cys Pro Trp Leu Lys Arg Phe Lys Glu Lys Met Thr
    50                  55                  60
```

```
atg agc aca gtg gtg ttg ata gcg ggg ccg acg agc aag gag atc agc    240
Met Ser Thr Val Val Leu Ile Ala Gly Pro Thr Ser Lys Glu Ile Ser
 65              70                  75                  80 gtc acc aac act cac agg cgg aaa ggt gtc tgt gaa tcg atc tct ggt    288
Val Thr Asn Thr His Arg Arg Lys Gly Val Cys Glu Ser Ile Ser Gly
             85                  90                  95 act tat gag aaa aca agc gct gat ggg aag ttt ctc tat cac aaa gcc    336
Thr Tyr Glu Lys Thr Ser Ala Asp Gly Lys Phe Leu Tyr His Lys Ala
         100                 105                 110 aag tgg aat atc acc atg gag tcc tat gtg gtc cac acc aac tac gat    384
Lys Trp Asn Ile Thr Met Glu Ser Tyr Val Val His Thr Asn Tyr Asp
     115                 120                 125 gag tac gcc att ttt ctg acc aag aaa tta agc cgt cga cat gga ccc    432
Glu Tyr Ala Ile Phe Leu Thr Lys Lys Leu Ser Arg Arg His Gly Pro
 130                 135                 140 acc att act gtc aag ctc tat ggg cgt gag ccg cag ctt cgg gaa agc    480
Thr Ile Thr Val Lys Leu Tyr Gly Arg Glu Pro Gln Leu Arg Glu Ser
145                 150                 155                 160 ctg ctg gag gaa ttc agg gag gtg gcc ctg ggt gtg ggc atc ccc gaa    528
Leu Leu Glu Glu Phe Arg Glu Val Ala Leu Gly Val Gly Ile Pro Glu
             165                 170                 175 gat gcc atc ttc aca atg ccc gac aga ggt gaa tgt gtt cct gga gag    576
Asp Ala Ile Phe Thr Met Pro Asp Arg Gly Glu Cys Val Pro Gly Glu
         180                 185                 190 cag gat cca gtg ccc act cca ctc tcg                                603
Gln Asp Pro Val Pro Thr Pro Leu Ser
     195                 200

<210> SEQ ID NO 81
<211> LENGTH: 201
<212> TYPE: PRT
<213> ORGANISM: Bos taurus

<400> SEQUENCE: 81

Met Arg Ser Leu Ser Gly Leu Leu Leu Leu Thr Ala Cys Leu Ala
  1               5                  10                  15

Val Asn Ala Ser Ser Val Pro Thr Leu Pro Asp Asp Ile Gln Val Gln
                 20                  25                  30

Glu Asn Phe Asp Leu Ser Arg Ile Tyr Gly Lys Trp Phe Asn Val Ala
             35                  40                  45

Val Gly Ser Thr Cys Pro Trp Leu Lys Arg Phe Lys Glu Lys Met Thr
 50                  55                  60

Met Ser Thr Val Val Leu Ile Ala Gly Pro Thr Ser Lys Glu Ile Ser
 65                  70                  75                  80

Val Thr Asn Thr His Arg Arg Lys Gly Val Cys Glu Ser Ile Ser Gly
                 85                  90                  95

Thr Tyr Glu Lys Thr Ser Ala Asp Gly Lys Phe Leu Tyr His Lys Ala
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Leu Ser Arg Arg His Gly Pro
    130                 135                 140

Thr Ile Thr Val Lys Leu Tyr Gly Arg Glu Pro Gln Leu Arg Glu Ser
145                 150                 155                 160

Leu Leu Glu Glu Phe Arg Glu Val Ala Leu Gly Val Gly Ile Pro Glu
                165                 170                 175

Asp Ala Ile Phe Thr Met Pro Arg Gly Glu Cys Val Pro Gly Glu
            180                 185                 190
```

```
Gln Asp Pro Val Pro Thr Pro Leu Ser
        195                 200

<210> SEQ ID NO 82
<211> LENGTH: 558
<212> TYPE: DNA
<213> ORGANISM: Sus scrofa domesticus
<220> FEATURE:
<221> NAME/KEY: CDS
<222> LOCATION: (1)..(558)

<400> SEQUENCE: 82 gcc gtg agc gcc agc cct gtg ctg aca ttg ccc aat gac atc cag gtg      48
Ala Val Ser Ala Ser Pro Val Leu Thr Leu Pro Asn Asp Ile Gln Val
1                5                  10                  15 cag gag aac ttc gac ctg tct agg atc tac ggg aaa tgg ttc cac gtg      96
Gln Glu Asn Phe Asp Leu Ser Arg Ile Tyr Gly Lys Trp Phe His Val
                20                  25                  30 gcc gtg ggc tcc acc tgc ccc tgg ctg aag agg ttc aag gac aag atg     144
Ala Val Gly Ser Thr Cys Pro Trp Leu Lys Arg Phe Lys Asp Lys Met
            35                  40                  45 acg atg ggc acg ctg atg ctg gga gag ggg gcg acg gag agg gag atc     192
Thr Met Gly Thr Leu Met Leu Gly Glu Gly Ala Thr Glu Arg Glu Ile
        50                  55                  60 agc gtg acc aag act cac cgg agg aaa ggt atc tgt gag gtg atc tct     240
Ser Val Thr Lys Thr His Arg Arg Lys Gly Ile Cys Glu Val Ile Ser
65                  70                  75                  80 ggg gct tat gag aaa aca agc act gat gga aag ttc ctc tat cac aaa     288
Gly Ala Tyr Glu Lys Thr Ser Thr Asp Gly Lys Phe Leu Tyr His Lys
                85                  90                  95 tcc aaa tgg aac atc acc atg gag tcc tat gtg gtc cac acc aac tat     336
Ser Lys Trp Asn Ile Thr Met Glu Ser Tyr Val Val His Thr Asn Tyr
            100                 105                 110 gat gag tat gcc ata ttt ctg acc aag aag ttc agc cgc cgc cac gga     384
Asp Glu Tyr Ala Ile Phe Leu Thr Lys Lys Phe Ser Arg Arg His Gly
        115                 120                 125 ccc acc ctt act gcc aag ctc tac ggg cgg gag ccg cag ctt cgg gaa     432
Pro Thr Leu Thr Ala Lys Leu Tyr Gly Arg Glu Pro Gln Leu Arg Glu
    130                 135                 140 agc ctg ctg gag gag ttc agg gag gtt gcc ctg ggc gtg ggc atc ccg     480
Ser Leu Leu Glu Glu Phe Arg Glu Val Ala Leu Gly Val Gly Ile Pro
145                 150                 155                 160 gag gac tcc atc ttt acg atg ccc gac aga ggg gag tgt gtc cct ggg     528
Glu Asp Ser Ile Phe Thr Met Pro Asp Arg Gly Glu Cys Val Pro Gly
                165                 170                 175 gag cag gag cct gag ccc acc cta ctc tca                             558
Glu Gln Glu Pro Glu Pro Thr Leu Leu Ser
            180                 185

<210> SEQ ID NO 83
<211> LENGTH: 186
<212> TYPE: PRT
<213> ORGANISM: Sus scrofa domesticus

<400> SEQUENCE: 83

Ala Val Ser Ala Ser Pro Val Leu Thr Leu Pro Asn Asp Ile Gln Val
1                5                  10                  15

Gln Glu Asn Phe Asp Leu Ser Arg Ile Tyr Gly Lys Trp Phe His Val
                20                  25                  30

Ala Val Gly Ser Thr Cys Pro Trp Leu Lys Arg Phe Lys Asp Lys Met
            35                  40                  45

Thr Met Gly Thr Leu Met Leu Gly Glu Gly Ala Thr Glu Arg Glu Ile
```

```
                50                  55                  60
Ser Val Thr Lys Thr His Arg Arg Lys Gly Ile Cys Glu Val Ile Ser
 65                  70                  75                  80

Gly Ala Tyr Glu Lys Thr Ser Thr Asp Gly Lys Phe Leu Tyr His Lys
                 85                  90                  95

Ser Lys Trp Asn Ile Thr Met Glu Ser Tyr Val Val His Thr Asn Tyr
            100                 105                 110

Asp Glu Tyr Ala Ile Phe Leu Thr Lys Lys Phe Ser Arg His Gly
            115                 120                 125

Pro Thr Leu Thr Ala Lys Leu Tyr Gly Arg Glu Pro Gln Leu Arg Glu
            130                 135                 140

Ser Leu Leu Glu Glu Phe Arg Glu Val Ala Leu Gly Val Gly Ile Pro
145                 150                 155                 160

Glu Asp Ser Ile Phe Thr Met Pro Asp Arg Gly Glu Cys Val Pro Gly
                165                 170                 175

Glu Gln Glu Pro Glu Pro Thr Leu Leu Ser
            180                 185

<210> SEQ ID NO 84
<211> LENGTH: 600
<212> TYPE: DNA
<213> ORGANISM: Rattus norvegicus
<220> FEATURE:
<221> NAME/KEY: CDS
<222> LOCATION: (1)..(600)

<400> SEQUENCE: 84
```

| | | | | | | | | | | | | | | | | |
|---|---|---|---|---|---|---|---|---|---|---|---|---|---|---|---|---|
| atg | cag | ggt | ctc | ggg | gcc | ctg | ttc | ttg | ttg | ctg | act | gcc | tgc | ctc | act | 48 |
| Met | Gln | Gly | Leu | Gly | Ala | Leu | Phe | Leu | Leu | Leu | Thr | Ala | Cys | Leu | Thr | |
| 1 | | | | 5 | | | | | 10 | | | | | 15 | | |
| ttg | aag | gct | gac | aat | gtg | cca | aca | ctg | cca | gat | atc | cag | gtt | cag | gag | 96 |
| Leu | Lys | Ala | Asp | Asn | Val | Pro | Thr | Leu | Pro | Asp | Ile | Gln | Val | Gln | Glu | |
| | | | 20 | | | | | 25 | | | | | 30 | | | |
| aac | ttc | aat | gag | gcc | cgg | atc | tat | gga | aaa | tgg | ttc | aac | ctg | gcg | gtg | 144 |
| Asn | Phe | Asn | Glu | Ala | Arg | Ile | Tyr | Gly | Lys | Trp | Phe | Asn | Leu | Ala | Val | |
| | | 35 | | | | | 40 | | | | | 45 | | | | |
| ggc | tcc | acc | tgc | ccg | tgg | ctg | agg | cgg | att | aag | aac | aag | atg | agc | gtg | 192 |
| Gly | Ser | Thr | Cys | Pro | Trp | Leu | Arg | Arg | Ile | Lys | Asn | Lys | Met | Ser | Val | |
| | 50 | | | | | 55 | | | | | 60 | | | | | |
| agc | aca | ctg | gtg | ctg | cag | gag | ggg | gcg | aca | gaa | gcc | gag | atc | agc | gtg | 240 |
| Ser | Thr | Leu | Val | Leu | Gln | Glu | Gly | Ala | Thr | Glu | Ala | Glu | Ile | Ser | Val | |
| 65 | | | | 70 | | | | | 75 | | | | | 80 | | |
| acc | agt | act | caa | tgg | cgg | aaa | ggt | gtc | tgc | gag | gag | atc | tcc | ggg | gtg | 288 |
| Thr | Ser | Thr | Gln | Trp | Arg | Lys | Gly | Val | Cys | Glu | Glu | Ile | Ser | Gly | Val | |
| | | | 85 | | | | | 90 | | | | | 95 | | | |
| tat | cag | aag | aca | gac | att | gac | gga | aag | ttc | ctt | tac | cac | aaa | tcc | aaa | 336 |
| Tyr | Gln | Lys | Thr | Asp | Ile | Asp | Gly | Lys | Phe | Leu | Tyr | His | Lys | Ser | Lys | |
| | | 100 | | | | | 105 | | | | | 110 | | | | |
| tgg | aat | gca | acc | ttg | gaa | tct | tat | gtg | gtc | cac | acc | aac | tat | gac | gaa | 384 |
| Trp | Asn | Ala | Thr | Leu | Glu | Ser | Tyr | Val | Val | His | Thr | Asn | Tyr | Asp | Glu | |
| | 115 | | | | | 120 | | | | | 125 | | | | | |
| tat | gcc | att | ttc | ctt | acc | aag | aag | ttc | agc | cac | cgc | cac | gga | ccc | acc | 432 |
| Tyr | Ala | Ile | Phe | Leu | Thr | Lys | Lys | Phe | Ser | His | Arg | His | Gly | Pro | Thr | |
| 130 | | | | | 135 | | | | | 140 | | | | | | |
| atc | act | gcc | aag | ctc | tat | ggc | cgg | gaa | cca | cag | ctg | agg | gac | agc | ctt | 480 |
| Ile | Thr | Ala | Lys | Leu | Tyr | Gly | Arg | Glu | Pro | Gln | Leu | Arg | Asp | Ser | Leu | |
| 145 | | | | | 150 | | | | | 155 | | | | | 160 | |
| ctg | cag | gag | ttc | agg | gag | gtg | gcc | ctg | agt | gtg | ggc | atc | cct | gag | aac | 528 |
| Leu | Gln | Glu | Phe | Arg | Glu | Val | Ala | Leu | Ser | Val | Gly | Ile | Pro | Glu | Asn | |
| | | | 165 | | | | | 170 | | | | | 175 | | | |

```
tcc att gtt ttt atg gcc gac aga gga gaa tgt gtc cct ggg gat cgg    576
Ser Ile Val Phe Met Ala Asp Arg Gly Glu Cys Val Pro Gly Asp Arg
        180                 185                 190 gag gta gag tcc act tca ttt gca                                    600
Glu Val Glu Ser Thr Ser Phe Ala
        195                 200

<210> SEQ ID NO 85
<211> LENGTH: 200
<212> TYPE: PRT
<213> ORGANISM: Rattus norvegicus

<400> SEQUENCE: 85

Met Gln Gly Leu Gly Ala Leu Phe Leu Leu Leu Thr Ala Cys Leu Thr
1               5                   10                  15

Leu Lys Ala Asp Asn Val Pro Thr Leu Pro Asp Ile Gln Val Gln Glu
            20                  25                  30

Asn Phe Asn Glu Ala Arg Ile Tyr Gly Lys Trp Phe Asn Leu Ala Val
        35                  40                  45

Gly Ser Thr Cys Pro Trp Leu Arg Arg Ile Lys Asn Lys Met Ser Val
    50                  55                  60

Ser Thr Leu Val Leu Gln Glu Gly Ala Thr Glu Ala Glu Ile Ser Val
65                  70                  75                  80

Thr Ser Thr Gln Trp Arg Lys Gly Val Cys Glu Ile Ser Gly Val
                85                  90                  95

Tyr Gln Lys Thr Asp Ile Asp Gly Lys Phe Leu Tyr His Lys Ser Lys
            100                 105                 110

Trp Asn Ala Thr Leu Glu Ser Tyr Val Val His Thr Asn Tyr Asp Glu
        115                 120                 125

Tyr Ala Ile Phe Leu Thr Lys Lys Phe Ser His Arg His Gly Pro Thr
    130                 135                 140

Ile Thr Ala Lys Leu Tyr Gly Arg Glu Pro Gln Leu Arg Asp Ser Leu
145                 150                 155                 160

Leu Gln Glu Phe Arg Glu Val Ala Leu Ser Val Gly Ile Pro Glu Asn
                165                 170                 175

Ser Ile Val Phe Met Ala Asp Arg Gly Glu Cys Val Pro Gly Asp Arg
            180                 185                 190

Glu Val Glu Ser Thr Ser Phe Ala
        195                 200

<210> SEQ ID NO 86
<211> LENGTH: 30
<212> TYPE: DNA
<213> ORGANISM: Artificial Sequence
<220> FEATURE:
<223> OTHER INFORMATION: Synthetic 5' end of First strand cDNA

<400> SEQUENCE: 86
agcatcgagt cggccttgtt ggcctactgg                                   30

<210> SEQ ID NO 87
<211> LENGTH: 25
<212> TYPE: DNA
<213> ORGANISM: Artificial Sequence
<220> FEATURE:
<223> OTHER INFORMATION: Synthetic Added 3' end Sequence

<400> SEQUENCE: 87
gcggctgaag acggcctatg tgcct                                        25
```

```
<210> SEQ ID NO 88
<211> LENGTH: 34
<212> TYPE: DNA
<213> ORGANISM: Artificial Sequence
<220> FEATURE:
<223> OTHER INFORMATION: Synthetic Complementary Sequence of Added 3'
      end Sequence

<400> SEQUENCE: 88 ttttttttt ggcacatagg ccgtcttcag ccgc                                      34
```